US011521738B2

(12) United States Patent
Toth et al.

(10) Patent No.: US 11,521,738 B2
(45) Date of Patent: Dec. 6, 2022

(54) MEDICAL DEVICES WITH CIRCUITRY FOR CAPTURING AND PROCESSING PHYSIOLOGICAL SIGNALS

(71) Applicant: Autonomix Medical, Inc., Ivyland, PA (US)

(72) Inventors: Landy Toth, Doylestown, PA (US); Siu Bor Lau, Doylestown, PA (US)

(73) Assignee: Autonomix Medical, Inc., Ivyland, PA (US)

( * ) Notice: Subject to any disclaimer, the term of this patent is extended or adjusted under 35 U.S.C. 154(b) by 179 days.

(21) Appl. No.: 16/757,155

(22) PCT Filed: Oct. 17, 2018

(86) PCT No.: PCT/US2018/056195
§ 371 (c)(1),
(2) Date: Apr. 17, 2020

(87) PCT Pub. No.: WO2019/079378
PCT Pub. Date: Apr. 25, 2019

(65) Prior Publication Data
US 2020/0342985 A1    Oct. 29, 2020

Related U.S. Application Data

(60) Provisional application No. 62/573,924, filed on Oct. 18, 2017.

(51) Int. Cl.
*G16H 40/63*    (2018.01)
*A61B 5/01*    (2006.01)
(Continued)

(52) U.S. Cl.
CPC ............ *G16H 40/63* (2018.01); *A61B 5/01* (2013.01); *A61B 5/14503* (2013.01); *A61B 5/30* (2021.01);
(Continued)

(58) Field of Classification Search
CPC .. G16H 40/63; A61B 5/30; A61B 5/01; A61B 5/14503; A61B 5/6852;
(Continued)

(56) References Cited

U.S. PATENT DOCUMENTS 3,552,384 A * 1/1971 Pierie ................ A61M 25/0147
604/95.04
6,242,950 B1    6/2001 Bozso et al.
(Continued)

FOREIGN PATENT DOCUMENTS

EP          18868117        10/2021
WO       2014/160832 A2    10/2014
WO  PCT/US2018/056195     3/2019

OTHER PUBLICATIONS

Defossez, "D-PHY Solutions", Xilinx, Aug. 25, 2014 (Year: 2014).*
(Continued)

*Primary Examiner* — Phong H Dang
(74) *Attorney, Agent, or Firm* — Ryan, Mason & Lewis, LLP

(57) ABSTRACT

A medical device comprises a control system, processing modules, and a wire bundle connecting the control system to the processing modules, the wire bundle comprising control lines and data lines. Each processing module is coupled to a respective set of sensors arranged to interface with a biological tissue site, the sensors being configured to capture analog physiological signals generated from the biological tissue site. The control system is configured to generate a control signal on the control lines to initiate a data collection cycle by the processing modules. In response to the control signal, each processing module is configured to perform a respective data collection process which comprises (i) capturing and processing an analog physiological signal on each enabled sensor to generate a data sample for each analog (Continued)

physiological signal captured on each enabled sensor, and (ii) outputting data samples to the control system on the data lines.

25 Claims, 16 Drawing Sheets

(51) Int. Cl.
*A61B 5/145* (2006.01)
*A61B 5/00* (2006.01)
*G06F 13/38* (2006.01)
*A61M 25/00* (2006.01)
*H04L 9/40* (2022.01)
*G06F 13/14* (2006.01)
*H04L 12/54* (2022.01)
*H04Q 11/04* (2006.01)
*G06F 13/37* (2006.01)
*G06F 3/00* (2006.01)
*A61B 5/30* (2021.01)
*A61B 90/00* (2016.01)
*A61B 5/026* (2006.01)

(52) U.S. Cl.
CPC ............ *A61B 5/6852* (2013.01); *A61M 25/00* (2013.01); *G06F 3/00* (2013.01); *G06F 13/14* (2013.01); *G06F 13/37* (2013.01); *G06F 13/38* (2013.01); *H04L 12/56* (2013.01); *H04L 63/0823* (2013.01); *H04Q 11/04* (2013.01); *A61B 5/026* (2013.01); *A61B 2090/064* (2016.02); *A61B 2562/0219* (2013.01); *A61B 2562/0223* (2013.01); *A61B 2562/0261* (2013.01); *A61B 2562/222* (2013.01); *G06F 2213/40* (2013.01)

(58) Field of Classification Search
CPC .......... A61M 25/00; G06F 3/00; G06F 13/14; G06F 13/37; G06F 13/38; H04L 12/56; H04L 63/0823; H04Q 11/04
See application file for complete search history.

(56) References Cited

U.S. PATENT DOCUMENTS

| | | | |
|---|---|---|---|
| 7,844,333 B1 | 11/2010 | Koh et al. | |
| 2001/0047127 A1* | 11/2001 | New, Jr. | ............... A61B 5/282 600/300 |
| 2003/0073915 A1* | 4/2003 | McLeod | .............. A61B 5/7475 600/509 |
| 2003/0227573 A1 | 12/2003 | Testin | |
| 2008/0287770 A1* | 11/2008 | Kurzweil | ............. A61B 5/6804 600/388 |
| 2011/0238960 A1* | 9/2011 | Nakatomi | ......... G06F 15/17375 712/225 |
| 2014/0094674 A1* | 4/2014 | Nurmikko | .......... A61N 1/37223 607/45 |
| 2016/0029960 A1* | 2/2016 | Toth | ........................ A61N 1/05 606/41 |
| 2016/0202983 A1 | 7/2016 | Lin | |
| 2016/0346045 A1* | 12/2016 | Sterrett | .................. A61B 5/065 |

OTHER PUBLICATIONS

Marc Defossez, "D-PHY Solutions," XILINX All Programmable, https://www.xilinx.com/support/documentation/application_notes/xapp894-d-phy-solutions.pdf, Aug. 25, 2014, pp. 1-24.

* cited by examiner

FIG. 2A
FIG. 2B
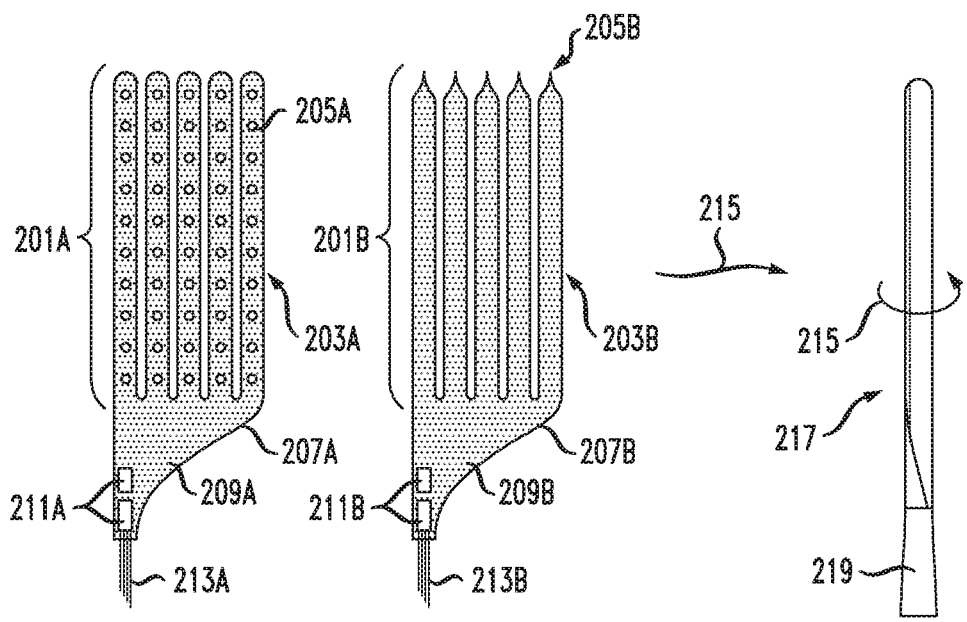
FIG. 2C
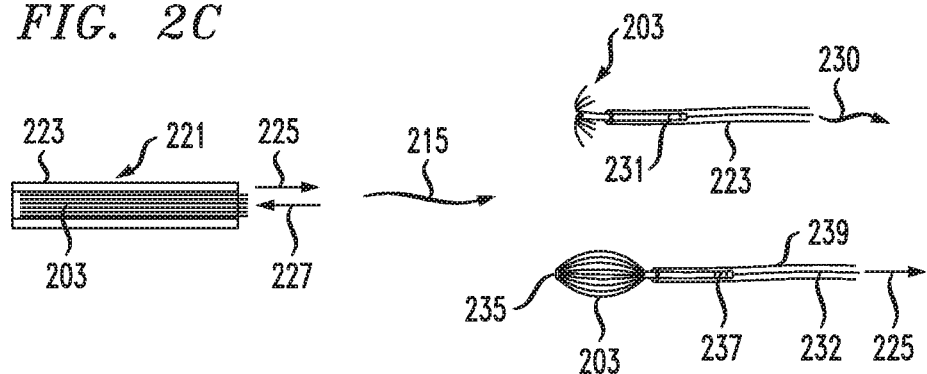
FIG. 2D
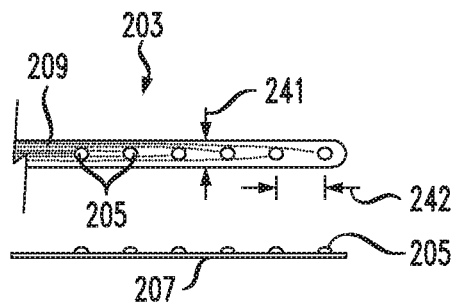

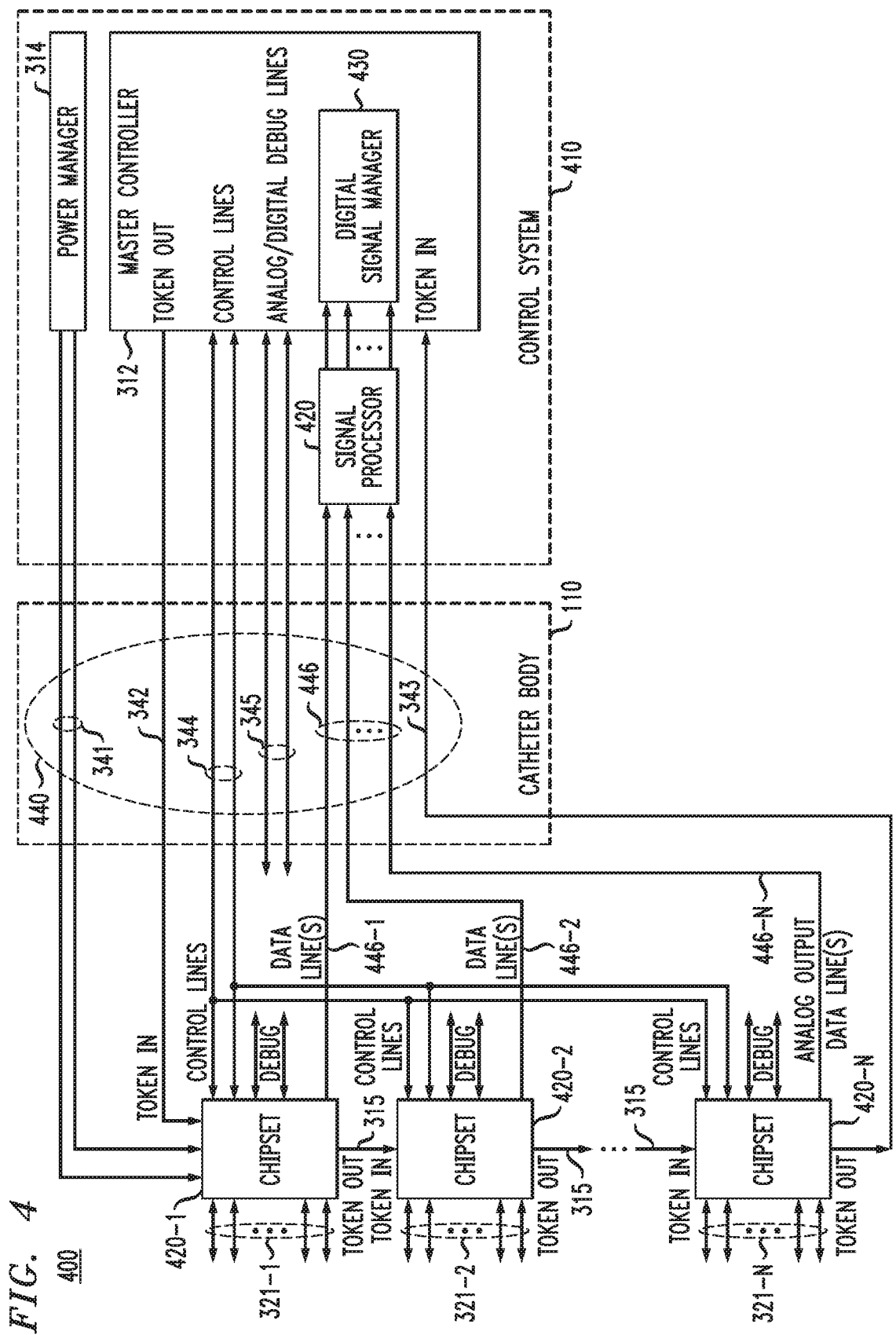

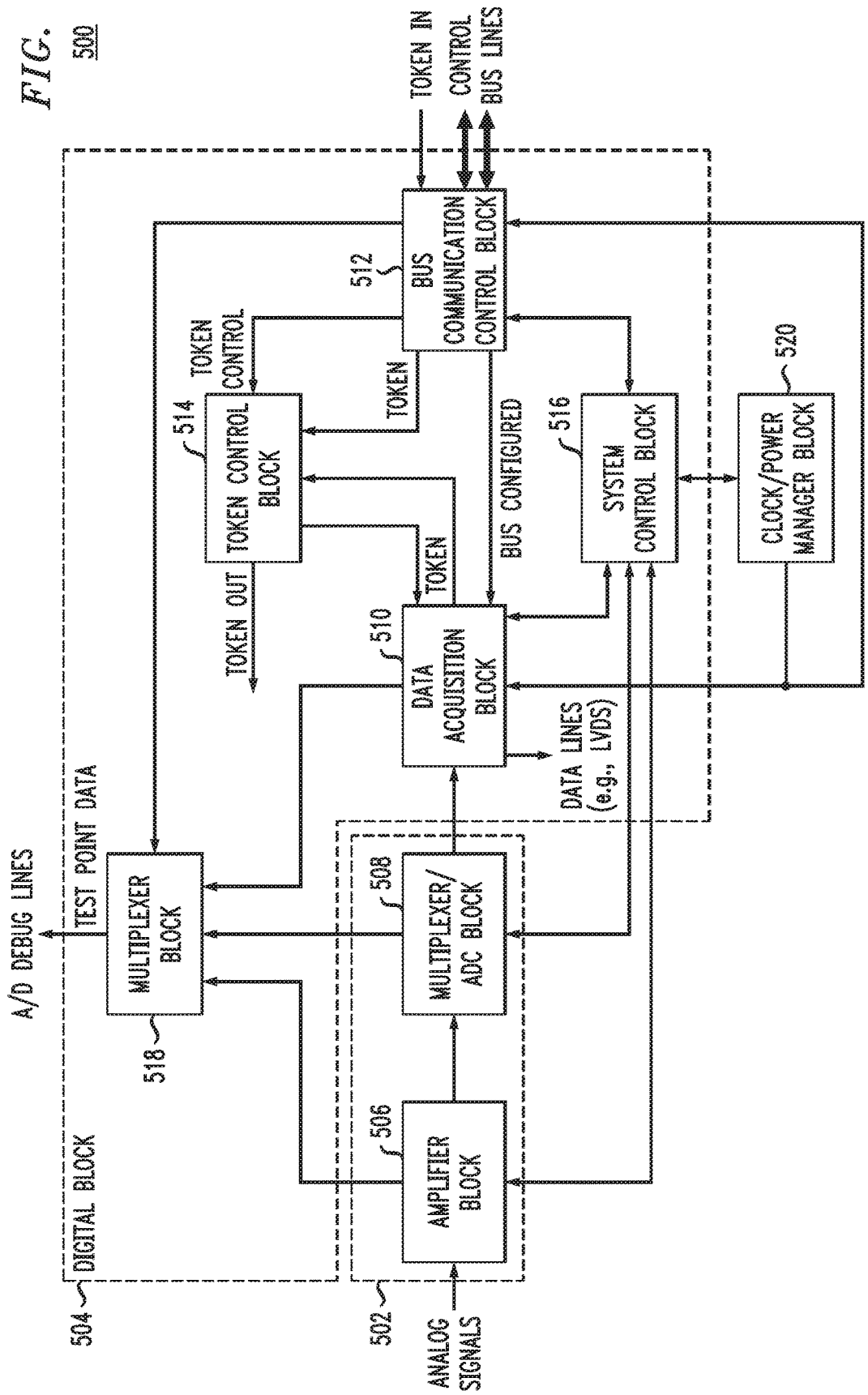

700

710

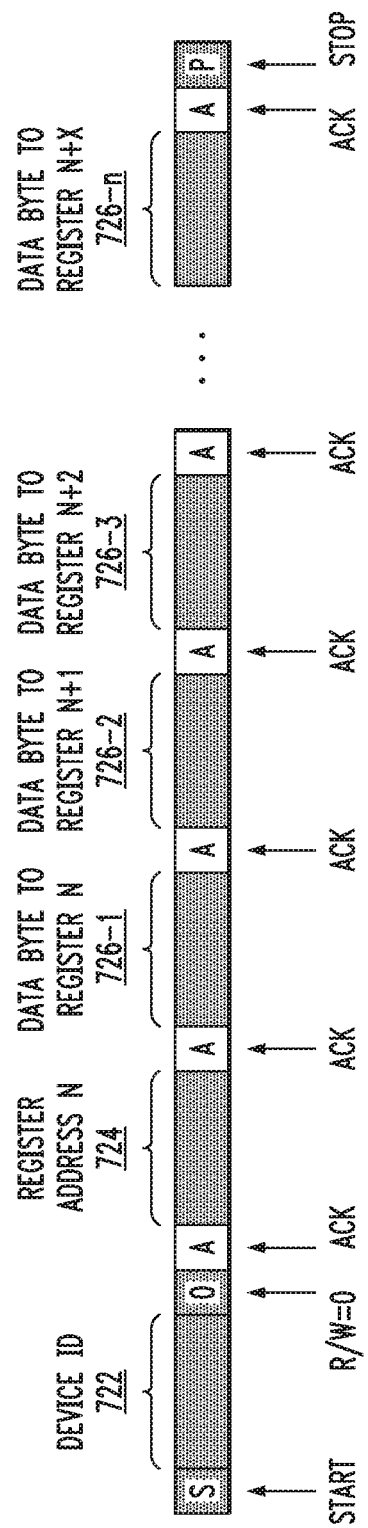

800

1000

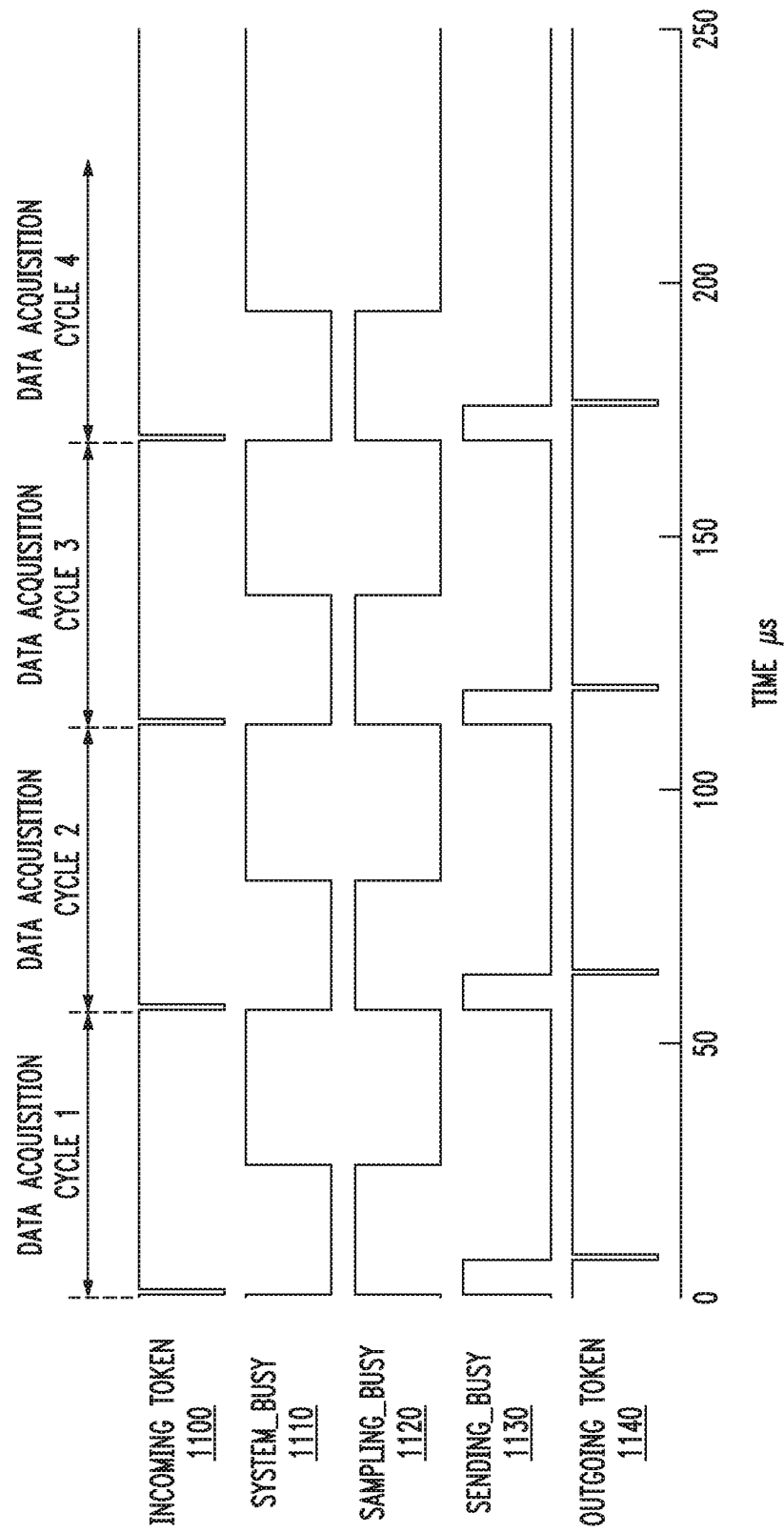

MEDICAL DEVICES WITH CIRCUITRY FOR CAPTURING AND PROCESSING PHYSIOLOGICAL SIGNALS

CROSS-REFERENCE TO RELATED APPLICATIONS

This application is a U.S. National Stage Application of International Application No. PCT/US2018/056195, filed on Oct. 17, 2018, which claims the benefit of and priority to U.S. Provisional Application Ser. No. 62/573,924, filed on Oct. 18, 2017, the disclosures of which are fully incorporated by reference herein for all purposes.

TECHNICAL FIELD

The field relates generally to medical devices, such as diagnostic catheters, and methods for acquiring and processing physiological signals, such as electrophysiological (EP) signals, using medical devices.

BACKGROUND

Electrophysiology is the study of the electrical properties of biological cells and tissue, and generally involves obtaining and processing measurements of changes in voltage or electrical current in biological tissue or in entire organs such as a heart. Electrophysiology techniques involve placing electrodes in contact with biological tissue at target regions within an organ using a medical device, such as a diagnostic catheter device. In general, a conventional diagnostic catheter device comprises a long, flexible hollow catheter tube (referred to as catheter body or guidewire) with a sensing tip disposed on one end of the catheter tube, and a connector disposed at another end of the catheter tube. The sensing tip comprises a plurality of sensing electrodes which are configured to sense and acquire electrophysiological signals from biological tissue in contact with, or in proximity to, the sensing electrodes. In addition, the catheter tube comprises a bundle of wires that extend through the catheter tube to connect the sensing electrodes of the sensing tip to the connector at the other end of the catheter tube. The electrophysiological signals captured by the sensing electrodes are sent along the wire bundle through the catheter tube to the connector at the end of the catheter tube. The captured signals can then be input to an external processing system (e.g., amplifiers, signal processors, digitizers, etc.) via an external cable/connector which is coupled to the catheter connector.

SUMMARY

Embodiments of the invention generally include medical devices such as diagnostic catheters, which are configured to acquire and process physiological signals, as well as methods for acquiring and processing physiological signals.

In some embodiments, a medical device comprises a control system, a plurality of processing modules, and a wire bundle connecting the control system to the plurality of processing modules, wherein the wire bundle comprises control lines and data lines. Each processing module is coupled to a respective set of sensors arranged to interface with a biological tissue site, wherein the sensors are configured to capture analog physiological signals generated from the biological tissue site. The control system is configured to generate a control signal on the control lines to initiate a data collection cycle by the plurality of processing modules. In response to the control signal, each processing module of the plurality of processing modules is configured to perform a respective data collection process which comprises (i) capturing and processing an analog physiological signal on each enabled sensor in the respective set of sensors of the processing module to generate a data sample for each analog physiological signal captured on each enabled sensor, and (ii) outputting data samples to the control system on the data lines.

In some embodiments, the data samples output on the data lines comprise analog signals.

In some embodiments, the data samples output on the data lines comprise digitally encoded signals.

In some embodiments, the data lines comprise separate data lines connecting data output ports of respective processing modules to the control system.

In some embodiments, the data lines comprise a time-shared data bus which is utilized by each processing module to output the data samples to the control system under a time-sharing protocol.

In some embodiments, the time-shared data bus comprises a two-wire data bus.

In some embodiments, the control lines comprise a bi-directional control bus comprising two control lines, wherein the control system is configured as master device on the bi-directional control bus, and wherein each processing module is configured as a slave device on the bi-directional control bus.

In some embodiments, each processing module comprises a set of control registers with configuration data to control functions of the processing modules, and wherein the control system communicates with the processing modules on the bi-directional control bus to read configuration data from, and write configuration data to, the control registers of the processing modules.

In some embodiments, the control registers of each processing module comprise a control register with configuration data that instructs the processing module to selectively enable or disable individual sensors in the respective set of sensors for capturing and processing analog physiological signals on the sensors.

In some embodiments, the control registers of each processing module comprise a control register with configuration data that instructs the processing module to adaptively increase a data throughput rate for signal channels coupled to enabled sensors.

In some embodiments, communication over the control lines and the data lines is asynchronous such that the control system can change the functionalities of the processing modules by issuing control commands on the control line without interrupting the communication of data samples on the data lines by the processing modules.

In some embodiments, the processing modules perform respective data sampling operations in parallel, and wherein the outputting of data samples to the control system on the data lines is performed by the processing modules on a time-shared basis.

In some embodiments, each processing module comprises: amplifier circuitry configured to amplify the analog physiological signals captured on the respective set of sensors of the processing module, wherein the amplifier circuitry comprises multiple parallel channels of amplifiers, wherein each amplifier channel is configured to amplify the analog physiological signal captured on a respective one of the sensors of the set of sensors, and generate an amplified physiological signal; a multiplexer circuit connected to outputs of the amplifier channels; and data output control circuitry connected to an output of the multiplexer circuit, wherein the data output control circuity comprises data line driver circuitry connected to at least one data line of the data lines, wherein the multiplexer circuit is configured to sequentially connect the amplified physiological signals at the outputs of the amplifier channels to an input of the data output control circuitry, and wherein the data output control circuitry is configured to (i) sequentially receive the amplified physiological signals for each sensor which are selectively output from the multiplexer circuit, and (ii) sequentially output the amplified physiological analog signals on the at least one data line.

In some embodiments, each processing module comprises: amplifier circuitry configured to amplify the analog physiological signals captured on the respective set of sensors of the processing module, wherein the amplifier circuitry comprises multiple parallel channels of amplifiers, wherein each amplifier channel is configured to amplify the analog physiological signal captured on a respective one of the sensors of the set of sensors, and generate an amplified physiological signal; a multiplexer circuit connected to outputs of the amplifier channels; analog-to-digital conversion (ADC) circuitry connected to an output of the multiplexer circuit; and data output control circuitry connected to at least one data line of the data lines, wherein the multiplexer circuit is configured to sequentially connect the amplified physiological signals at the outputs of the amplifier channels to an input of the ADC circuitry, wherein the ADC circuitry is configured to (i) sequentially receive the amplified physiological signals for each sensor which are selectively output from the multiplexer circuit, and (ii) digitally sample the amplified physiological signals output from the amplifier circuitry and generate a separate block of digital samples for each amplified physiological signal output from the amplifier circuitry, and wherein the data output control circuitry is configured to encode the blocks of digital samples generated by the ADC circuitry and output the encoded blocks of digital samples on the at least one data line.

In some embodiments, each processing module further comprises a memory block comprising a first memory array and a second memory array, wherein the first memory array is configured to store blocks of digital samples generated by the ADC circuitry during a current data collection cycle initiated by the control system and wherein the second memory array is configured to store blocks of digital samples generated by the ADC circuitry during a previous data collection cycle previously initiated by the control system.

In some embodiments, during a current data collection cycle initiated by the control system, the data output control circuitry is configured to encode and output the blocks of digital samples stored in the second memory array, while the ADC circuitry generates and stores the blocks of digital samples for the current data collection cycle in the first memory array.

In some embodiments, the first memory array comprises a first register array and the second memory array comprise a second register array, wherein the first and second register arrays each comprise a separate register for each amplifier channel to store respective blocks of digital samples associated with the respective amplifier channels.

In some embodiments, the data output control circuitry comprises a data frame generator configured to generate a data frame for each block of digital samples, a serializer and encoder circuit configured to combine the data frames into a device frame and line encode the device frame for transmission over the at least one data line, and data line driver circuitry configured to output the device frame on the at least one data line.

In some embodiments, the serializer and encoder circuit are configured to encode the data frames using a Manchester coding protocol.

In some embodiments, the data line driver circuitry is configured to implement differential, serial transmission of the encoded device frame on a two-wire data bus.

In some embodiments, the data line driver circuitry implements a low voltage differential signaling (LVDS) data transmission protocol.

In some embodiments, the plurality of processing modules includes N processing modules arranged in a sequence starting from a first processing module to an $N^{th}$ processing module, the control lines comprise a first token control line and a second token control line, each processing module comprises a Token IN port and a Token OUT port, the first token control line is connected to a Token OUT port of the control system and to the Token IN port of the first processing module, the second token control line is connected to the Token OUT port of the $N^{th}$ processing module and to a Token IN port of the control system, and the Token OUT port of each processing module in the sequence from the first processing module to the $N^{th}$-1 processing module is connected to the Token IN port of a next successive processing module by chip-to-chip token control lines, thereby forming the sequence of processing modules from the first processing module to the $N^{th}$ processing module.

In some embodiments, a sequence and timing of operations performed by the processing modules are controlled using a token-based protocol in which a control token is output on the first token control line from the control system to the first processing module, wherein the control token is passed downstream to each successive processing module in the sequence via the chip-to-chip token control lines, wherein each processing module performs one or more operations when holding the control token, and when the one or more operations are completed, the processing module passes the control token to the next successive processing module to initiate the same one or more operations in the next successive processing module, wherein when the $N^{th}$ processing module completes the same one or more operations, the $N^{th}$ processing module passes the control token back to the control system on the second token control line, which indicates to the control system that a current operation cycle is complete.

In some embodiments, the token-based protocol is implemented by the control system to dynamically assign a unique Device ID address to each processing module.

In some embodiments, the token-based protocol is implemented to initiate and control the data collection cycle implemented by the processing modules, wherein the control signal that is generated by the control system comprises a token control signal on the first token control line, wherein each processing module is configured to perform the respective data collection process when the processing module is holding the token control signal.

In some embodiments, the medical device comprises a catheter device comprising a catheter body, at least one sensing tip disposed at a distal end of the catheter body, and a torquer element disposed at proximal end of the catheter body, the sensors and the processing modules are integrated with the at least one sensing tip at the distal end of the catheter body, the control system is integrated with the torquer element, and the wire bundle extends through the catheter body.

In some embodiments, the torquer element comprises a power source to supply power to the processing modules, and a wireless transceiver to enable wireless communication between the control system and a remote processing system.

In some embodiments, the torquer element is detachably connected to the catheter body.

In some embodiments, the control wires of the wire bundle comprise a shared bi-directional control bus comprising two control lines to enable the control system to communicate with each of the processing modules, and wherein the data lines comprise a two-wire time-shared data bus connecting data outputs of each processing module to the control system.

In some embodiments, the plurality of processing modules includes N processing modules, wherein N is 8 or more, each respective set of sensors comprises one or more sensing electrodes, the set of sensing electrodes comprises M sensing electrodes, wherein M is 16 or greater, and a total number of control wires and data wires of the wire bundle is 10 or less.

In some embodiments, the plurality of processing modules includes N processing modules, wherein N is 2 or more, each respective set of sensors comprises one or more sensing electrodes, the set of sensing electrodes comprises M sensing electrodes, wherein M is 8 or greater, and a total number of control wires and data wires of the wire bundle is 12 or less.

In some embodiments, the plurality of processing modules includes N processing modules, wherein N is 64 or more, each respective set of sensors comprises one or more sensing electrodes, the set of sensing electrodes comprises M sensing electrodes, wherein M is 16 or greater, and a total number of control wires and data wires of the wire bundle is 14 or less.

In some embodiments, one or more of the sensors comprises one of a sense electrode, an accelerometer, a force sensor, a tactile sensor, a strain sensor, a temperature sensor, a magnetic sensor, a fluid analyte sensor, and a flow sensor.

In some embodiments, a medical device, comprises a control system, a plurality N of processing modules arranged in a sequence starting from a first processing module to an $N^{th}$ processing module, and a wire bundle connecting the control system to the plurality of processing modules, wherein the wire bundle comprises (i) control lines comprising a shared bi-directional control bus, a first token control line, and a second token control line, and (ii) data lines comprising a shared digital data bus. Each processing module is coupled to a respective set of sensors arranged to interface with a biological tissue site, wherein the sensors are configured to capture analog physiological signals generated from the biological tissue site. Each processing module comprises a Token IN port and a Token OUT port. The first token control line is connected to a Token OUT port of the control system and to the Token IN port of the first processing module. The second token control line is connected to the Token OUT port of the $N^{th}$ processing module and to a Token IN port of the control system. The Token OUT port of each processing module in the sequence from the first processing module to the $N^{th}$-1 processing module is connected to the Token IN port of a next successive processing module by chip-to-chip token control lines. The control system is configured to generate a token signal on the first token control line which is sequentially passed to each processing module to perform a current a data collection cycle by the plurality of processing modules, and then passed back to the control system from the $N^{th}$ processing module on the second token control line to indicate to the control system that the current data collection cycle is complete.

In some embodiments, in response to receipt of the token signal at the Token IN port of a given processing module from one of the control system and an upstream processing module, the given processing module is configured to perform a respective current data collection process which comprises (i) amplifying an analog physiological signal captured on each sensor of the set of sensors to generate a set of amplified physiological signals, (ii) digitally sampling each of the amplified physiological signals to generate a separate block of digital samples for each amplified physiological signal, and (iii) digitally encoding and outputting blocks of digital samples, which were generated during a previous data collection cycle, on the shared digital data bus to the control system.

In some embodiments, the control system is configured to generate a control command on the shared bi-directional control bus, which is addressed to one or more of the processing modules, to dynamically adjust at least one operating parameter of a least one of the amplifying, the digital sampling, the encoding, and the outputting operations of the one or more processing modules.

In some embodiments, each processing module outputs the token control signal on the Token OUT port of the processing module upon completion of the encoding and outputting operations, irrespective of whether the digital sampling operation is complete.

In some embodiments, each processing module further comprises a memory block comprising a first memory array and a second memory array, wherein the first memory array is configured to store blocks of digital samples generated by the processing module during the current data collection cycle and the second memory array is configured to store blocks of digital samples generated by the processing module during the previous data collection cycle.

In some embodiments, the medical device comprises a catheter device comprising a catheter body, at least one sensing tip disposed at a distal end of the catheter body, and a torquer element disposed at proximal end of the catheter body, the sensors and the processing modules are integrated with the at least one sensing tip at the distal end of the catheter body, the control system is integrated with the torquer element, and the wire bundle extends through the catheter body.

In some embodiments, a number N of processing modules is 8 or more, each respective set of sensors comprises M sensors, wherein M is 16 or greater, and a total number of wires in the wire bundle is 10 or less.

In some embodiments, one or more of the sensors comprises one of a sense electrode, an accelerometer, a force sensor, a tactile sensor, a strain sensor, a temperature sensor, a magnetic sensor, a fluid analyte sensor, and a flow sensor.

In some embodiments, a method comprises placing an array of sensors in contact with, or in proximity to, biological tissue to be tested, wherein the sensors are configured to capture analog physiological signals generated in the biological tissue, and wherein the array of sensors comprises N sets of sensors wherein each set of sensors is coupled to a respective one of N processing modules, and controlling the processing modules, with a control signal generated from a control system, to perform a data collection cycle which comprises the processing modules operating in a controlled sequence from a first processing module to an $N^{th}$ processing module to perform a respective data collection process which comprises (i) capturing and processing analog physiological signals on each enabled sensor of the respective set of sensors coupled to the processing module to generate a data sample for each analog physiological signal captured on the each enabled sensor, and (ii) outputting data samples to the control system on a data bus.

In some embodiments, processing the captured analog physiological signals comprises digitally sampling the captured analog physiological signals to generate digital samples, and wherein outputting data samples to the control system on the data bus comprises outputting digital samples that were generated by the processing module during a previous data collection process.

In some embodiments, outputting data samples to the control system comprises digitally encoding the digital samples into data frames, and transmitting the data frames on a digital data bus that is shared by each of the processing modules.

In some embodiments, the method further comprises storing the digital samples generated by the processing module during a current data collection process in a first memory array, accessing digital data samples stored in a second memory array, encoding the digital samples accessed from the second memory array, and outputting the encoded digital samples on a digital data bus that is shared by each of the processing modules, wherein the digital samples stored in the second memory array comprise digital samples that were generated by the processing module during a previous data collection process.

In some embodiments, the capturing and processing analog physiological signals on each enabled sensor, and the outputting of data samples to the control system on the data bus, are operations that are concurrently performed on each processing module.

In some embodiments, controlling the processing modules, with a control signal generated from a control system, to perform a data collection cycle comprises generating a control token by the control system, passing the control token to each processing module in sequence, wherein each processing module commences the respective data collection process after receiving the control token, and then passes the control token to a next successive processing module when the data output operation of the processing module is completed, irrespective of whether the digital sampling operation is complete.

In some embodiments, the method further comprises the control system generating a control command on a shared control bus, which is addressed to one or more of the processing modules connected to the shared control bus, to dynamically adjust at least one operating parameter of the one or more processing modules.

In some embodiments, a system comprises a control system, a plurality of processing modules, and a wire bundle connecting the control system to the plurality of processing modules, wherein the wire bundle comprises control lines and data lines. Each processing module is coupled to a respective set of sensors, wherein the sensors are configured to capture signals. The control system is configured to generate a control signal on the control lines to initiate a data collection cycle by the plurality of processing modules. In response to the control signal, each processing module of the plurality of processing modules is configured to perform a respective data collection process which comprises (i) capturing and processing a signal on each enabled sensor in the respective set of sensors of the processing module to generate a data sample for each signal captured on each enabled sensor, and (ii) outputting data samples to the control system on the data lines.

In some embodiments, the data samples output on the data lines comprise a multiplexed analog signal.

In some embodiments, one or more of the sensors comprises a sense electrode and wherein the corresponding physiological signal comprises an electrophysiological signal.

In some embodiments, one or more of the sensors comprises one of a sense electrode, an accelerometer, a force sensor, a tactile sensor, a strain sensor, a temperature sensor, a magnetic sensor, a fluid analyte sensor, and a flow sensor.

In some embodiments, a catheter comprises a control system, a plurality of processing modules, a plurality of sensors, wherein subsets of the plurality of sensors are connected to respective processing modules, wherein each sensor is configured to capture physiological signals generated in biological tissue, and a wire bundle connecting the control system to the plurality of processing modules. The catheter is structurally configured as an elongate structure, arranged with a distal end adapted for placement into a subject, and a proximal end structurally configured as a handle which is configured to interface with an operator. The plurality of sensors and processing modules are arranged at the distal end of the catheter, with the sensors configured and arranged to interface with said biologic tissues. The control system is disposed at the proximal end of the catheter.

In some embodiments, a ratio of sensors to wires is greater than one of a ratio of 1.5:1, a ratio of 2:1, a ratio of 4:1, a ratio of 16:1, a ratio of 64:1, and a ratio of 128:1.

In some embodiments, a ratio of sensors to processing modules is greater than or equal to one of a ratio of 2:1, a ratio of 4:1, a ratio of 8:1, a ratio of 16:1, and a ratio of 32:1.

In some embodiments, the catheter further comprises one or more of stimulation electrodes or one or more of therapeutic effectors, wherein the physiological signals captured by the sense electrodes are related to actions of the stimulation electrodes or therapeutic effectors on the biologic tissue during operation.

In some embodiments, the wire bundle comprises control lines and data lines, wherein the control system is configured to initialize and adapt functionalities of the processing modules via the control lines, and wherein the processing modules are configured to generate samples from the sensors and communicate the samples to the control system via the data lines.

In some embodiments, communication over the control lines is implemented using a bi-directional 2-wire bus, and wherein communication over the data lines is implemented using a high-speed 2-wire differential bus.

In some embodiments, communication over the control lines and the data lines is asynchronous such that the control system can change the functionalities of the processing modules by issuing control commands on the control bus without interrupting the communication of samples on the data lines by the processing modules.

In some embodiments, a collective sample rate of the processing modules is substantially independent of a number of sensors enabled by the processing modules during use.

In some embodiments, the handle comprises a power source and wireless transceiver, both coupled to the control system, wherein the wireless transceiver is configured to communicate between the control system and a remote host during use.

In some embodiments, the handle is operationally removable from and attachable to the catheter.

Other embodiments of the invention will be described in the following detailed description of embodiments, which is to be read in conjunction with the accompanying figures.

BRIEF DESCRIPTION OF THE DRAWINGS

FIGS. 2A, 2B, 2C, and 2D schematically illustrate sensing electrodes which can be implemented in a sensing tip of a catheter device as shown in FIG. 1A, according to embodiments of the invention.

FIG. 4 schematically illustrates a system which is integrated within a medical device to capture and process physiological signals, according to another embodiment of the invention.

FIG. 5 is a high-level system block diagram which illustrates a system configuration of circuit modules of a chipset, according to an embodiment of the invention.

FIGS. 7A, 7B, and 7C illustrate exemplary command sequences that can be used to read data from and write data to registers according to an embodiment of the invention in which an I$^2$C bus communication protocol is implemented.

FIG. 11 is a timing diagram which illustrates waveforms of token signals and control signals that are generated over a plurality of successive data acquisition cycles of the data acquisition system of FIG. 10 for a given chipset, according to an embodiment of the invention.

DETAILED DESCRIPTION

Figure 1A:
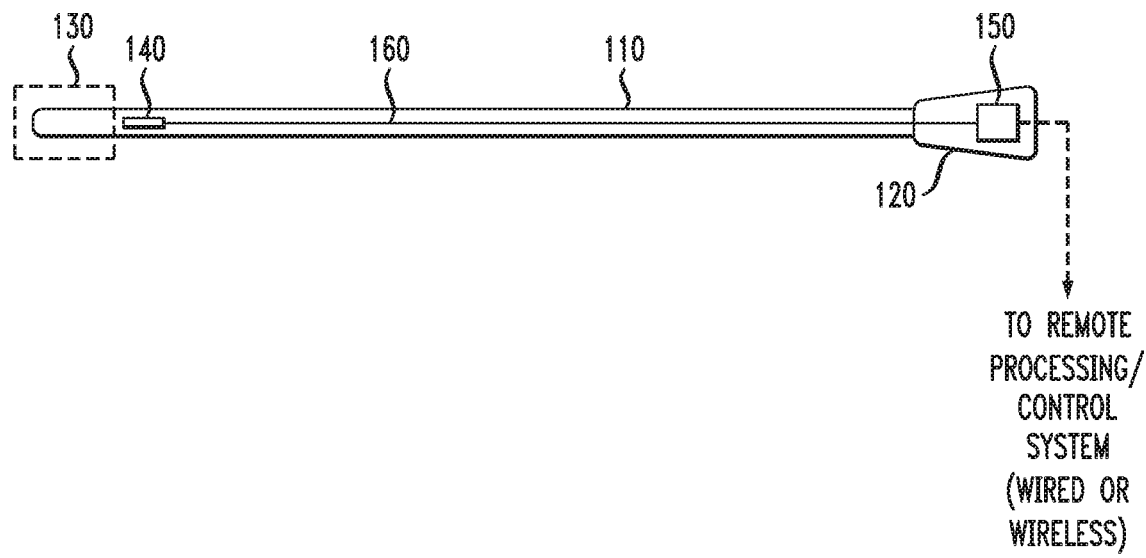
FIG. 1A is a high-level schematic illustration of a catheter device comprising circuitry which is configured to capture and process physiological signals, according to an embodiment of the invention.

Embodiments of the invention will now be described in further detail with regard to medical devices, such as catheters, which are configured to acquire and process physiological signals, such as electrophysiological (EP) signals (and other types of sensor signals), as well as methods for acquiring and processing physiological signals (and other types of sensor signals). It is to be understood that the same or similar reference numbers are used throughout the drawings to denote the same or similar features, elements, or structures, and thus, a detailed explanation of the same or similar features, elements, or structures will not be repeated for each of the drawings.

Generally speaking, an electrophysiological signal may be related to one or more of water concentration, tone, evoked potential, remote stimulation of nervous activity, an electromyographic signal (EMG), cardiac muscle electromyographic signals, smooth muscle myographic signals, a mechanomyographic signal (MMG), a local field potential, an electroacoustic event, local vasodilation, vessel wall stiffness, muscle sympathetic nerve activity (MSNA), central sympathetic drive (e.g. bursts per minute, bursts per heartbeat, etc.), tissue tone, action potentials from nearby nerves, nerve traffic (e.g. post ganglionic nerve traffic in the peroneal nerve, celiac ganglion, superior mesenteric ganglion, aorticorenal ganglion, renal ganglion, and/or related nervous system structures), vessel wall movement, spasm, combinations thereof, or the like.

Electrophysiological signals may include a spread of signal contributions from spatially local sources, such as nearby nerve traffic or traffic from adjacent tissues, through to long-range or remote traffic such as electrocardiographic signals, local field potentials, electroencephalograms, nearby muscle activity, or the like. Such signals may have a considerably large range of amplitudes as well as frequency content, with some low frequency (i.e. <10 Hz, <1 Hz, etc.), and ultra-low frequency content (i.e. <0.1 Hz, <0.01 Hz, etc.) being combined with intermediate frequency content (i.e. 10-100 Hz, 1-300 Hz, etc.), along with high frequency content (i.e. >300 Hz, >500 Hz, >1 kHz, etc.). Such content may be present with a large spread in amplitude, including large amplitude signal content (i.e. with signals greater than 2 mV, greater than 5 mV, etc.), intermediate amplitude signal content (i.e. with signals between 100 uV-1 mV, between 10 uV-2 mV, etc.), and/or small amplitude signal content (i.e. with signal amplitudes less than 100 uV, less than 50 uV, less than 20 uV, less than 10 uV, etc.).

The exemplary systems for capturing and processing physiological signals as described herein may be suitable for obtaining such diverse electrophysiological signal content with great efficiency and spatial precision. Such advantages are discussed throughout this application.

In some embodiments, the systems for capturing and processing physiological signals as described herein may be suitable for measuring physiological signals from a subject, wherein a physiological signal comprises any type of signal that is produced by a physiological process of a human being. In such cases, a sensing electrode may be effectively replaced with a sensing tip or sensor, the sensing tip or sensor configured to interface with the local anatomy of a subject during use to measure one or more physiologic signals therefrom. In some non-limiting examples, one or more of the sensing tips or sensors may include one or more electrodes, a needle electrode, a force sensor, mechanomyographic (MMG) sensing element, a vibration sensor, a strain sensor, a pressure sensor, a compliance sensor, a temperature sensor, combinations thereof, or the like each in accordance with the present disclosure. In embodiments of signal processing systems discussed herein, one or more sensing tips may be electrically coupled with one or more micro circuitry elements which are configured to condition the signals derived from the sensors as described herein.

In some non-limiting embodiments, one or more sensors in accordance with the present disclosure may be configured to access, monitor, and/or to treat one or more sensory receptors within a subject: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. In such cases, the signals obtained may be chemical, mechanical, electrical in nature, or the like, the associated sensors configured so as to generate a signal related to the physiological activity, wherein the signal is conditioned using micro circuitry as described herein.

In some non-limiting examples, sensor tips may be implemented with one or more types of sensors for multimodal signal acquisition including, but not limited to, temperature sensors, pressure sensors, photodetectors, ultrasound sensors, tactile sensors, contact sensors, electrodes (essentially any type), current sensors, accelerometers, piezo sensors (for acceleromyographs), force sensing elements (for wall contact analysis and control), strain sensing elements, electrochemical sensors, analyte level sensors, analyte detectors, bio-impedance sensors, magnetic contactless proximity sensors, etc. In multimodal signal acquisition and processing applications, the micro circuitry can be configured and arranged such that every signal input can be monitored on a separate channel, in parallel, coupled to a controller via one or more micro circuits, thereby allowing many different types of sensory input to be captured and processed through a unified and simplified (as well as fully wireless) high fidelity interface.

In some non-limiting applications, one or more of the sensors, may be configured to sense a variety of different types of data, such as but not limited to: electrical conductivity data, electrical potential data, pressure data, volume data, dimension data, temperature data, oxygen or carbon dioxide concentration data, hematocrit data, pH data, chemical data, blood flow rate data, thermal conductivity data, optical property data, cross-sectional area data, change in structure data, viscosity data, radiation data, monitoring an actuation process, magnetic field indictors, and the like. Alternatively or in combination, the system may be configured to include one or therapeutic and/or diagnostic effectors for actuation or intervention, such as providing an electrical current or voltage, setting an electrical potential, providing a calibration signal, a test stimulation, a catheter tip localizing current, heating a substance or area, inducing a pressure change, releasing or capturing a material, emitting light, emitting sonic or ultrasound energy, emitting radiation, orienting a tip, pushing against a surface, opening/closing a fluid channel, releasing a coil, and/or the like.

As explained in further detail below, embodiments of the invention as discussed herein are designed to provide various advantages over conventional medical devices (e.g., catheters) and associated techniques for capturing and processing physiological signals and other types of sensor signals for medical analysis. For example, as noted above, conventional catheter devices are essentially interconnect devices that transfer physiological signals, which are captured by the sensing electrodes at the distal end of the catheter, along a wire bundle that extends through the catheter body to a connector at the proximal end of the catheter body. Such conventional designs are problematic on various levels. For example, such designs introduce a large amount of electromagnetic interference (EMI), and other signal anomalies due to, e.g., variable loading, lead in-balance, movement artifacts, and capacitive loading to the target tissues. Moreover, the amount of wires that are included in the wire bundle that passes through the catheter body can be in the range of hundreds of wires depending on the application, which introduces structural constraints that can make catheter fabrication difficult and costly, and result in low yield due to potential wire failure and breakage during fabrication or use of the catheter device.

Furthermore, variations in electrode-tissue impedance cannot be readily addressed using conventional medical devices and signal capturing techniques. Indeed, electrode-tissue impedances must be below certain levels and matched to within certain levels between electrodes so as to provide an essentially balanced configuration, otherwise the imbalance essentially converts a common mode input to a differential mode input if any current is drawn by the wires due to line capacitance. In this regard, an impedance mismatch between wires of a wire-pair together with high electrode-tissue impedance, makes it challenging in practice to remove common mode signals from the desired differential signals, especially with EMI and other signal anomalies present on the wires extending through the catheter body. Embodiments of the invention as discussed herein provide solutions for these issues.

FIG. 1A is a high-level schematic illustration of a medical device 100 which comprises circuitry that is configured to capture and process physiological signals, according to an embodiment of the invention. In an embodiment, the medical device 100 is a catheter device which comprises a catheter body 110 (or guidewire), which comprises an elongated, thin flexible hollow tube, a torquer device 120 disposed at a proximal end of the catheter body 110, and at least one sensing tip 130 disposed at a distal end of the catheter body 110. The sensing tip 130 comprises a plurality of sensing electrodes (e.g., electrode arrays) which are configured to sense physiological signals from biological tissue in contact with, or in proximity to, the sensing electrodes. In another embodiment, the torquer device 120 is replaced by a handle at the proximal end of the catheter body 110, wherein the handle is configured to interface with an operator (e.g., allow the operator to hold the medial device 100). Example embodiments of sensing electrodes which can be implemented in the sensing tip 130 will be discussed below with reference to FIGS. 2A, 2B, 2C, and 2D.

The medical device 100 further comprises micro circuitry 140, control circuitry 150, and a wire bundle 160 (e.g., wire harness) connecting the micro circuitry 140 and the control circuitry 150. The micro circuitry 140 is disposed within the catheter body 110 in proximity to the sensing tip 130 and connected to the sensing electrodes in the sensing tip 130. The control circuitry 150 may be disposed within the torquer device 120 at the proximal end of the catheter body 110. The wire bundle 160 comprises electrical wires that supply DC power to the micro circuitry 140 and electrical wires that implement a control bus and data bus to transmit control signals and data signals between the micro circuitry 140 and the control circuitry 150.

The micro circuitry 140 comprises various types of analog and digital circuitry, such as analog amplifiers, multiplexers, analog-to-digital conversion (ADC) circuitry, data encoding and transmitter circuitry, etc. As explained in further detail below, the micro circuitry 140 is configured to acquire and sample analog signals (e.g., electrophysiological signals) that are sensed by the sensing tip 130, and then encode and transmit the sampled data to the control circuitry 150 over high-speed data lines of the wire bundle 160. In general, the micro circuitry 140 may be arranged within a distance of the sensing tip(s) 130 so as to manage the electrical properties of the interconnections there between. Some non-limiting distances are less than 200 mm, less than 100 mm, less than 50 mm, less than 25 mm, or the like.

The control circuitry 150 is configured to control data acquisition operations and configuration settings of the micro circuitry 140 by sending one or more control signals over the control bus lines included in the wire bundle 160. The control circuitry 150 is configured to collect and process the sampled data received from the micro circuitry 140, and then transmit the data to a remote computing system or station for further processing, analysis, display, etc., via a wired or wireless connection.

In one embodiment, the torquer device 120 comprises a "smart torquer" device which is configured to engage an elongated medical device (such as a catheter device or a guide wire device, etc.), and which allows a human operator to more precisely control movement of the device and the distal end thereof, e.g., as it moves through a cardiovascular system. The torque device 120 is deemed "smart" to the extent that the torquer device 120 is configured to control the micro circuitry 140, receive data from a source, e.g., the micro circuitry 140, then output the received data, e.g., to a user, a second device, etc., where the smart torquer may or may not be further configured to process the received data in some manner prior to outputting the data. This "smart" ability to receive and output data, e.g., with or without processing, may be implemented in a variety of different hardware and/or software components, e.g., using techniques such as those disclosed in PCT Application Serial No. PCT/US2016/052909, filed on Sep. 21, 2016 and entitled "Smart Torquer and Methods of Using Same," which is incorporated herein by reference. The torquer device 120 may include a power source, a wireless transceiver, and the like, to enable fully wireless operation of the catheter 100 during use.

In another embodiment, the torquer device 120 may be detachably connectable to the catheter body 110, wherein the torquer device 120 would comprise an interface mechanism to detachably connect the wire bundle 160 to the control circuitry 150. Such an embodiment may be advantageous for providing a reusable torquer device 120 along with a disposable catheter 100. In addition, the detachability of the torquer device 120 from the catheter body 110 would allow the torquer device 120 to be removed during a medical procedure to slide one or more devices over the catheter body 110, in the case that the catheter body 110 is being used as a guidewire or in combination with some other type of medical device that must be disposed coaxially with the catheter body 110 during a medical procedure.

An advantage of the catheter device 100 design of FIG. 1, as well as other medical devices that are designed and configured using signal capturing and processing techniques as discussed herein, is that the wire bundle 160 is simplified with a limited number of wires. This allows an axial connector to be utilized to couple the catheter body 110 to the torquer device 120. In this embodiment, when the torquer device 120 is removed, the catheter body 110 is of a uniform diameter along the entire length from the proximal to the distal end thereof. This uniformity allows another medical device (e.g., a therapeutic device or rapid exchange device) to be readily threaded over the catheter body 110, and then the torquer device 120 can be reconnected to the catheter body 110 so that the control circuitry 150 can begin communicating with the micro circuitry 140, and allow for mechanical manipulation of the medical device during a medical procedure.

In yet another embodiment, the control circuitry 150 may be embedded into a handle of the catheter 100. In such an embodiment, the handle may include one or more interconnects to couple other therapeutic or sensing devices into the signal processing system of the catheter device 100. The handle may include a power source, transceivers, or a connector for wired connection to an off-body device.

Figure 1B:
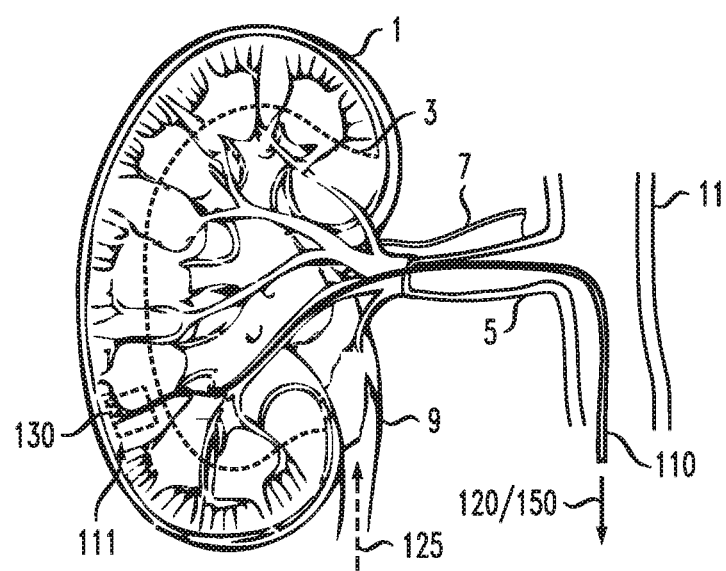
FIG. 1B illustrates a method of using the catheter device of FIG. 1A for analyzing physiological activity within an organ, according to an embodiment of the invention.

FIG. 1B illustrates a method of using the medical device 100 for analyzing physiological activity within an organ, according to an embodiment of the invention. As shown in FIG. 1B, the elongated catheter body 110 of the medical device 100 is shown placed within an organ 1 (such as a kidney) of a body, with the sensing tip 130 positioned within a region 3 (i.e. in this case the renal cortex 3) of the organ 1. A volume 111 defined in the vicinity of the sensing tip 130 may be coupled with the one or more sensors within the sensing tip 130 during a procedure (e.g. for purposes of monitoring, stimulating, treating, ablating, delivering a substance to, etc. tissues in the vicinity of the volume 111). The elongated catheter body 110 has been inserted endovascularly, percutaneously, etc. into a lumen in the body (e.g. a femoral artery, a femoral vein, a radial artery or vein, abdominal cavity, vertebral foramen, etc.) and directed to the monitoring site within the organ 1 as shown. In the FIG. 1B example, the elongated catheter body 110 has been directed along the renal artery 5 (alternatively along a renal vein 7 or a ureter 9, via an aorta 11, a radial access site, a femoral access site, or the like, etc.) such that the sensing tip 130 at the distal end of the elongated catheter body 110 is placed in intimate contact with one or more electroactive anatomical sites there within. In aspects, the elongated catheter body 110 may be placed such that the sensing tip 130 is oriented within the lumen of a vessel (e.g. an artery, a vein, a ureter, a renal artery, etc.) for obtaining physiologic information therefrom. An alternative access point 125 is shown in FIG. 1B along the ureter 9, which would provide access to the pelvic wall. In such a situation, the elongated catheter body 110 may be delivered such that one or more sensors located in the sensing tip 130 thereof may interface with the pelvic wall, thus monitoring one or more activities associated with the sensory receptors (i.e. renal nerves) located therein.

The medical device 100 can be utilized for accessing a parenchyma of an organ to measure EP activity, or otherwise be utilized for measuring EP activity in vessels within a body (e.g. within arteries, veins, a ureter, a urethra, etc.), for accessing a miniature lumen within the body, etc. A diagnostic method for diagnosing a medical condition involves accessing the parenchyma of an organ by coupling a sensing tip 130 of the medical device 100 to one or more anatomical sites within the parenchyma of an organ, so as to measure one or more physiologic signals therefrom. The sensing tip 130 and the micro circuitry 140 operate to capture and process physiologic signals from the parenchyma of the organ, wherein the captured physiologic signals are monitored to identify a trend in the physiologic signal (e.g. during rest, before, during and/or after a procedure, during a stimulation event, during a stress test, etc.), and/or make a diagnosis or prognosis based upon the recorded signal (e.g. a diagnosis of a disease state associated with local physiologic activity in the parenchyma of the organ, making a prognosis relating to an outcome of a disease state associated with activity in the parenchyma of the organ, etc.).

FIGS. 2A, 2B, 2C, and 2D schematically illustrate arrangements of electrode arrays which can be implemented in a sensing tip of a catheter device as shown in FIG. 1A, according to embodiments of the invention. While described below primarily in the context of sensing electrode arrays, an electrode array may more generally include any desired combination of sensing electrodes, stimulating electrodes, or other types of sensors, actuators, etc., including different types of electrodes, sensors, actuators, etc. Although various embodiments are described below with reference to obtaining and processing information from sensing electrodes or sense electrodes, it is to be appreciated that embodiments may more generally be applied to obtaining or processing information from any combination of sensors, actuators, sensing and/or stimulation electrodes, etc. Sense electrodes should thus be considered examples of what are more generally referred to herein as sensors.

In particular, FIGS. 2A, 2B, 2C, and 2D schematically illustrate embodiments of flexible multi-electrode sensing tips 201A, 201B, and 221. FIG. 2A shows monolithic sensing tips 201A and 201B including one or more respective tines 203A and 203B, wherein each tine comprises one or more sensors and/or microelectrodes 205A and 205B, respectively, and wherein each microelectrode 205A and 205B is configured to interface with an anatomical site of interest within a body. The sensing tips 201A and 201B may be at least partially formed from flexible substrates 207A and 207B, respectively, which are configured and dimensioned to form tines as well as provide electrical interconnection of components placed there upon, or integrated into the substrates 207A and 207B.

In aspects, the substrates 207A and 207B may comprise a flexible polymer, polyimide, PET, PEN, an elastic material, polyurethane, a silicone, an elastomer, an electroactive polymer, or the like known in the field of flexible electronics. In aspects, the sensing tips 201A and 201B may include one or more respective microcircuits 211A and 211B in accordance with the present disclosure. The microcircuits 211A and 211B may be configured to perform one or more functions such as signal routing, multiplexing, demultiplexing, preamplification, signal amplification, filtering processes, differential coupling to a reference electrode, signal conditioning function, analog to digital conversion, communication, power management, combinations thereof, and the like. The substrates 207A and 207B may include one or more respective conducting traces 209A and 209B that are disposed and positioned to interconnect the sensors and/or electrodes 205A and 205B with the respective microcircuits 211A and 211B. In aspects, one or more of the conducting traces 209A and 209B may comprise a metal, a meandering metal trace (i.e. so as to improve the flexibility or stretch capability thereof), an organic conductor, a printed structure, a physically deposited structure, or the like.

In aspects, one or more microelectrodes 205B may be formed at the extreme tip of a tine 203B. Such formation may be achieved by routing one or more traces 209B to the tip and severing the tip so as to expose only the most distal part of the trace 209B so as to form the interconnect for the microelectrode 205B. The interconnect may be plated with an interfacing material, such as a metal, platinum, a composite, a conjugated polymer, etc. so as to form the microelectrode 205B and so as to enhance coupling between the microelectrode 205B and a surrounding anatomical site of interest.

The substrates 207A and 207B may include interconnects for coupling with power and signal lead wires 213A and 213B. The microcircuits 211A and 211B may be configured to communicate with an outside communication module, a controller, or the like (not explicitly shown). In aspects, communication may be in the form of a bus protocol such as I$^2$C, 1-wire, SPI, serial, etc. In aspects, the lead wires 213A and 213B may be configured and interconnected to power management hardware configured so as to provide power and signal communication along the same leads. Such a configuration is advantageous to minimize the number of lead wires 213A and 213B within the catheter.

After attachment of components (e.g. sensors, microcircuit(s) 211A and 211B, lead wires 213A and 213B, etc.) the substrates 207A and 207B may be arranged (i.e. in this non-limiting example, rolled 215) to form a completed sensing tip 217. FIG. 2B shows a completed sensing tip 217 with an integrated jacket 219 coupled to the tip so as to reinforce the electrical interconnection of the substrates 207A and 207B, the lead wires 213A and 213B, and/or the microcircuits 211A and 211B. In aspects, the jacket 219 may also provide increased electrical isolation between the microcircuits 211A and 211B, and the respective traces 209A and 209B, lead wire interconnects 207A and 207B, and the surroundings.

FIG. 2C illustrates a non-limiting example of a sensing tip 221 with deployable tines 203. The tines 203 may be deployed from within a jacket 223 by retraction 225 of the jacket 223, advancement 227 of the tines 203 or a combination thereof. As shown in FIG. 2C, the tines 203 are exposed to the left of the image during a retraction 225 of the jacket 223, or an advancement 227 of the tines 203. Such action will lead to deployment of the tines 203 so as to monitor a physiologic parameter during a procedure.

Two non-limiting examples of deployed configurations are shown in FIG. 2C. In one example of a deployed configuration, the tips of the tines 203 are free and the set shape of the tines 203 results in a flower like formation upon deployment from the jacket 223. In aspects, interconnects 231 on the substrate 207 may be dimensioned and/or encapsulated so as to form a soft seal against the jacket 223. Such a configuration may be advantageous to minimize fluid ingress to the catheter during a procedure. The tines 203, via lead wires connected thereto, are coupled to a controller 150 optionally included in a torquer device, as discussed above with respect to FIG. 1A.

Another example of a deployed configuration is shown in FIG. 2C, where the tips of the tines 203 are held together with a restraining tip 235 so as to form a basket shape upon deployment 225. The basket may be retained in a jacket 239 of the device before deployment 225. In aspects, the restraining tip 235 may include an additional pull wire 232 configured such that relative movement of the pull wire 232 may provide the forces necessary to deploy 225 the tines 203 (i.e. to convert the tines 203 from a collapsed shape to a basket-like shape).

In aspects, one or more of the tines 203 may be coupled with a microcircuit 237 in accordance with the present disclosure. The microcircuit 237 may be embedded into the device substantially near to the tines 203, within 200 mm thereof, 100 mm thereof, within 20 mm thereof, within 5 mm thereof, etc.

FIG. 2D illustrates a close up view of a tine 203 in accordance with the present disclosure. The tine 203 includes a plurality of electrodes 205 arranged along the tine 203 with a predetermined spacing 242. The tine 203 is constructed with a predetermined width 241, which may be tapered and/or otherwise shaped along the length of the tine 203. The tine 203 may include one or more traces 209 to interconnect the electrodes 205 with one or more microcircuits. The tine 203 may be generally constructed from a substrate 207 in accordance with the present disclosure. In aspects, the substrate 207 may be constructed from a laminate composite structure, including a base substrate, the traces, overcoats, etc. In aspects, the electrodes 205 may be configured so as to extend beyond the height of the substrate 207 such as by forming the electrodes 205 as bumps, generating whisker like features on the electrodes 205, plating the electrodes 205, etc.

It is to be understood that the illustrative embodiments discussed above with reference to FIGS. 1A-1B, and 2A-2D are non-limiting example embodiments of medical devices and medical procedures that can be implemented using systems and methods as discussed herein to acquire and process physiological signals (e.g., EP signals) and other types of sensor signals, as well as methods for acquiring and processing physiological signals (e.g., EP signals) and other types of sensor signals. For example, while the example embodiment of FIG. 1A is discussed in the context of a catheter device, the sensor signal acquisition and processing techniques discussed herein can be implemented using various types of elongated medical devices such endoscopes, guidewires, and other similar elongated medical devices and tools.

Furthermore, the sensor signal acquisition and processing circuitry discussed herein can be implemented as components of a sub-assembly or be components of a dedicated device such as in a guidewire, a catheter, a surgical tool, etc. By way of example, the sensor signal acquisition and processing circuitry discussed herein may comprise a sensing sub-assembly that is integrated into a cardiac ablation catheter. Since the sensor signal acquisition and processing circuitry has an extremely small footprint and is adjustable, a therapeutic catheter would have a significant amount of room available for the orientation mechanisms and therapeutic delivery elements (wiring, ablation electrodes), etc.

In addition, such medical devices would be small enough to access smaller vessels, and be more flexible and maneuverable, etc. For example, the sensor signal acquisition and processing circuitry discussed herein can be implemented as components of a guidewire device, with a body that is small enough in diameter that a therapeutic device may be slid over the body of the guidewire to a treatment site, with the sensing tip further along the target vasculature so as to monitor the target organs, therapy, completion of therapy, etc.

While the example embodiment of FIG. 1B is discussed in the context of using a medical device (e.g., a catheter device) for inter parenchymal monitoring, monitoring at sites between organs, etc., it is to be understood that the sensor signal acquisition and processing circuitry discussed herein can be implemented in conjunction with other systems including, but not limited to, stimulating electrodes, ablation electrodes, or other types of therapeutic configurations, to thereby implement fast diagnostic, and confirmative therapy based medical devices. In addition, the sensor signal acquisition and processing systems and methods discussed herein can be readily applied in other medical diagnostic and therapeutic applications such as cardiology, atrial mapping, coronary mapping, central nervous system applications, and pulmonary applications, etc.

It is to be appreciated that the sensing tips shown in FIGS. 2A, 2B, 2C, and 2D are presented by way of example only, and that embodiments are not limited solely to use with the particular sensing tip configurations shown. More generally, embodiments include various other types of sensing tips having multiple electrodes or other sensors that are coupled to micro circuitry providing processing of EP signals monitored using such electrodes or other sensors as described herein. Furthermore, while example embodiments are discussed herein in the context of signal acquisition and processing circuitry having sensing tips with sensing electrodes for sensing EP signals, it is to be understood that other types of sensors and associated applications can be implemented using the signal acquisition and processing techniques discussed herein.

For example, in addition to sensing electrodes for EP signals, sensor tips can be implemented with different types of sensors for multimodal signal acquisition including, but not limited to, temperature sensors, pressure sensors, electrodes (essentially any type), current sensors, accelerometers, piezo sensors (for acceleromyographs), force sensing elements (for wall contact analysis and control), strain sensing elements, electrochemical sensors, bio-impedance sensors, magnetic contactless proximity sensors, etc. In multimodal signal acquisition and processing applications, the micro circuitry can be configured and arranged such that every signal input can be monitored on a separate channel, in parallel, thereby allowing many different types of sensory input to be captured and processed through a unified and simplified (as well as fully wireless) high fidelity interface.

Figure 3A:
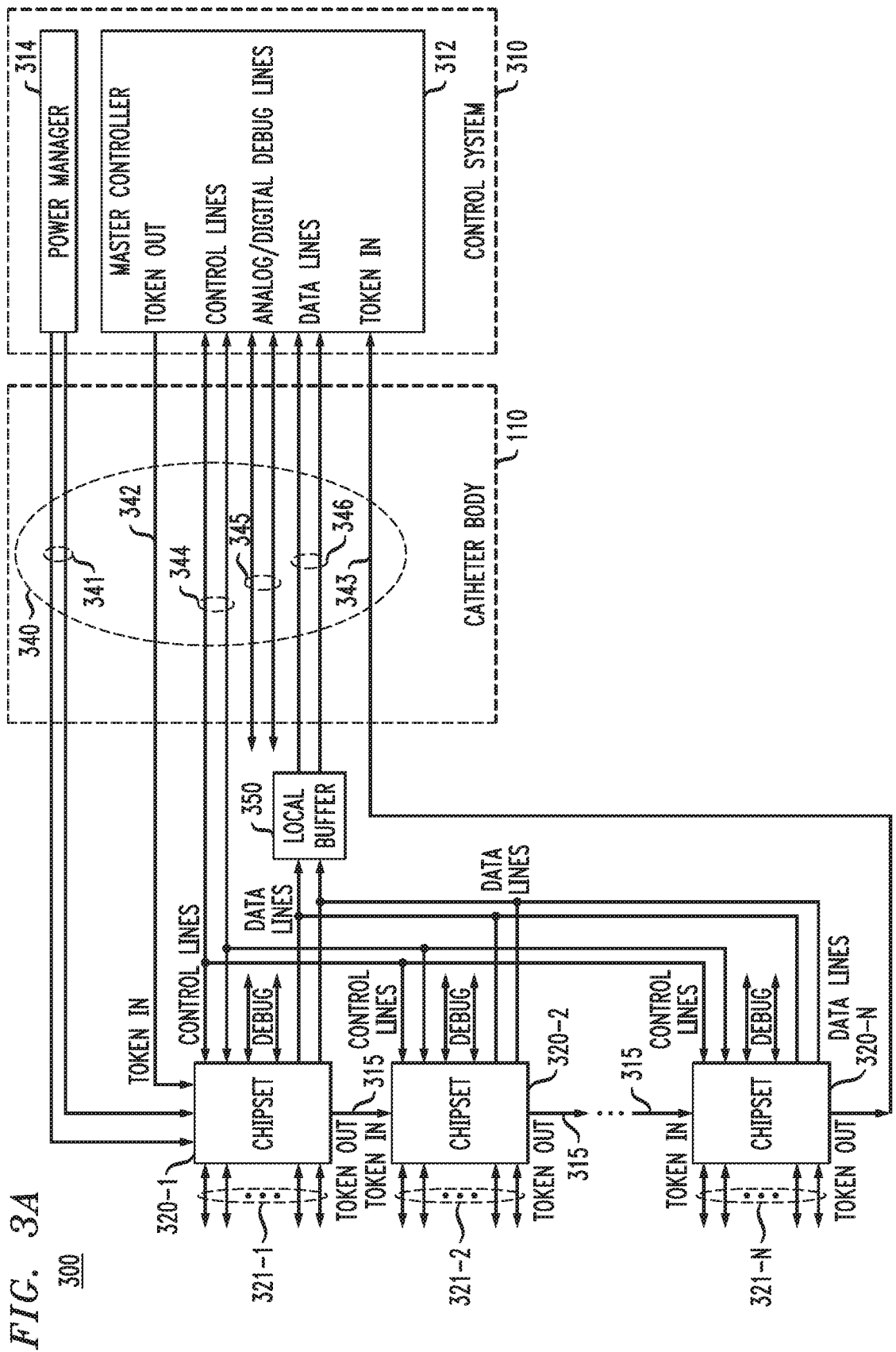
FIG. 3A schematically illustrates a system which is integrated within a medical device to capture and process physiological signals, according to an embodiment of the invention.

FIG. 3A schematically illustrates a system 300 which is integrated within a medical device to capture and process physiological signals, according to an embodiment of the invention. The system 300 comprises a control system 310 and a plurality of chipsets 320-1, 320-2, . . . , 320-N (collectively referred to as chipsets 320, or each singularly referred to as a chipset 320). Each chipset 320-1, 320-2, . . . , 320-N comprises a set of input ports (or input pins) connected to a respective set of sense electrodes 321-1, 321-2, . . . , 321-N (collectively referred to as sense electrodes 321), one or more alternative types of sensors, and/or combinations thereof.

It is to be understood that the sense electrodes 321-1, 321-2, . . . , 321-N are one type of sensor that can be implemented in the systems described herein for capturing and processing physiological signals. In this regard, while FIG. 3A and other embodiments are described below with reference to sets of sense electrodes, it is to be appreciated that embodiments are not limited solely to use with sense electrodes but may more generally be used with various types of electrodes, sensors, etc., which are configured to capture/measure various types of physiological signals and other types of signals. Further, it is to be appreciated that one or more of the chipsets 320 may be configured for connection to different types of electrodes (e.g., with input ports or input pins configured for connection to sensing electrodes, stimulating electrodes, various types of sensors, etc.). Thus, the chipsets 320 are suited for applications involving multimodal sensing, in that one or more of the chipsets 320 may be coupled to electrodes or sensors of different types, or different chipsets 320 may be coupled to different types of electrodes or sensors. In some cases, a given one of the chipsets 320 may be coupled to different types of electrodes or sensors configured to capture different aspects or information related to monitored electrophysiological activity, stimulation or other therapeutic application, etc.

The control system 310 comprises a master controller 312 and a power manager module 314. The control system 310 is connected to the chipsets 320 via a wire bundle 340, wherein the wire bundle 340 comprises control lines and data lines including, for example, power supply and control lines 341, first and second token control lines 342 and 343, control bus lines 344 (or control bus 344), optional analog/ digital (A/D) debugging test lines 345 (which are utilized during product development, and possibly maintained and made part of the system for in-field debugging operations), and data bus lines 346 (or data bus 346). The system 300 further comprises an optional local buffer module 350 connected to the data bus 346.

In general, the system 300 comprises one or more chipsets 320, with each chipset 320 connected such that the control lines 344 (forming a control bus), and data lines 346 (forming a data bus) are available for setting one or more signal conditioning parameters or functional parameters on the chipset 320 during use, as well as to transmit the collected data to the control system 310 during use. Such a configuration is advantageous as it can be adaptively scaled to large numbers of sensors 321 with minimal increase in wiring 340 complexity, assembly complexity, and without overall changes in system architecture.

In general, the system 300 may include one or more control busses, wherein each control bus may be coupled to one or more chipsets 320 up to a maximum allowable number of chipsets 320 on the bus (i.e. up to 16 chipsets, up to 64 chipsets, up to 127 chipsets, etc.), the maximum allowable chipsets 320 on each control bus being dictated by one or more of the bus capacitance, the maximum number of allowable device addresses on the bus, the maximum amount of traffic that may reasonably be handled by the bus during use, a combination thereof, of the like. In applications where the number of chipsets 320 exceed the maximum number which may be handled by a particular bus, additional control busses may be added to the system. In that way, very few additional control lines are needed to manage systems with extremely high numbers of chipsets 320.

In general, the system 300 may include one or more data busses, wherein each data bus may be coupled to one or more chipsets 320 up to a maximum allowable number of chipsets 320 on the bus (i.e. up to 16 chipsets, up to 64 chipsets, up to 127 chipsets, etc.), wherein the maximum allowable chipsets 320 on each data bus is dictated by one or more of the bus capacitance, the maximum number of allowable device addresses on the bus, the maximum amount of traffic that may reasonably be handled by the bus during use, a combination thereof, of the like. In applications where the number of chipsets 320 exceeds the maximum number which may be handled by a particular bus, additional data busses may be added to the system. In that way, very few additional control lines are needed to manage systems with extremely large numbers of chipsets 320.

Alternatively, for applications the control and data busses may be shared (i.e. collected data passed back to the control system 310 on the same lines as are used by the control bus).

In the context of the high-level medical device 100 shown in FIG. 1A, the plurality of chipsets 320-1, 320-2, . . . , 320-N, and the local buffer 350 shown in FIG. 3A schematically depict an example embodiment of the micro circuitry 140 that is disposed at the distal end of the catheter body 110 in proximity to a sensing tip 130, wherein the sense electrodes 321-1, 321-2, . . . , 321-N for each chipset 320 are arranged in arrays in the vicinity of the sensing tip 130 of the medical device 100. In addition, the bundle of control/data wires 340 extend through the catheter body 110 to the control system 310 which, in some embodiments, is disposed within a torquer device 120 at the proximal end of the medical device 100.

In one non-limiting embodiment, the sense electrodes 321 can be formed/patterned on a flexible substrate, and the chipsets 320 are mounted to the flex circuit with input pins/ports of the chipsets 320 being coupled to the respective sense electrodes 321. The bundle of control/data wires 340 can be formed as part of a single wiring harness that passes through the catheter body 110, wherein one end of the wiring harness connects to the flexible substrate on which the sense electrodes 321 are formed and the chipsets 320 are mounted, while another end of the wiring harness is coupled to the control system 310. In one non-limiting application, the control/data/power wires 340 may be provided by a flexible circuit. In another non-limiting application, the entire system from the sensing tips 130 through to the catheter body 110, and optionally the control system 310 may be formed on a single flexible circuit.

In the example embodiment of FIG. 3A, each chipset 320-1, 320-2, . . . , 320-N is connected to the power control lines 341. The power manager module 314 is configured to supply DC power and power control signals to each chipset 320-1, 320-2, . . . , 320-N over the power control lines 341. In one embodiment, separate power control lines can be utilized to supply power to the analog and digital subsystems on the chipsets 320. In such instance, there would be more than the two (e.g., four) power control lines 341 shown in FIG. 3A. In addition, each chipset 320-1, 320-2, . . . , 320-N is connected to the A/D debugging control lines 345 to enable the master controller 312 to initiate analog and/or digital debugging operations on the chipsets 320 to detect and correct errors in the operations of the analog and/or digital circuitry of the chipsets 320. The A/D debugging operations can be implemented during development and testing of the system 300, and can be removed and not made part of the wire bundle 340 of the end product.

In general, the chipsets 320 communicate with the master controller 312 over two independent networks, which comprise the control bus 344, and the data bus 346. As shown in FIG. 3A, each chipset 320-1, 320-2, . . . , 320-N is connected to the control bus 344, wherein the control bus 344 is configured as a shared bi-directional control bus that allows the master controller 312 to communicate with each of the chipsets 320 (slave devices) to configure/control circuitry and operational modes of the chipsets 320 using control commands transmitted on the shared control bus 344. In some embodiments, each chipset 320 (slave device) is software-addressable on the control bus 344 by a unique address (referred to herein as Device ID address) which is assigned to the given chipset 320 by the master controller 312 using a token-based address assignment process, as described herein.

In addition, each chipset 320-1, 320-2, . . . , 320-N is connected to the data bus 346. In some embodiments, the data bus 346 is configured as a time-shared shared data bus which comprises a single pair of lines (e.g., data and clock line, or differential data lines, etc.) that allows the chipsets 320 to send data to the master controller 312 over the data bus 346. In the embodiment of FIG. 3A, each chipset 320 transmits a block of digital data to the master controller on the shared data bus 346, wherein each block of digital data comprises one or more digital samples of analog signals captured on each sense electrode of the respective set of sense electrode 321 of the chipset 320. In some embodiments, time-sharing of the data bus 346 for data output by the chipsets 320 is implemented using a token-based data output collection process, as described herein. The optional local data buffer module 350 can be implemented at some point along the shared data bus 346 in proximity to the output of the chipsets 320 to temporarily buffer data outputs of the chipsets 320 to control data flow on the shared data bus 346.

As further shown in the example embodiment of FIG. 3A, each chipset 320-1, 320-2, . . . , 320-N comprises a Token IN port and a Token OUT port. The first token control line 342 is connected to a Token OUT port of the master controller 312 and to the Token IN port of the chipset 320-1. The second token control line 343 is connected to the Token OUT port of the chipset 320-N and to a Token IN port of the master controller 312. The Token OUT port of each chipset 320-1, 320-2, . . . 320-(N–1) is connected (via a chip-to-chip control line 315) to a respective Token IN port of a next successive chipset, thereby forming a sequential chain of chipsets from the first chipset 320-1 to the last chipset 320-N.

As explained in further detail below, the sequence and timing of various operations performed by the chipsets 320-1, 320-2, . . . , 320-N are controlled using a token-based protocol in which a control token (e.g., "address assignment" token, "data output enable" token, etc.) is output on the first token control line 341 from the master controller 312 to the first chipset 320-1, and wherein the control token is passed downstream to each successive chipset 320 in the chipset chain via the chip-to-chip control lines 315. Each chipset 320 performs one or more operations when holding the control token, and when the operations are completed, the chipset 320 passes the control token to the next successive downstream chipset 320 to initiate the same operations in the downstream chipset 320. When the last chipset 320-N (holding the control token) completes the associated operations, the chipset 320-N will pass the control token back to the master controller 312 on the second token control line 343, which indicates to the master controller 312 that the current operation cycle is complete.

During general use, some token controlled operations include operations that are completed prior to passing control of the token to a next successive chipset 320 or to the master controller 312 (e.g., sending data on the data bus), while other operations may be performed in parallel irrespective of whether a particular chipset 320 is holding the token or not (e.g., collecting data samples from the sensor array 321 coupled to a particular chipset 320 in the system). Such time sharing and parallel operations optimize the overall throughput capability of the system in terms of maximizing the samples that can be collected by each chipset 320, and optimizing throughput of data on the data bus during operation.

During general use, the control bus 344 may operate asynchronously and independently from the token passage, data transmission, and sampling operations. Thus, the system 300 may be configured so as to change properties of one or more components of each chipset 320 on the fly during use. In one non-limiting example, the gains and DC offsets of a particular channel on a particular chipset 320 may be adjusted by the control bus and immediately loaded, such that the next sample collected from that channel includes the updated parameters. Such an approach may be advantageous for digitally assisting the signal chains in the chipsets 320 in real-time to optimize the fidelity of each channel as needed during use.

Figure 3B:
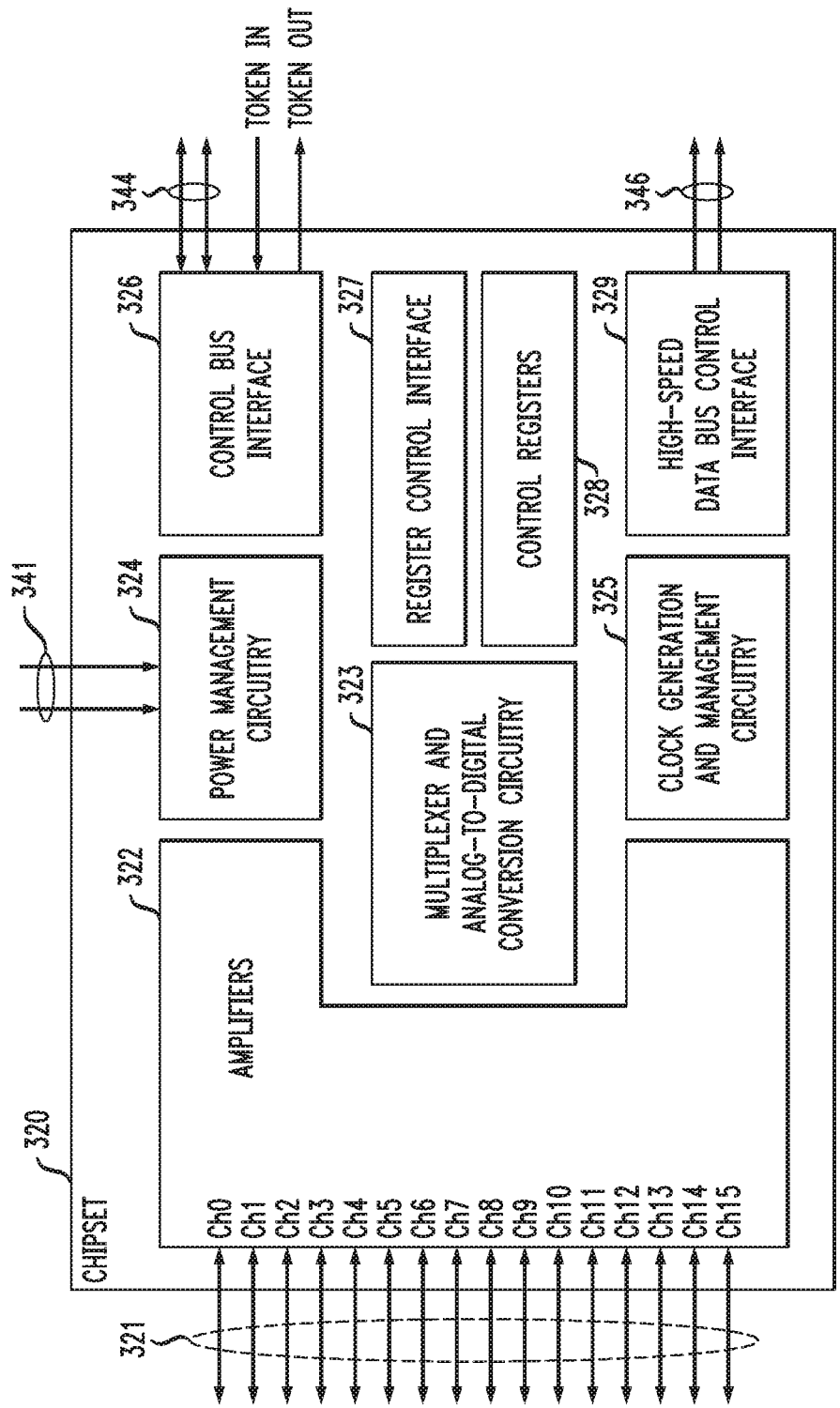
FIG. 3B schematically illustrates blocks of analog and digital circuitry which can be implemented in each chipset in the system of FIG. 3A, according to an embodiment of the invention.

FIG. 3B schematically illustrates blocks of analog and digital circuitry which can be implemented in each chipset 320 of FIG. 3A, according to an embodiment of the invention. As shown in FIG. 3B, the chipset 320 comprises amplifier circuitry 322, multiplexer and ADC circuitry 323, power management circuitry 324, clock generation and management circuitry 325, a control bus interface 326, a register control interface 327, a plurality of control registers 328, and a high-speed data bus control interface 329. The power management circuitry 324 is connected to the power control lines 341 and receives power control signals and DC supply power from the power manager 314. The control bus interface 326 is connected to the bidirectional control bus 344, the Token IN port, and the Token OUT port of the chipset 320. The high-speed data bus control interface 329 is connected to the shared data bus 346.

In some embodiments, each chipset 320 comprises a mixed-signal CMOS integrated circuit that comprises both analog circuitry (e.g., amplifiers), digital circuitry (e.g., control interfaces 326, 327, and 329), intrinsic mixed-signal circuits (e.g., ADC), and embedded software. In some embodiments, each chipset 320 may comprise a group of two or more interdependent microchips that are packaged together to collectively provide chipset functionalities described herein. For example, the amplifier circuitry 322 and multiplexer/ADC circuitry 323 may be integrated on a first microchip, while all other system components may be integrated on a second microchip, wherein the first and second microchips collectively form the chipset 320 shown in FIG. 3B. In the regard, the term "chipset" as used herein is meant to broadly refer to either a single die or multiple die implementation. Furthermore, the term "processing module" as used herein is meant to broadly refer to a set of integrated circuits that collectively perform an interdependent set of functions, wherein the set of integrated circuits can be integrated on a single die, or on two or more separate dies that are interconnected. In this regard, each chipset 320 shown in FIGS. 3A and 3B may be considered a "processing module" within the context of such term as used herein to discuss various embodiments and as used in the claims.

The amplifier circuitry 322 comprises multiple parallel channels of multistage amplifiers, wherein each amplifier channel is configured to amplify analog signals (e.g., EP signals) which are captured on a respective sense electrode in the set of sense electrodes 321. For example, in some embodiments such as shown in FIG. 3B, each chipset 320 comprise 16 signal channels (Ch0, Ch1, Ch2, Ch3, Ch4, Ch5, Ch6, Ch7, Ch8, Ch9, Ch10, Ch11, Ch12, Ch13, Ch14, and Ch15), wherein the amplifier circuity 322 would comprise 16 parallel channels of multistage amplifiers with the input to each channel of multistage amplifiers being coupled to a respective one of the 16 sense electrodes. The 16 amplifier channels would operate in parallel to amplify analog signals captured on the respective sense electrodes connected to the amplifier channel inputs. More specifically, is one embodiment, each amplifier channel comprises multiple amplifier stages which are configured to remove a common mode signal component of the input signals, remove 1/f noise, etc. and condition the input signals for sampling (e.g., filtering using anti-aliasing filters, etc.). It is to be understood that each chipset 320 can be configured with other suitable numbers of signal channels and sense electrodes (other than 16), and that the example embodiments discussed herein will be discussed in the context of 16 signal channels per chipset 320 solely for illustrative purposes.

The multiplexer and ADC circuitry 323 comprises a multiplexer circuit that selectively connects the output of each amplifier channel of the amplifier circuitry 322 to the input of an ADC circuit, wherein the ADC circuit is configured to digitize the amplified analog signals output from the amplifier channels of the amplifier circuity 322 to generate digital samples. The high-speed data bus control interface 329 encodes the digital samples and outputs the encoded digital samples on the data bus 346 for transmission to the master controller 312 for further processing. The control bus interface 326 receives and processes control commands received on the control bus 344 from the master controller 312, wherein the control commands are issued by the master controller 312 to read or write register data to the control registers 328. The register control interface 327 is utilized by the control bus interface 326 to control the reading/writing of register data from/to the control registers 328 in response to the control commands received by the control bus interface 326 from the master controller 312. The clock generation and management circuitry 326 is comprises clock generation circuity that is configured to generate clock signals for controlling clocking functions as needed for the various subsystems of the chipset 320.

The control registers 328 (FIG. 3B) of the chipset 320 are implemented as predefined memory locations in system memory or as register arrays in hardware registers, to store system configuration parameters. For example, the control registers 328 comprise registers to store configuration data to adjust signal channel parameters in each of the signal channels (e.g., signal channels Ch0~Ch15) such as amplifier gains, filter bandwidths, DC offset correction values for amplifier stages, DC offset correction values for sense electrodes, etc. The control registers 328 further comprise registers to store configuration data to adjust data sampling rates of the ADC circuitry and to adjust data encoding parameters and data output rates related to operations of the high-speed data bus control interface 329 when encoding and outputting data on the data bus 346. The control registers 328 further comprise registers to store channel enable control parameters to selectively enable or disable amplifier channels. The control registers 328 further comprise registers to store control data that is utilized by the power management circuity to control power (off/on, etc.) for each subsystem of the chipset 320, and registers to store control data that is used by the clock generation and management circuitry 325 to adjust the frequencies of clocks signals that are used to clock the various functions of the multiplexer/ADC circuitry 323 and high-speed data bus control interface 329, for example.

In other embodiments, additional amplifier circuity is implemented in the multiplexer/ADC circuitry 323. For example, a shared multistage amplifier can be implemented in the signal chain between the output of the multiplexer circuitry and the ADC circuitry. The shared multistage amplifier is configured to perform fast offset and gain corrections to boost signal gain further and keep the signal in a target range during a sample and hold (S/H) operation on the ADC circuitry. In this way, the output of the multiplexer circuitry can be further fine-tuned through more precise gain and offset adjustment for a single sample. This allows the system operation to be adjusted, on the fly, to boost the signal gain to very high levels to cancel out more of the common mode signal, and push the signal gain to extreme levels. For example, the signal gain can be boosted 100,000 times, which allows the system to hone in on signals near the noise floor (i.e. a small neural signal), while adjusting the DC offsets from sample to sample to keep a signal of interest in range during use.

As noted above, the chipsets 320 can asynchronously and concurrently communicate with the master controller 312 over two independent bus networks—the control bus 344 and the data bus 346. For example, while the chipsets 320 are transmitting data blocks of digital samples to the master controller 312 over the data bus, 346, the master controller 312 can also be communicating with the chipsets 320 over the control bus 344 to write configuration data to control registers to control/adjust the functionalities, in real-time, of the data acquisition, ADC sampling, encoding, and data output systems on the chipsets (e.g., adjust data sampling rates, data output rates, etc.).

In some embodiments, the control bus interface 326 and associated bus communication control functionality is implemented using a two-wire bus protocol, such as the known I$^2$C bus communication protocol, which enables bi-directional communication between a master device and one or more slave devices on a bus. In the context of the embodiments discussed herein, the master controller 312 is a bus master and the chipsets 320 are slave devices on the control bus 344. For the I$^2$C bus communication protocol, the control bus 344 would include a serial data (SDA) line and a serial clock (SCL) line, wherein one data bit is transferred on the SDA line during each clock pulse on the SCL line. A block of data bits (e.g., byte) transmitted on the SDA line of the control bus 344 may be a Device ID address, a register address, or configuration/control/status data that is either read from a control register on a given chipset, or configuration/control data that is to be written to a control register on a given chipset.

As in known in the art, the I$^2$C bus communication protocol utilizes, for both the SDA and SCL lines, an open-drain/open-collector with an input buffer on the same line, which allows a single data line to be used for bidirectional data flow. Open-drain refers to a type of output in which a pull-down field effect transistor (FET) can be activated to pull a SDA/SCL line down to a logic low level (e.g., ground), and then deactivated to "release" the SDA/SCL line and allow the SDA/SCL line to be pulled up to a logic high level (power rail) by a pull-up resistor. In this regard, in some embodiments, the control bus interface 326 would comprises SDA/SCL line driver circuitry (e.g., pull-down FET, pull-up resister, line buffer, control, etc.) for driving/controlling the control bus lines 344.

To enable communication on the control bus 344, each chipset 320 has a specific unique Device ID address to differentiate between other chipsets on the same control bus 344. In some embodiments, the Device ID address for a given chipset can be assigned using hardwired pins that are set to either high or low power rails. In some embodiments, the Device ID address for a given chipset can be hard-coded within the internal memory of the chipset (i.e. via a 1-time programming operation at the time of manufacture). In some embodiments, the Device ID addresses of the chipsets 320 are dynamically assigned to each chipset 320 using a token-based device address assignment protocol implemented by the master controller 312 and chipsets 320.

For example, in some embodiments, a token-based device address assignment protocol is commenced upon a system power-up or a system reset wherein each chipset 320 enters into an initialization state. In the initialization state, each chipset 320 starts with the same initial default Device ID address (e.g., 0x00). Each chipset 320 comprises logic to re-assign its Device ID address when the following criteria are met: (i) the current Device ID address of the chipset 320 is the default initial Device ID address (e.g., 0x00); and (ii) the chipset is holding an "address assignment" control token issued by the master controller 312. Following the power-up and stabilization of each chipset 320, a device address assignment process is performed as follows.

The master controller 312 outputs an "address assignment" token signal on the first token control line 342, which is input to the Token IN port of the first chipset 320-1. Under the conditions where the first chipset 320-1 is in an initialization state with default initial Device ID address (e.g., 0x00), and is holding the address assignment token, the first chipset 320-1 listens on the control bus 344 for an incoming new Device ID address sent from the master controller 312. When the new Device ID address is received from the master controller 312, the first chipset 320-1 will write the new Device ID address to the Device ID register of the chipset 320-1, and then assert control of the control bus 344 to confirm the new Device ID address back to the master controller 312. When the confirmation is complete, the first chipset 320-1 relinquishes control of the control bus 344, and then passes the address assignment token to the second chipset 320-2 on the control line 315 connecting the Token OUT port and Token IN port of the respective chipsets 320-1 and 320-2.

The address assignment and token passing process is then repeated by each successive chipset 320 in the chain of chipsets 320 until the address assignment token is returned to master controller 312 from the last chipset 320-N over the second token control line 343, at which time the master controller 312 will know that the Device ID address assignment process is complete. Once all Device ID addresses are assigned, the control bus 344 will be deemed fully configured, and the master controller 312 will utilize the newly assigned Device ID addresses to communicate with the chipsets 320 over the control bus 344.

If there is some failure that occurs during the address assignment process, in some embodiments, the master controller 312 may be configured to broadcast a "master reset" command on the control bus 344 to which all chipsets 320 respond irrespective of which chipset current holds the token, to reset the Device ID address to the default initial Device ID address (e.g., 0x00). In another embodiment, the master controller 312 may issue a "wipe token" command that clears the token and puts the entire system back into the ready state, etc.

In some embodiments, for an all-digital implementation as in the system 300 of FIG. 3A, the data bus 346 can be implemented using a single pair of wires (data and clock wires, or differential data lines, etc.) that pass through the catheter body 110. Each chipset 320 comprises ADC circuitry to digitize the analog signals captured on the sense electrode 321 and generate digital samples, as well as data encoding/output circuitry to digitally encode the digital samples for transmission as digital signals over the data bus 346. In some embodiments, the samples may be sent using a differential two-wire bus. In some embodiments, the high-speed data bus control interface 329 (FIG. 3B) and associated data bus control functionality is implemented using a 2-wire, time-shared, high-speed Manchester-encoded low voltage differential signaling (LVDS) data encoding/transmission scheme. In one embodiment, the data bus 346 may be implemented with a two-wire single ended configuration (i.e. clock and data lines), or the like.

More specifically, in some embodiments, the high-speed data bus control interface 329 implements a digital line coding scheme such as the Manchester coding protocol (e.g., IEEE 802.3 standard) to encode the digital samples for digital transmission over the data bus 346. As is known in the art, Manchester coding is a line code in which the encoding of each data bit is either low then high, or high then low, of equal time (e.g., a logic 1 is expressed by a low-to-high transition, a logic 0 is expressed by a high-to-low transition). Therefore, Manchester encoded data has no DC bias and is self-clocking, thereby allowing the receiver to recover a clock signal from the encoded data that is transmitted to the receiver. Furthermore, in some embodiments, the high-speed data bus control interface 329 (FIG. 3B) comprises data line driver circuitry which implements a LVDS scheme for outputting encoded digital samples on the shared data bus 346. As is known in the art, LVDS is a physical layer specification to enable differential, serial transmission of an encoded data stream over a two-wire data bus (e.g., twisted-pair lines).

Furthermore, in some embodiments, time sharing on the data bus 346 is implemented using a token-based data bus sharing protocol, as discussed follows. When the chipsets 320 have been assigned unique Device ID address, resulting in complete configuration of the control bus 344, a token-based control scheme can be used for time-shared control of the data bus 346 so that each chipset 320 can transmit bocks of digital samples to the master controller 312 as part of a data collection cycle initiated by the master controller 312. In this scheme, the master controller 312 will send out a control token (e.g., output enable token) on the first token control line 342 to the first chipset 320-1, and the token will be passed down the chipset chain in sequence to the last chipset 320-N, where the token is then passed back to the master controller 312 via the second token control line 343.

When a given chipset 320 receives the token (either from the master controller or from an upstream chipset), the chipset will output a recently obtained data block of digital samples on the data bus 346 for transmission to the master controller 312, and then pass the token to the next chipset in the chain, or back to the master controller from the last chipset 320-N. Once the token is passed back to the master controller 312, the master controller 312 can decide when to send out another token control signal to commence a data collection cycle for the next set of digital samples. In the meantime, either during or after the data output operation, each chipset 320 operates to acquire and generate a next set of digital samples to output to the master controller 312 for a next data collection cycle that is initiated by the master controller 312 sending out a next control token. In this manner, the overall sampling rate of the system is determined, at least in part, by the rate at which the tokens are passed into the array of chipsets 320 from the master controller 312.

Optionally, for purposes of debug, or for secondary data transmission, the chipset 320 may comprise a low impedance analog output that can be captured, independent of the operation of the ADC and digital hardware. For example, in some embodiments, the digital data output can be turned off independently of the signal chain, wherein the channel amplifiers and multiplexer in the signal chain continue to run and are responsive to any timing signals on the token control line to generate an analog output, but where the ADC and digital encoding/outputting functions can be independently turned off. This is to ensure that the digital components of the chipset can be disabled in one or more operating modes, so as to maintain as low of a noise floor as possible while testing analog portions of the chip or collecting exquisitely small signals in one or more applications.

It is to be appreciated that there are numerous advantages associated with implementing the system 300 (FIGS. 3A/3B) within a medical device to capture and process physiological signals, as compared to conventional devices. For example, the system 300 allows low-voltage analog EP signals (on the order of 1-100 μV) to be effectively captured and processed, while eliminating or substantially reducing potential corruption of the analog EP signals from various EMI sources and/or simultaneously collecting a large amplitude EP signal (on the order of 200 μVp5 mV) upon which the small signal is superimposed. Indeed, by placing the network of chipsets 320 in proximity to the sense electrodes 321 in the sensing tip 130 of the medical device, the analog EP signals captured on the sense electrodes 321 are essentially processed on-site (amplified, filtered, and digitized) by the chipsets 320, thereby decoupling all potential EMI sources that could otherwise corrupt the EP signals as with conventional designs where the EP signals are simply transferred from the sensing tip through the catheter body over elongated electrode wires.

Furthermore, the chipsets 320 can be fabricated with low power CMOS process technologies, which allow each chipset 320 to occupy an extremely small volume (e.g., about 1.0×2.0×0.2 mm volume for at least 16 channels), while maintaining a high-fidelity EP sensing front end by use of the chipsets 320 with low power requirements to minimize generation of heat at the sensing site.

Moreover, the system 300 enables the implementation of a high-fidelity EP sensing frontend which comprises hundreds of sense electrodes to capture EP signals, while allowing the chipsets 320 and master controller 312 to communicate and transfer data over a minimal amount of data/control lines 340 which are included in a wiring harness that extends through the catheter body 110. In some embodiments, the number N of chipsets is 16, and the number of sense electrodes 321 (sensing channels) connected to each chipset is 16, thereby resulting in 256 sense electrodes in the system 300. However, as shown in FIG. 3A, irrespective of the number of sense electrodes used, the wire bundle 340 (or wiring harness) can be fabricated with as little as 10 wires— two wires for the control bus 344, two wires for the data bus 346, two wires 342/343 for token control, two wires 341, for power control 341, and two wires 345 for A/D debugging control. In conventional designs, the wire bundle would have at least 256 electrode wires to transfer the EP signals captured on 256 sense electrodes.

As noted above, the system 300 shown in FIG. 3A allows the master controller 312 to control and communicate with a plurality of chipsets (e.g., 16 or more) over the bi-directional control bus 344, which can be implemented with as little as one control line, and in some embodiments two control lines (e.g., SDA and SCL lines). The number of chipsets 320 that can be coupled to the control bus 344 is only limited by a capacitive load of the control bus 344 and the overall desired rates for adjusting the operational parameters of the chipsets 320 via the control bus 344. For a system comprising a large number of chipsets, two or more control buses can be utilized (chipset-side) wherein the control bus 344 is connected to a multiplexer/switch module (disposed chipset-side) which selectively connects the control bus 344 to two or more separate control buses to which different sets of chipsets are connected.

In addition, as noted above, the data bus 346 can be implemented as a 2-wire, time-shared data bus in which all data output lines of the chipsets 320 (up to a certain number of chips) are coupled to the same data bus 346. The overall limitation to the number of chipsets 320 that can be connected to the data bus 346 is based on a desired throughput capability of the data bus 346. In some embodiments, the data bus 346 may be configured to operate at a bandwidth of 64 Mbps, which would allow the system 300 to be implemented with 64 chipsets 320 simultaneously on the data bus 346 with all 16 channels (per chipset) operating at >2 kHz bandwidth (e.g., 1024 sense electrodes per 2-wire data bus). To obtain higher bandwidth for the same bus configuration, a number of amplifier channels on one or more chipsets can be disabled. In applications requiring additional electrodes, additional 2 wire data buses may be added, i.e., the system is easily expandable in this regard to a significantly large numbers of sense electrodes.

Other advantages associated with the system 300 shown in FIG. 3A include the ability to dynamically adjust various system parameters on each amplifier channel in real-time (dynamic adjustment with a responsiveness to within a single sample response rate) which allows the EP signals under measurement to be adapted without introducing artifacts into the EP signals. For example, as noted above, the amplifier channels of a given chipset can be individually enabled or disabled, the filter bandwidths are adjustable, amplifier gains can be individually adjusted (e.g., from 20 dB-85 dB), DC offsets can be adjusted from several different tap-points so as to window a given signal for zooming in on it during use, and channel bandwidths can be individually adjusted (e.g., from DC-40 kHz (all channels)). The ability for real-time channel selectivity enables a diagnostic process to hone in on few selected target channels and simultaneously boost performance on such selected target channels including sample rate, dependent on channel selection count as needed for the application.

Furthermore, the register configuration data for all processing stages allows each processing stage to be automatically corrected for in terms of differential and common mode offset, gain, signal conditioning parameters, clock rates, etc. This allows dynamic real-time adjustment (on the fly) of the signal conditioning for any particular channel on any particular chipset to handle a combination of large EP signals (such as smooth and cardiac muscle activity, movement related signals, electrode differential offset-changes, etc.), while tracking small EP signals on top of the large signals (such as neural traffic, different types of neural traffic, superimposed on movement artifacts, cardiac signal, smooth-muscle signal, etc.).

Furthermore, given that the various functionalities of the chipsets 320 can be configured/adapted in real-time, various innovative clinical operations can be performed using the system 300 of FIG. 3A. For example, the system 300 can operate in a "seek" mode, where all amplifier channels of all chipsets 320 are running in parallel, while the human operator is manipulating the medical device to look for target signals. The operator could manipulate the sensing tip of the medical device over a surface in the body and monitor for target signals, create a myocardial action potential (MAP) of electrophysiological traffic, or the like. When target signals are found in the vicinity of one or more sensors, the system, control software, and/or an operator can disable certain channels of one or more chipsets with weak or no EP signal activity, while honing in one channels with strong EP signal activity by increasing the sample rates on such active cannels and digitally recovering more data from the target channels (i.e. maintaining the overall data throughput of the entire system while homing in on target channels). The system can still sample at full throughput and digitally recover much more information from the target channels, at the expense of having turned off some other channels in the system.

For example, assume a circumstance in which key EP data is only visualized on 1 channel per chipset 320. In such instance, all other channels of each chipset 320 can be disabled or powered down (i.e. so as to save power and reduce noise as much as possible), and the ADC sampling rates can be increased on the active channels to a much higher rate, e.g., greater than 10× the base sampling rate, greater than 100× the base sampling rate, greater than 1000× the base sampling rate, alternatively greater than 20 ksps, greater than 100 ksps, greater than 500 ksps, greater than 1 Msps, or the like. The oversampled signal may then be digitally filtered, noise shaped, and down sampled back down to a reasonable bandwidth while structuring the noise floor and obtaining many additional bits worth of resolution in the signal (essentially 1 additional bit of resolution for every doubling of bandwidth). This strategy allows one to simultaneously obtain large cardiac signals along with exquisitely small neural signals (DC-5 kHz noise floor <1 uV), and then digitally extract neural features, etc., from the cardiac signal with very high resolution from the channels on which neural traffic is evident.

In another example, the amplifier gain can be reduced and the system can monitor for a myocardial action potential (MAP) with a particular channel, once it passes, the system is configured so as to temporally increase sampling rate as well as gains so as to zoom in on the target signal and search for neural traffic before the next MAP hits. This allows the system to search in extremely high fidelity for neural signal nearby key electrodes, while simultaneously satisfying all sensing requirements on the cardiac signals. The complete signal structure can be recreated from the digital signal and visualized in a form that a user can understand. In some embodiments, these operations may be performed automatically by the system, such as in an atrial mapping application. In such a scenario, the system may provide multiple synchronous maps to a user, a first map of spatial and temporal cardiac signal transmission over the target tissues, and one or more secondary maps showing neural traffic spatial and temporal transmission over the target tissues during use. In general applications, further signal processing, map generation, signal extraction algorithms, and the like, will be separated and visualized in the back-end for presentation to the user.

In another example, movement artifact is detected on key channels. The control bus is used to automatically re-center the data on the movement artifact at a rate of several 10s of Hz, and the gain on each channel is boosted to maintain high fidelity signal acquisition in the presence of the large signal associated with the movement artifact. The full signal is then reconstructed digitally and separated in the mid-end or back-end so as to remove the artifacts from the key signals under acquisition.

In another example, the system may be coupled with a therapeutic device, such as an ablation device. In this scenario, the system may be used to hone electrophysiologic recording in real-time around the current flow from an ablation catheter, so as to focus the sensing efforts around affected zones, determine the limits of the affected zones, monitor field around the ablation catheter for adjusting therapy, determine the connectivity of adjacent ablation sites to each other, etc.

In some embodiments, the sampling and data transfer operations may be handled by the control bus or the data bus directly, thus further freeing the need for additional wiring in the system. In one embodiment, the control bus includes a single master controller, and each chipset 320 in the array may be given a sequence ID during an initialization and configuration operation (i.e. when in the sequence they will send data). In this embodiment, the master controller may kick off a data transfer event by sending a broadcast command on the control bus or data bus and the devices may respond in sequence on the shared data bus. In another embodiment, the chipsets 320 may be given sequence IDs and a timing delay to repeatedly complete a data send sequence. In this scenario, the chipsets 320 may transfer data to the master controller at a fixed interval in a predetermined sequence without the need to pass tokens there between during operation.

In some embodiments, the control bus and data bus may be shared such that control and data transfer in the system may be completed with only two wires. In this embodiment, control messages and data transfer events are time-shared on the bus. Such operations may be performed in the following way. When the bus is free, the master may send commands to chipsets 320 in the array to configure the chipsets 320 for use. To collect data, the master may send a special command use (e.g. a brief bus assertion command, a specific broadcast command, etc.), which initiates the serial data transfer operations on the bus. Such a configuration may be advantageous for extremely size constrained applications, and applications where the wiring between the chipsets 320 and the master controller must be severely constrained.

FIG. 4 schematically illustrates a system 400 which is integrated within a medical device to capture and process physiological signals, according to another embodiment of the invention. The system 400 comprises a control system 410, a plurality of chipsets 420-1, 420-2, . . . , 420-N (collectively, chipsets 420), and a wire bundle 440 connecting the chipsets 420 to the control system 410. The system 400 shown in FIG. 4 is similar to the system 300 shown in FIG. 3A, except that the system 400 of FIG. 4 is configured to transmit analog data signals from the chipsets 420 to the control system 410. As noted above, each chipset 420 may be considered a "processing module" within the context of such term as used herein to discuss various embodiments and as used in the claims.

As shown in FIG. 4, the control system 410 comprises a power manager 314 and a master controller 312 similar to the system 300 of FIG. 3A, and further comprises a signal processor 420 and a digital signal manager 430 (implemented in the master controller 312). The system 400 further comprises a wire bundle 440 connecting the chipsets 420 to the control system 410. The wire bundle 440 is similar to the wire bundle 340 of FIG. 3A, except that the wire bundle 440 in FIG. 4 comprises a non-shared data bus 446, wherein the data bus 446 comprises a separate data line 446-1, 446-2, . . . , 446-N (e.g., single or differential) for each chipset 420-1, 420-2, . . . , 420-N, respectively. In other words, the data bus 446 is configured to individually connect an analog output of each chipset 420-1, 420-2, . . . , 420-N to an input of the signal processor 420 using the separate data lines 446-1, 446-2, . . . , 446-N, respectively.

The system 400 is similar to the system 300 shown in FIG. 3A in that the chipsets 420 in FIG. 4 are connected in a sequential chain based on token control lines 342, 343, and 315. Further, each chipset 420 is similar in architecture to the chipset 320 shown in FIG. 3B in that each chipset 420 includes amplifier circuitry 322 (with multiple parallel channels of multistage amplifiers) to amplify analog signals captured on the respective sense electrodes 321 for the chipset 320. However, the chipsets 420 in FIG. 4 do not utilize ADC circuitry for digitizing the amplified analog signals or other digital circuitry for encoding and outputting digital data. Instead, the amplifier channel outputs (e.g., amplified/filtered analog physiological signals) of the chipsets 420 are selectively input (via operation of a multiplexer circuit) to an analog data bus control interface of the given chipset 420, wherein analog data signals are output on the separate analog data lines 446-1, 446-2, . . . , 446-N of the respective chipsets 420. Each chipset 420 essentially operates to amplify the analog signals captured on the sense electrodes 321, enhance the impedance and noise floor of the analog signals, and then time-share the amplified/filtered analog channel outputs on a single output data line per chipset.

In some embodiments, the signal processor 420 of the control system 410 implements ADC circuitry and other digital processing circuitry to convert the analog data received on the non-shared data bus 446 from the chipsets 420 into digital data, wherein the digital data is input to the digital signal manager 430 of the master controller 312 for further processing and handling.

In this regard, in some embodiments, each chipset 420 is configured to generate time-shared multiplexed differential analog data output signals which are respectively transmitted on the analog data bus 446, in parallel, on the respective analog data lines 446-1, 446-2, . . . , 446-N. In one embodiment, the high-speed data bus control interface 329 in FIG. 3B would be implemented in each chipset 420 using analog line driver circuitry to provide a low impedance analog output of time shared signals captured from the respective set of sense electrodes 321 of the chipsets 420. The output drivers of the chipsets 420 would provide low impedance sufficient to drive the analog data lines of the non-shared data bus 446 that passes through the catheter body 110.

The system 400 of FIG. 4 and the system of FIG. 3A each provide various benefits and advantages. For example, the system 400 of FIG. 4 may be preferred over the system of FIG. 3A because the analog data rates can be lower on the data bus 446, EMI filtering is easier to implement, and less digital power is needed in the chipsets 420. The system of FIG. 3A, however, may be preferred as it reduces the number of wires that are routed through the catheter body 110 relative to the system 400 of FIG. 4 and completes all conversion at the distal tip rather than risk EMI associated with analog signal transfer to the controller.

In some embodiments, the system 400 of FIG. 4 may utilize a token control signal for timing alignment purposes, depending on the system configuration. For example, a control token can be used to synchronize the timing for each of the chipsets 420 and may be quickly passed from the master controller 312 to the first chipset 420-1, and then to successive chipsets 420 in the chipset, and then back to the master controller 312 on each time cycle or on occasion to ensure a timestamp of the initial channel multiplexer edges are known.

For example, in some embodiments, when a given chipset 420 receives a token control signal (from the master controller 312 or from an upstream chipset 420), the given chipset 420 will start a data acquisition cycle and sequentially cycle through the active/enabled signal channels (at a configured rate) to amplify/filter analog signals on each of the sense electrode 321, and then sequentially output the amplified/filtered analog signals from each active/enabled signal channel to the analog data output control circuitry. The analog data output is then a time-shared view of the analog data signals output from each signal channel with a temporal alignment being provided by the token receipt.

In some embodiments, when a given chipset 420 receives the data output token, the given chipset 420 will immediately initiate a data acquisition cycle, and then immediately pass the token out to the next chipset 420 in the chain (or back to master controller if last chipset 420-N) even before completing the data acquisition cycle and outputting the analog data on its respective data line. Once the chipset 420 completes the data acquisition cycle, the chipset 420 will enter a wait state for the next received token signal.

In some embodiments, the data lines may be shared and the token may be used to time slot each of the chipsets 420 corresponding analog data transmission on the data lines, allowing time sharing the analog signals on a minimum number of data lines. In these embodiments, the chipset 420 that receives the token takes control of the data lines will send the multiplexed analog data along the data lines, then tri-state its output driver, and then pass the token to the next successive chipset 420 in the signal chain. In such embodiments, the number of lines in the wire harness is minimized, but the time-shared nature of the analog signal transmission may limit the overall amount of data that can be transferred versus the digital version of the data bus.

In some alternate embodiments, data acquisition is performed without using a token control signal for synchronization. In such embodiments, each chipset 420 operates in "free running" mode with the multiplexer circuitry cycling through the active/enabled signal channels. In some embodiments, a "dead" channel or high/low internal channel can be utilized to add a time stamp to the data output sequence so that the timeslot of each signal channel data output will be known to the decoder.

FIG. 5 is a high-level system block diagram which illustrates a system configuration of circuit modules of a chipset, according to an embodiment of the invention. In particular, FIG. 5 illustrates a more detailed framework of a chipset 320 (as shown in FIG. 3B) which can be implemented in the system 300 of FIG. 3A. For purposes of illustration, FIG. 5 will be discussed in the context of the system 300 and chipset 320 shown in FIGS. 3A and 3B. FIG. 5 illustrates a system 500 comprising an analog block 502 and a digital block 504. The analog block 502 comprises an amplifier block 506 and a multiplexer/ADC block 508. The digital block 504 comprises a data acquisition block 510, a bus communication control block 512, a token control block 514, a system control block 516, and a multiplexer block 518. The system 500 further comprises a clock and power manager block 520.

The amplifier block 506 comprises a plurality of multi-stage amplifiers that are configured to amplify analog signals (e.g., EP signals) which are captured on the sensing electrodes at a sensing tip of a catheter device, as discussed above. In some embodiments, there are multiple amplifier channels, wherein each channel is configured to amplify analog signals captured on a given sense electrode in the set of sensing electrodes coupled to the amplifier channel inputs of the amplifier block 506. The multiplexer/ADC block 508 comprises a multiplexer circuit that selectively connects the output of each amplifier channel of the amplifier block 506 to the input of an analog-to-digital converter (ADC) circuit, wherein the ADC circuit is configured to digitize the amplified analog signals output from the amplifier channels of the amplifier block 506. The digitized signals are output to the data acquisition block 510 wherein the digitized signals are temporarily buffered, line encoded (e.g., Manchester coding), and then transmitted out over the high-speed data lines (e.g., high-speed LVDS-configured data lines) to the master controller 312 system for further processing, as discussed above.

The bus communication control block 512 is connected to the Token IN port and the control bus 344 input ports of the chipset. The bus communication control block 512 comprises interface circuitry to interface with the control bus lines 344, as well as control circuitry to communicate with the master controller 312 over the control bus 344 and process control signals sent by the master controller 312 for: (i) receiving and writing configuration data to the control registers 328; and (ii) reading and sending register configuration data from the control registers 328 to the master controller 312. In addition, depending on the type of token received on the Token IN port of the chipset, the bus communication control block 512 handles the processing and routing of token signals received on the Token IN port from the master controller 312 and from an upstream chipset in the sequential chain of chipsets.

For example, when the chipset 500 is in a state of initialization and an "address assignment" token signal is received on the Token IN control port from either the master controller 312 or from the Token OUT port of an upstream chipset, the bus communication control block 512 communicates with the master controller 312 over the control bus 344 to dynamically assign a new Device ID to the chipset 500 and write the new Device ID to a corresponding control register. When the new Device ID is assigned, the bus control block 512 generates/sets a bus configuration signal, which is sent to the data acquisition block 510 and other components to indicate that the control bus has been configured for normal operation.

When the control bus has been configured and a Device ID assigned, the bus communication control block 512 will pass a token signal received on the Token IN port to the token control block 514. The token control block 514 will either pass the token signal to the data acquisition block 510 to initialize a data acquisition cycle, or will immediately pass the token out to the next chipset or master controller on the Token OUT control line based on current token control settings (e.g., registers) that are communicated to the token control block 514 as token control signals from the bus communication control bock 512. The token control block 514 is configured to manage token input/output (I/O) according to token control signals output from the bus communication control block 512. In some embodiments, token management is controlled by a plurality of settings including, for example, SET_TOKEN, PUSH_TOKEN, HOLD_TOKEN and TOKEN_DLY, wherein the settings are controlled by the bus communication control block 512. When a SET_TOKEN is set, the token control block 514 will ignore any external token and generate a token signal which is output to the data acquisition block 510 to initiate a data acquisition process (referred to as "free run" condition). When a PUSH_TOKEN is set, the token control block 514 will send out one token immediately on the Token OUT control line, and then pass thru all incoming tokens until a PUSH_TOKEN bit is clear. When the PUSH_TOKEN bit is clear, normal operation will resume. When a HOLD_TOKEN bit is set, the token control block 514 will not output a token on the Token OUT control line of the chipset and the chipset will be held in standby mode. The TOKEN_DLY control specifies an additional delay time (in terms of clock signals) for the token control block 514 to output a token on the Token OUT port of the chipset.

In some embodiments, a token signal comprises an active low pulse that is at least 5 clock signals wide. Further, in some embodiments, the token control block 514 and the data acquisition block 510 comprise edge detector blocks which are configured to detect a falling edge of a token signal, wherein detection of the falling edge of the token signal is deemed an active low token signal for which action is taken.

The clock/power manager block 520 is configured to generate clock signals that are used by various system blocks to perform respective digital functions, and to control power level and distribution to the various system blocks based on control signals issued by the system control block 516. A master reset is generated by the clock/power manager block 520, while a soft reset is generated by the bus communication control block 512. The system control block 516 is configured to control configuration settings of various circuit components of the amplifier block 506, the multi-plexer/ADC block 508, and the data acquisition block 510, under control of the bus communication control block 512. For example, in some embodiments, the system control block 516 includes address decoders, and control registers which store configuration data (as discussed in further detail below with reference to FIG. 6).

The multiplexer block 518 is configured to selectively output data from various test points of the system on the A/D debug lines in response to control signals received from the bus communication control block 512. For example, analog test points may include a multiplexer output signal (right before ADC) of the multiplexer/ADC block 508, amplifier outputs of the amplifier block 506, an ADC reference, a comparator output, etc. Further, digital test points may include digital samples from the ADC block (prior to encoding and output), data clocks, multiplexer clocks, A/D sampling clock, chopper clock, system busy signals, send busy signals, etc.

Figure 6:
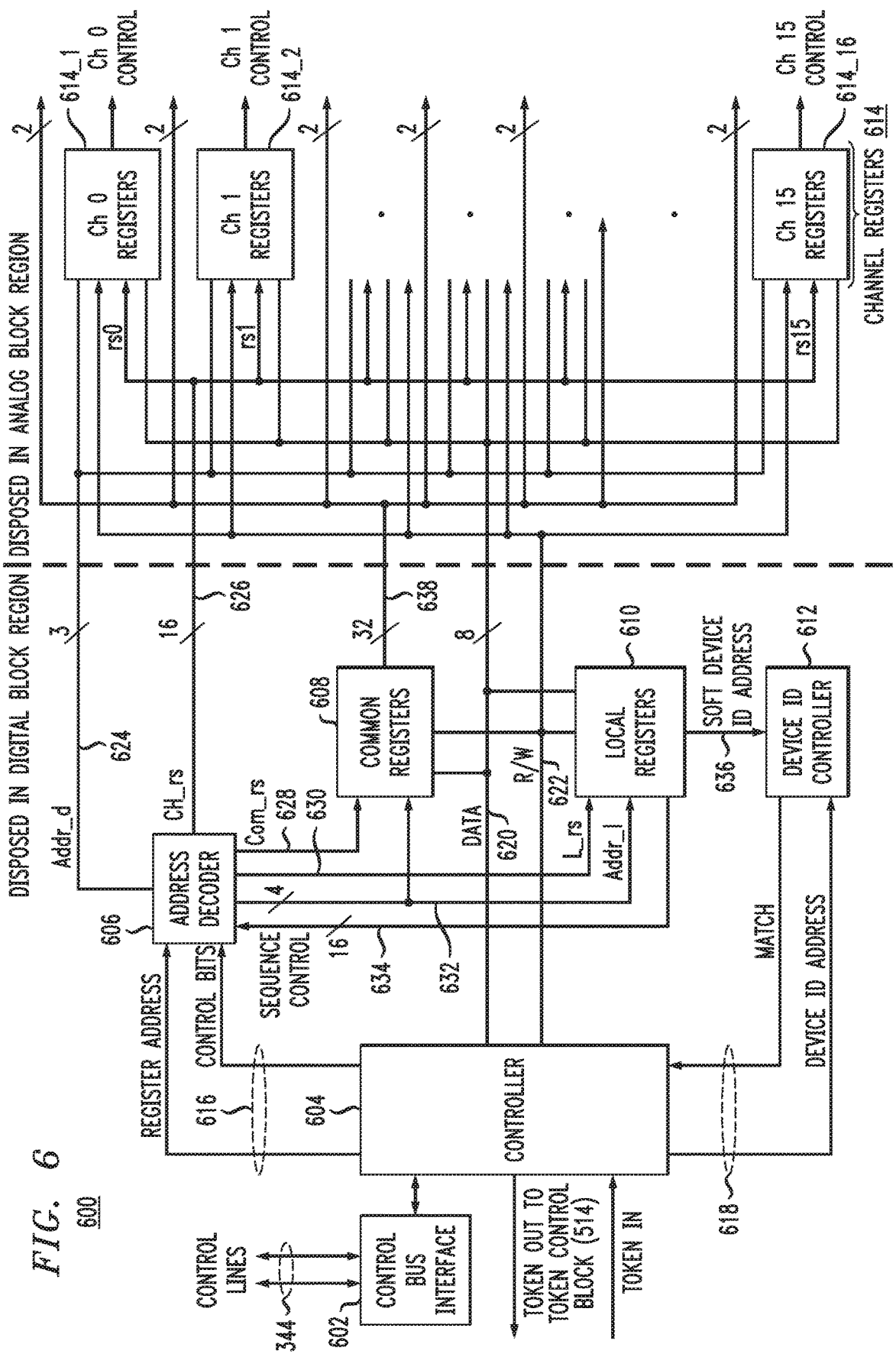
FIG. 6 is a block diagram that schematically illustrates a bus communication control system and associated functionality, according to an embodiment of the invention.

FIG. 6 is a block diagram that schematically illustrates a bus communication control system 600 on a chipset 320 and associated functionality, according to an embodiment of the invention. The bus communication control system 600 illustrates an example embodiment for implementing the bus communication control block 512 (FIG. 5), or collectively implementing the control bus interface 326, register control interface 327, and control registers 328 of the chipset 320 (FIG. 3B). As shown in FIG. 6, the bus communication control system 600 comprises a control bus interface 602, a controller 604, an address decoder 606, common registers 608, local registers 610, a device ID controller 612, and a plurality of channel registers 614. In some embodiments, the various system components 602, 604, 606, 608, 610, and 612 are disposed in a digital block region of a given chipset, while the channel registers 614 are disposed in an analog block region of the given chipset in proximity to, or within the amplifier block 506 (FIG. 5).

As shown in FIG. 6, the controller 604 is connected to the address decoder 606 by control lines 616 to allow the controller 604 to send a register address and control bits to the address decoder 606. The controller 604 is connected to the Device ID controller 612 by control lines 618 to allow the controller 604 to send a Device ID address to the Device ID controller 612 and to receive a "Match" control signal from the Device ID controller 612. In addition, the controller 604 is connected to the common registers 608, the local registers 610 and each of the channel registers 614 using a n-bit data line 620 which is utilized to read and write n-bit register data to the registers 608, 610, and 614. In the example embodiment, the n-bit data line 620 is shown as an 8-bit line where it is assumed that the register data stored in each register address location comprises 8 data bits. In addition, the controller 604 is connected to the common registers 608, the local registers 610 and each of the channel registers 614 with a read/write (r/w) control line 622 which allows the controller 604 to specify if a current register access operation is a register data read operation or a register data write operation.

As further shown in FIG. 6, the address decoder 606 outputs a decoded address (Addr_d) on an address bus 624 connected to the channel registers 614. The address decoder 606 outputs a channel register select signal (CH_rs) on a plurality (n) of channel register select lines 626, wherein each of the channel register select lines 626 (e.g., 16 select lines) is input to a corresponding one of the 16 channel registers (614_1, 614_2, . . . , 614_16). Further, the address decoder 606 outputs a common register select signal (Com_rs) and a local register select signal (L_rs) on respective register select control lines 628 and 630, and outputs a decoded address to the common registers 608 and the local registers 610 via an address bus 632. The local registers 610 are connected to the address decoder 606 by a sequence control bus 634 comprising, e.g., 16 control lines. The Device ID controller 612 is connected to the local registers 610 via a control line 636 to access a Device ID address stored in the local registers 610. The common registers 608 transmit control signals to the channels on a control bus 638 that is connected to an output of the common registers 608.

The controller 604 comprises an input that is connected to the Token IN port of the chipset to receive token signals from either the master controller 312 (FIG. 3A) or from the Token OUT port of an upstream chipset. The controller 604 will either process the received token (e.g. Device ID assignment) or pass the received token to the token control block 514 (FIG. 5) for handling. As discussed herein, a token received by the controller 604 may result in the start of bus configuration and address assignment processes, or trigger a data acquisition process for the given chipset.

The control bus interface 602 comprises hardware and/or logic to connect the bus control lines or otherwise couple control signals on the bus control lines 344 to the controller 604 for processing. The architecture of the control bus interface 602 and controller 604 will vary depending on the bus control system and protocol (e.g., I²C) that is implemented. As noted above, in an embodiment where the bus communication control system 600 of each chipset is implemented using the known I²C bus communication protocol, the control bus lines 344 would include a serial data line (SDA) and a serial clock line (SCL), and the control bus interface 602 would comprise the line buffers, pull-up resistors, and pull-down FET devices (open-drain/open-collector configuration) wherein the pull-down FET would be activated to pull the control bus down to a logic low level (e.g., ground), and deactivated to "release" the control bus by allowing the control bus to be pulled up to a logic high level (power rail) by the pull-up resistor.

The master controller 312 (FIG. 3A) communicates with the bus communication control system 600 of the given chipset to read data from and/or write data to the registers 608, 610, 614 of the given chipset. The controller 604 receives and processes control commands over the control lines 344 from the master controller 312 to write configuration data into one or more of the registers 608, 610, 614, or to read data (configuration data, status data, etc.) from one or more of the registers 608, 610, 614 for transmission to the master controller 312. In this regard, the controller 604 operates as a "slave controller" in the bus communication control protocol, to access the one or more registers which are the addressed in a given command sequence received from the master controller 312. The master controller 312 writes configuration data into the registers as a way to instruct the chipset device to execute tasks and configure circuitry as instructed by the master controller 312.

The channel registers 614 store configuration data that is used to configure and control the settings and operation of various components in the signal chain of each channel in the system which captures and processes analog signals (e.g., EP signals). For example, in the embodiment shown in FIG. 6, there is a set of channel registers for each of 16 separate channels (Ch0, Ch1, Ch2, . . . , Ch15). In some embodiments, the channel registers 614 comprise hardware registers that are configured as read/write registers to read or write multiple bits at time. Each register entry in the channel registers 614 is referenced by a unique register address in a total address space of register addresses, and comprises an n-bit word that specifies one or more values for different parameters associated with the given n-bit word, along with a r/w control bit that specifies whether the register entry is read only, write only, or read/write.

For example, in some embodiments, the channel registers 614 include one or more DC_Probe_Offset registers with a register entry for each channel. The DC_Probe_Offset registers comprise configuration data that specifies DC probe offset correction values, a polarity of DC probe offset correction, offset and gain parameters for each configurable stage of each channel, and filter bandwidth for analog components in each channel. For example, in some embodiments where each register entry comprises an 8-bit word, 5 bits can be used to specify 32 different values of DC probe offset in given range of DC probe offset (e.g., a range from 0 mV to 20 mV), and 1 bit can be used to specify the polarity of the DC probe offset (either positive or negative (0 or 1)). Further, 2 bits can be used to specify one of 4 different values for setting a filter bandwidth (e.g., 1.25 kHz, 2.5 kHz, 5 kHz, or 10 kHz). Further, the channel registers 614 may include Gain registers which comprise configuration data that is used to set a stage gain for each amplifier stage in a given channel amplifier. For example, in some embodiments, as noted above, the channel amplifiers may be configured with multiple stages of amplification (e.g., 2, 3, 4) to achieve sufficient gain and/or bandwidth. In addition, the channel registers 614 may include DC offset correction registers which comprise configuration data that is used to independently set a DC offset correction value and polarity of the DC offset correction value for one or more amplifier stages in a given channel amplifier.

The common registers 608 comprise registers having configuration data that is used to control the individual channels (e.g., Ch0, Ch1, Ch15). For example, the common registers 608 may comprise a Power-Up control register and a Channel_Active control register. The Power_Up control register comprises one or more register entries each comprising an n-bit word, wherein each bit enables a DC power down of a corresponding channel. For example, in the embodiment of FIG. 6 comprising 16 channels, the Power_Up control register may comprise two separately addressable register entries, wherein a first entry comprises an 8 bit word where each bit controls a DC power down of one of the channels Ch0~Ch7, and wherein a second entry comprises an 8-bit word where each bit controls a DC power down of one of the channels Ch8~Ch15 (e.g., a logic 1 value of a given power control bit enables DC power down of the channel associated with the given power control bit).

The Channel_Active control register comprises one or more register entries each comprising n-bits that select active channels for collection and transmission of data. For example, in the embodiment of FIG. 6 comprising 16 channels, the Channel_Active control register may comprise two separately addressable register entries, wherein a first entry comprises an 8 bit word where each bit controls channel selection of one of the channels Ch0~Ch7, and wherein a second entry comprises an 8-bit word where each bit controls channel selection of one of the channels Ch8~Ch15 (e.g., a logic 1 value of a given channel activation control bit for a given channel specifies that the given channel is selected/enabled for collecting and outputting data).

As shown in the example embodiment of FIG. 6, a plurality of control lines 638 (e.g., 32 lines) are output from the common registers 608, where 2 control lines of the plurality of control lines 638 are directed to each of the channels. These 2 control lines for each of the 16 channels can be utilized to output the control bits in the Channel_Active and Power_Up registers for the respective amplifier channel to selectively control DC power and Channel selection.

The local registers 610 comprises various system level registers such as control registers, configuration registers, status registers, and Device ID registers. For example, in some embodiments, the local registers 610 comprise configuration registers with control bits to configure functions of the data acquisition block 510 (FIG. 5) and high-speed data control interface (e.g., set drive strength of data line drivers, set values of one or more terminator resistors on LVDS data lines, set a voltage reference value VREF, EXT_ANA_OUT (enable low impedance analog output), PWR_DN_ADC (power down ADC and digital frame generator), COMM_MODE (select common mode path for selected channel), PARALLEL_OP (set ADC parallel/not parallel operation with data output transmission), set TOKEN_DLY (additional delay to send out Token, e.g., 000=0 clocks, 001=2 clock, . . . 111=7 clocks), and to control analog/digital multiplexer outputs to obtain selected test point for debugging, etc.

The local registers 610 further comprise ADC configuration registers with control bits to configure and calibrate the ADC block (e.g., trimming a capacitor array, trimming a reference current Iref and voltage reference Vref, etc.). The local registers 610 comprise read-only status registers to determine the status of, e.g., CLK_OK, ADC_REF OK, DVDD_OK, VREF_OK, TOKEN ("0"=token not present, "1"=token active within device).

The local registers 610 comprise read/write control registers with data bits to indicate or control various system parameters including, but not limited to, a START parameter (e.g., 1-bit that starts token ring state machine and data transfer, wherein 1 starts state machine and 0 stops state machine, where token stays with last active node), a RESET parameter (e.g., 1 bit that resets chip; 0 for normal operation, and 1 to reset the device wherein after reset, the device needs to be re-initialized), a PUSH_TOKEN parameter (1 bit that asserts a high on the chip Token OUT pin), a HOLD_TOKEN parameter (1 bit which is set to hold Token low independent of Token IN bit), a SET_TOKEN parameter (e.g., 1 bit to set token high independent of token IN value; starts state M/C on chip, where data out runs continuously), a TRI_STATE parameter (e.g., 1 bit to set the LVDS output to tristate (high impedance)), a DATA_SOURCE parameter (e.g., 1 bit; "0" sends ADC data based on CHAN_ACTIVE registers, and "1" dumps all registers in sequence before passing the token, wherein the data is not sampled, and one register per frame is generated), a TEST_FRAME parameter (e.g., 1-bit; "0" normal operation, "1" sending out test pattern), a TEST_PATTERN parameter (e.g., 2-bit value to specify a test patterns: 00=send out all "0", 11=send out all "1", 01=send out 0x555, 10=send out 0xA55), a FRAME_CTL parameter (e.g., 00=normal, 01=no node headers, etc.), and a BUS_CONFIG parameter (e.g., 1 back door bus configuration bit, wherein during initialization, this bit can be written when write to device ID 0x00 without initializing the device), etc.

The local registers 610 may comprise one or more special registers referred to as "write sequence control" registers which store commands to sequentially write configuration data to a particular set of channel registers for a set of selected channels. A "write sequence control" register will reference one or more "sequence write mapping" registers which provide a mapping of selected channels to which register data is to be written to corresponding channel registers. For example, in the embodiment of FIG. 6 which comprises 16 channels, a "write sequence control" register may comprise a command that references (i) a first sequence write mapping register which comprises 8-bits that map to respective channels Ch0~Ch7, and (ii) a second sequence write mapping register which comprises 8-bits that map to respective channels Ch8~Ch15, wherein a logic 1 specifies that the corresponding channel is included in the sequence and a logic 0 specifies that the corresponding channel is not included in the sequence.

By way of example, assume that the data bits [D0, D1, D2, D3, D4, D5, D6, D7] in the first sequence write mapping register (for channels Ch0~Ch7) specify a value of 0x62 (i.e., 0 1 1 0 0 0 1 0), and that the data bits [D0, D1, D2, D3, D4, D5, D6, D7] in the second sequence write mapping register (for channels Ch8~Ch15) specify a value of 0x83 (i.e., 1 0 0 0 0 0 1 1), such register values collectively specify that channels Ch1, Ch5, Ch6, Ch8, Ch9, and Ch15 are included in the write sequence specified by the first and second sequence write mapping registers.

When the master controller 312 references a register address that corresponds to a write sequence control register in the local registers 610, the controller 604 will expect the master controller 312 to sequentially write data to the channel registers of selected channels. In this regard, the write sequence control registers can be utilized to write to various channel registers such as the DC Probe Offset registers, the DC Offset amplifier stage registers, and the Gain registers are used to set a stage gain for each amplifier stage in a given channel.

The local registers 610 further include a Soft Device ID register which stores a soft device ID value for the given chipset (e.g., 7-bit value). This register can be written only after power up during initialization of a chipset when the first Token arrives. The value of this register will be a unique Device ID of the given chipset as assigned by the master controller 312 during a Device ID assignment process, and cannot be changed after initialization. This allows each chipset connected to the control bus 344 to be software-addressable by a unique address assigned by the master controller 312. The value of Soft Device ID register is initialized to a default initial Device ID of, e.g., 0x00, upon power up or device reset, and then changed to a unique Device ID.

The local registers 610 may further comprise a Broadcast Device ID register which holds a ID value BCDEV_ID (e.g., 0xFF), which allows the master controller 312 to send a command that will write to a target register on all chipsets on the control bus. For example, the master controller 312 can broadcast a Device ID address of 0xFF which addresses all chipsets 320, followed by a register address of a target register to which data is to be written, followed by a block of configuration data that is to be written to the target register in each chipset 320.

Referring back to FIG. 6, as noted above, the master controller 312 (FIG. 3A) communicates with the bus communication control system 600 of the given chipset to read data from and/or write data to the registers 608, 610, and 614 of the given chipset. When the master controller 312 wants to communicate with a target chipset and access the registers of the target chipset, the master controller 312 will send out a control command on the control bus 344 which comprises a unique Device ID address of the target chipset, and a register address to which register data is to be read from or written to on the target chipset, as well as a block of register data (e.g., data byte) to be written to the target register that is referenced by the register address.

Initially, the controller 604 will receive the Device ID address transmitted on the control bus 344, and then pass the received Device ID address to the Device ID controller 612. The Device ID controller 612 will access the contents of the Soft Device ID register and compare the contents of such register with the received Device ID address. Assuming that the control bus has already been configured for the given chipset, and that the master controller 312 has assigned a unique Device ID address to the given chipset, the Soft Device ID register would include the unique Device ID address assigned to the given chipset. If the Device ID in the Soft Device ID register matches the received Device ID, then it is determined that the received control command is addressed to the given chipset. On the other hand, if the Device ID in the Soft Device ID register does not match the received Device ID, then it is determined that the received control command is addressed to another chipset in the system.

The Device ID controller 612 will output a "match" control signal to the controller 604 indicating whether or not the received Device ID matches the Device ID in the Soft Device ID registers (e.g., a one bit control signal set to logic "1" to specify a match or set to logic "0" to specify no match). If the received Device ID matches the unique Device ID of the given chipset, then the controller 604 will pass the received register address to the address decoder 606, and the address decoder 606 will decode the register address in response to a control signal received from the controller 604 on the control lines 616.

The address decoder 606 will decode the received register address to determine the target register (e.g., a target register in one of register blocks 608, 610, or 614), and then generate a decoded register address to access the target register. The address decoder 606 will output the decoded register address on one of the address busses 624 or 632, and output an associated register select signal on one of the register select control lines 626, 628, or 630 to activate the register that corresponds to the decoded register address. In addition, the controller 604 will generate a read/write signal to the target register which specifies whether the current register command is a register read command or a register write command. For a read command, the controller 604 will receive register data on the data bus 620 which is read from the target register. For a write command, the controller 604 will send a block of register data (which was received from the master controller 312 over the control bus 344) to the target register on the data bus 620, wherein the register data is then written to the selected register in the target register address location referenced by the decoded register address.

In certain instances, a read or write command received from the master controller 312 may request access to a sequence of consecutive register addresses, wherein the master controller 312 issues a read request to read the contents of N successive register addresses starting from an initial target register address, or write data to N successive register addresses starting from a target register address. In this instance, the address decoder 606 comprises an address increment counter that is used to generate an incremental sequence of register addresses starting with the initial target register address to perform a series of register access operations to access a sequence of registers.

For example, after decoding an initial register address received from the master controller 312, and after accessing the register corresponding to the initial decoded register address, the address decoder 606 will utilize the address increment counter to increment the initial decoded register address by 1 to obtain a next sequential decoded address, and then utilize the incremented decoded address to access the next sequential register. This process is repeated to read or write data to N sequential registers as commanded by the master controller 312.

Furthermore, as discussed above, the master controller 312 may send a register address that corresponds to "write sequence control" register in the local registers 610, which indicates that the master controller 312 will sequentially write data to the channel registers 614 (e.g., DC Probe Offset registers, amplifier stage DC Offset registers, stage Gain registers, etc.) of a selected set of channels. When the master controller 312 references a "write sequence control" register, the address decoder 606 will access the one or more corresponding "sequence write mapping" registers in the local registers 610 which specify the selected set of channels to which data will be writing to the corresponding channel registers 614.

The contents of the "sequence write mapping" registers will be output to the address decoder 606 on the sequence control bus 634 to indicate to the address decoder 606 which channels are selected for the sequential channel register write operation. In the example embodiment of FIG. 6, the sequence control bus 634 comprises one sequence control line for each of 16 channels, wherein the logic level on a sequence control line for a given channel indicates whether or not the give channel is included in the sequence. The address decoder 606 utilizes the sequence control signals on the sequence control bus 634 to sequentially access and write data to target registers (e.g., DC Probe Offset registers, amplifier stage DC Offset registers, stage Gain registers, etc.) in each of the channel registers 614 for the selected set of channels specified by the sequence control signal.

Figure 7A:
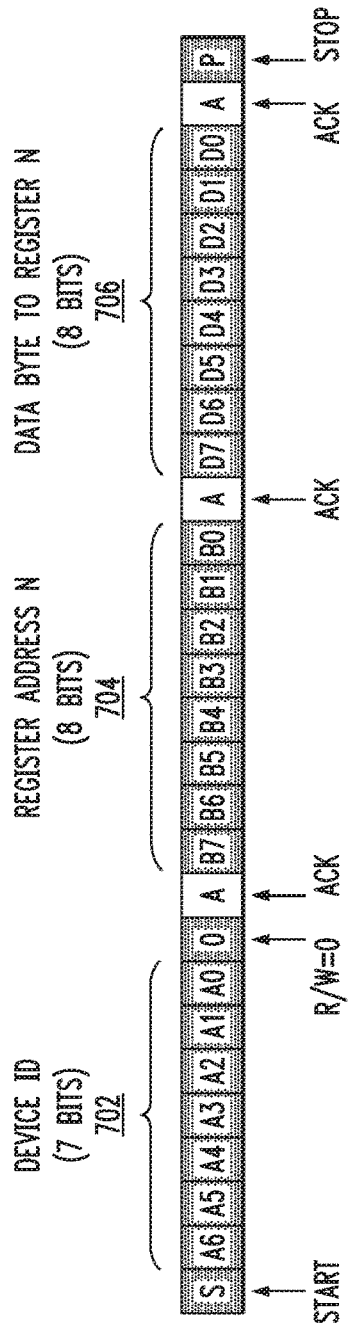
Figure 7B:
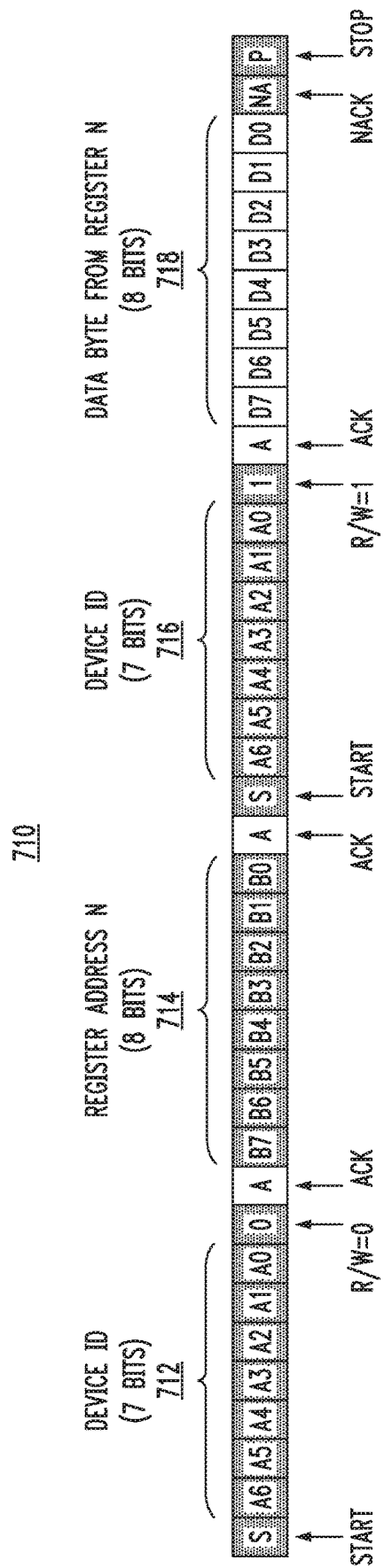

FIGS. 7A, 7B, and 7C illustrate exemplary command sequences that can be used to read data from and write data to registers according to an embodiment of the invention in which an I²C bus communication protocol is implemented by the communication control system of FIG. 6. As noted above, for the I²C bus communication protocol, the control bus 344 would include a SDA line and a SCL line. In the I²C communication scheme, the master controller 312 would initiate a communication with a target chipset by sending a START condition (or start signal) and terminating the communication by sending a STOP condition (or stop signal). A high-to-low transition on the SDA line while the SCL line is high defines a START condition. A low-to-high transition on the SDA line while the SCL line is high defines a STOP condition. Data transfer on the control bus 344 may be initiated only when the bus is idle, wherein the control bus 344 is considered idle if both the SDA and SCL lines are high after a STOP condition.

For example, FIG. 7A schematically illustrates a command sequence 700 for the master controller 312 writing data to a register of a given chipset device on the control bus 344. To write to a register of a slave device on the control bus, the master controller will send a start condition (START bit) on the control bus, along with a Device ID 702 of the target slave device, and a R/W control bit that is set to 0 to indicate a write operation. The target slave device which has the Device ID will respond to the master controller by sending an acknowledge bit (ACK) to the master controller. The master controller will then send a register address 704 of the register to which data is to be written. The slave device will acknowledge receipt of the register address by sending another acknowledge bit (ACK). The master controller will then send a block of register data 706 (e.g., 1 byte of data) to the slave device, and the slave device with send another ACK bit to acknowledge receipt of the register data 706. The master controller terminates the communication with a stop condition (STOP bit).

Figure 9:
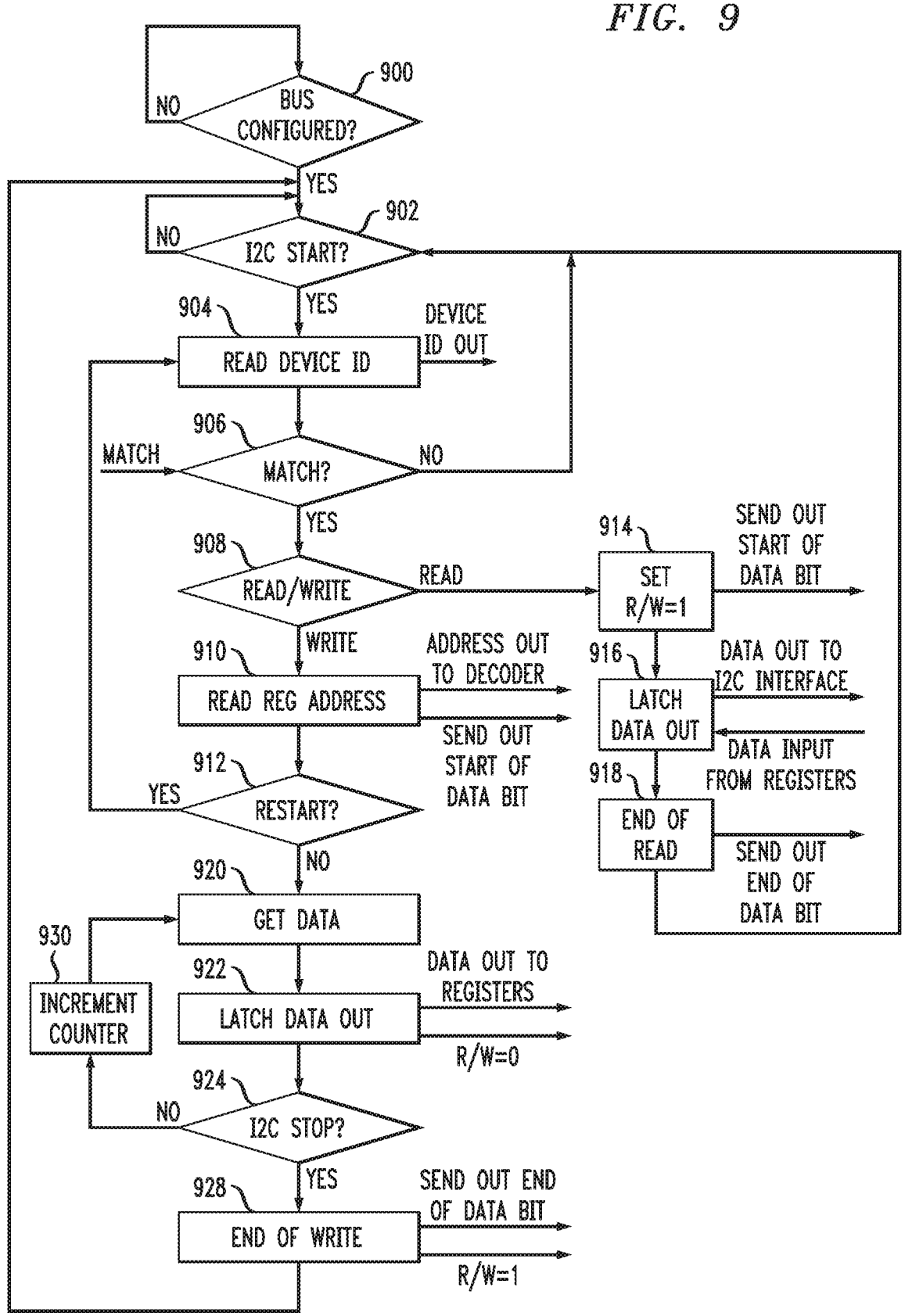
FIG. 9 is a flow diagram which illustrates a method for processing register access commands received from a master controller, according to an embodiment of the invention.

In the context of embodiments discussed herein, the command sequence 700 shown in FIG. 7A illustrates a single write command which can be implemented for writing data to the channel registers 614, the common registers 608, the local registers 610 (e.g., control, configuration and status registers), and the special registers (e.g., sequence write mapping registers for DC Offset), as will be discussed in further detail below with reference to FIG. 9.

FIG. 7B schematically illustrates a command sequence 710 for the master controller reading data from a register of a given slave device on the control bus. To read from a register of a slave device on the control bus, the master controller will first instruct the slave device which register the master controller wants to read from. This is performed by the master controller sending start condition (START bit) on the control bus, along with a Device ID 712 of the target slave device, and a R/W control bit that is set to 0 (signifying a write). The target slave device having the Device ID 712 will send an acknowledge bit (ACK) to the master controller. The master controller will then send a register address 714 of the register from which data is to be read. The slave device will acknowledge receipt of the register address 714 by sending another acknowledge bit (ACK).

Once the slave device acknowledges the register address 714, the master controller will send another START bit, followed by the slave Device ID 716 and a R/W bit set to 1 (which indicates a read). The slave device will then acknowledge the read request by sending an ACK bit, and the master controller releases the SDA bus, and continues supplying a clock signal (on the SCL) to the slave device. At this time, the master controller becomes a receiver, and the slave devices becomes a transmitter. The master will continue sending out clock pulses, and releases the SDA line, so that the slave device can transmit data to the master controller on the SDA line. The slave device then transmits the block of register data 718 (e.g., 1 byte of data) to the master controller. Once the master controller has received the expected number of bytes, it will send a NACK bit instruct the slave device to terminate communication and release the bus. The master controller then transmits a STOP bit.

FIG. 7B illustrates a read command sequence for reading a single byte of data from a slave register. However, the same protocol can be used to read multiple bytes of data from a slave register, wherein at the end of every byte of data that is transmitted to the master controller, the master controller will send an ACK bit to the slave device to indicate to the slave device that the master controller is ready to receive more data. Once the master controller has received the expected number of bytes, it will send a NACK bit instruct the slave device to termination communication and release the bus. The master controller then transmits a STOP bit.

In the context of embodiments discussed herein, the command sequence 710 shown in FIG. 7B illustrates a single read command which can be implemented for reading data from the channel registers 614, the common registers 608, the local registers 610 (e.g., control, configuration and status registers). The command sequence can also be used for reading data from the special registers (e.g., DC Offset Sequence Write Register and Sequence Write Mapping Registers for DC Offset), as will be discussed in further detail below with reference to FIG. 9.

FIG. 7C schematically illustrates a command sequence 720 for the master controller writing data to a plurality of registers of a given slave device on the control bus. The command sequence 720 is similar to the command sequence 700 of FIG. 7A, except that the command sequence 720 of FIG. 7C illustrates an exemplary consecutive write command sequence for writing data to an incremental sequence of registers (e.g., register N, N+1, N+2, . . . N+x), wherein the register addresses are incremented by 1. As shown in FIG. 7C, the consecutive write command sequence 702 begins with the master controller sending a start condition (START bit) on the control bus, along with a Device ID 722 of the target slave device, and a R/W control bit that is set to 0 to indicate a write operation. The target slave device which has the Device ID 722 will respond to the master controller by sending an acknowledge bit (ACK) to the master controller.

The master controller will then send a register address 724 of the first register (register N) to which data is to be written. The slave device will acknowledge receipt of the register address by sending another acknowledge bit (ACK). The master controller will then send a first block of register data 726-1 (e.g., 1 byte of data) to the slave device which is to be written to the first register N having the register address 724, and the slave device with send another ACK bit to acknowledge receipt of the register data 726-1. The master controller then consecutively sends a plurality of data blocks 726-2, 726-3, . . . , 726-n to the slave device, which are to be written to respective registers N+1, N+2, N+x having respective incremental register addresses following the first register address N 724. The slave device will send an ACK bit after the receipt of each additional data byte 726-2, 726-3, . . . , 726-n. The master controller terminates the communication with a stop condition (STOP bit).

In the context of embodiments discussed herein, the command sequence 720 shown in FIG. 7C can be used for writing data to a block of consecutive register addresses in the channel registers 614, the common registers 608, and the local registers 610 (e.g., control, configuration and status registers) starting from an initial register address using methods discussed above with reference to FIG. 6. For example, as discussed above, after decoding an initial register address received from the master controller 312 (e.g., block 724, FIG. 7C), and after accessing the register N corresponding to the initial decoded register address to write data (e.g., block 726-1, FIG. 7C) to the register, the address decoder 606 will utilize the address increment counter to increment the initial decoded register address by 1 to obtain a next sequential decoded address corresponding to the next register (N+1) and store the next received data block (e.g., 726-2) in the register (N=1). As shown in FIG. 7C, the process is repeated for a number of times until the last data block 726-n is stored in the last register (N+X) of the sequence.

In another embodiment, the command sequence 720 shown in FIG. 7C can be used for writing register data to a plurality of non-consecutive registers based on, e.g., the special "write sequence control" registers and corresponding "sequence write mapping" registers as discussed above. In this example, the register address N 724 in the command sequence 720 would reference a particular "write sequence control" register corresponding to a particular type of channel register (e.g., DC Probe Offset register, amplifier stage DC Offset register, stage Gain register, etc.) to which data is to be written in each of the register entries of the channel register corresponding to the selected channels as specified by the corresponding "sequence write mapping" registers referenced by the "write sequence control" register.

Figure 8:
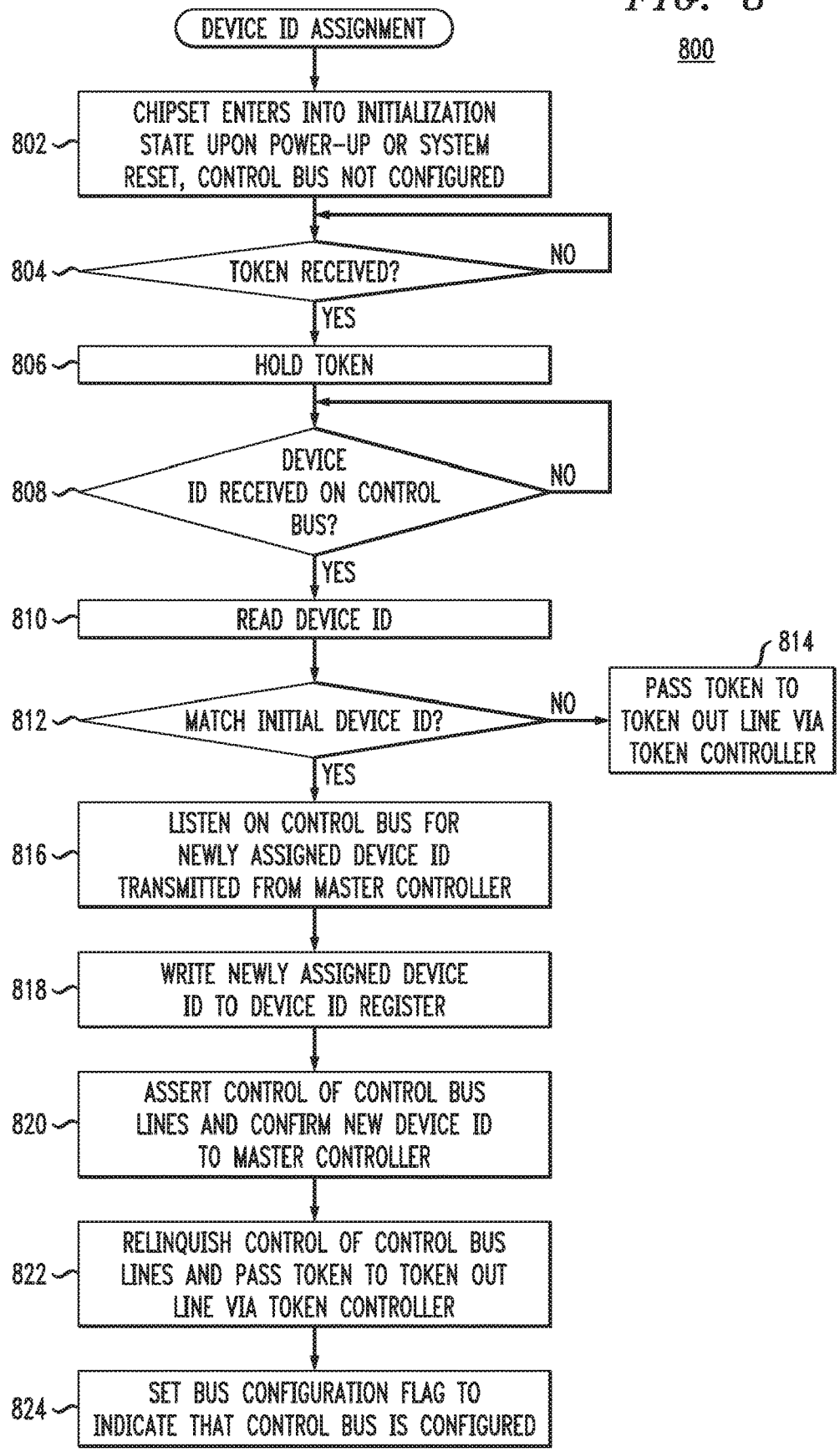
FIG. 8 is a flow diagram which illustrates using a token-based device ID (identifier) address assignment protocol to automatically assign unique software-addressable device IDs to the chipsets, according to an embodiment of the invention.

As noted above, after power-on or upon a system reset, a Device ID initialization/assignment process is commenced to automatically assign a unique device address to each chipset 320. FIG. 8 is a flow diagram which illustrates using a token-based Device ID assignment protocol 800 which is implemented by the master controller 312 and the slave chipsets 320 to automatically assign unique device IDs to the slave chipsets 320. In some embodiments, each chipset 320 has an initial Device ID (INIT_DEV_ID) of value 0x00. The INIT_DEV_ID is a temporary Device ID that is only enabled and utilized by each chipset 320 during an initialization process which is commenced after a power-up or a system reset event. When a given chipset 320 is in an initialization state and receives a Token signal on the Token IN control line, the chipset 320 will respond to a Device ID of INIT_DEV_ID (received from the master controller) to allow the master controller to write a unique Device ID (SOFT_DEV_ID) into the Device ID register of the chipset 320. The SOFT_DEV_ID is subsequently utilized for normal operation and communication with the master controller over the control bus.

Referring to FIG. 8, the Device ID assignment process flow 800 assumes that a given chipset is in a state of initialization following a power-up or system reset event, in which case the control bus is not yet configured for the given chipset (block 802). In the initialization state, the controller 604 (FIG. 6) of the given chipset enters into a wait state (block 804) to receive a token on the Token IN control line. When the controller 604 determines that a token is received on the Token IN control line (affirmative determination in block 804), the received token is held (block 806) and the controller 604 enters into a wait state to receive a Device ID as part of an initial command sequence transmitted on the control bus from the master controller (block 808).

When the controller 604 receives a Device ID from the master controller on the control bus (affirmative result in block 808), the Device ID will be read and compared to the initial Device ID (block 810). For example, in the embodiment of FIG. 6, the controller 604 will send the received Device ID to the device ID controller 612, wherein the device ID controller 612 reads the initial Device ID value from an associated register, and then compares the initial Device ID value to the received Device ID. The device ID controller 612 will then send a "match" control signal to the controller 604 indicating whether or not the received Device ID matches the initial Device ID value. If it is determined that the received Device ID does not match the initial Device ID (negative determination in block 812), the controller 604 will pass the token to the token control block 514 (FIG. 5), which sends the token out on the Token OUT control line (block 814).

On the other hand, if it is determined that the received Device ID does match the initial Device ID (affirmative determination in block 812), the controller 604 proceeds to listen on the control bus for a newly assigned Device ID transmitted from the master controller (block 816). The newly assigned Device ID is then written to Device ID register (e.g., Soft Device ID register) (block 818). In some embodiments, the process flow of blocks 808, 810, 816 and 820 is implemented using a single write command sequence such as shown FIG. 7A for the FC bus communication protocol. In this instance, the 7-bit Device ID following the Start bit would be the initial Device ID (INIT_DEV_ID), the 8-bit Register Address N would be the Device ID register to which the new Device ID would be written, and the 8-bit Data block would be the newly assigned Device ID of the chipset to be written to the Device ID register.

After receiving and writing the new Device ID to the Device ID register, the controller 604 will assert control of the control bus and confirm the new Device ID to the master controller (block 820). In some embodiments, the process flow of block 820 is implemented using a single read command sequence such as shown FIG. 7B for the I²C bus communication protocol. In this instance, the Device ID block 712 and 726 would include the newly assigned Device ID of the slave device, the register address 714 would be the address of the Device ID register, and the data byte 718 sent from the slave device to the master controller would include the address bits of the newly assigned Device ID which the master controller would read to confirm that the Device ID assignment process for the given slave device is complete.

Following confirmation of the new Device ID, the controller 604 of the chipset will relinquish control of the control bus lines and pass the token to the token control block 514 (FIG. 5), which sends the token out on the Token OUT control line (block 822). The controller 604 will then set a bus configuration flag to indicate that the control bus is configured for the given chipset (block 824). After the initialization and Device ID assign process of FIG. 8 is complete, the controller 604 of the given chipset will no longer respond to the initial Device ID (e.g., 0x00), and will only response to control signals on the control bus having a Device ID which corresponds to the newly assigned Device ID stored in the Device ID register of the given chipset. The process of FIG. 8 is performed for each chipset in the system up receiving the token which is passed from one chipset to another during the global Device ID assignment process.

In particular, after sending the token, the controller then sends the address for the first chip. Only the first chip is listening as it has address=0x00 and has received the token. It sets its address to the address sent by the controller and then takes control of the control lines and confirms the address back to the controller. As soon as the first chip is done with the confirmation, it relinquishes control of the control lines and sends the token onto the second chip. The controller sends the second address, and the process repeats until the token is returned to the controller (i.e. at that time all addresses are assigned).

Once unique Device ID addresses are assigned to all the chipsets, a basic address based communication protocol can proceed. FIG. 9 is a flow diagram which illustrates a method for processing register access commands received from a master controller, according to an embodiment of the invention. For purpose of illustration, the method of FIG. 9 will be discussed in the context of the bus communication control system 600 and the command sequences for the I²C bus protocol as shown in FIGS. 7A and 7B. When the control bus has been configured for a given chipset 320 (affirmative determination in block 900), the controller 604 will enter into a wait state listening on the control bus 344 for a "start" bit from the master controller 312 (block 902). When a start bit is received on the control bus 344 (affirmative determination in block 902), the controller 604 will receive a Device ID address transmitted on the control bus 344, and then pass the received Device ID address to the Device ID controller 612 (block 904). The Device ID controller 612 will determine (block 906) if the received Device ID address matches unique Device ID address of the given chipset assigned by the master controller 312 (via process of FIG. 8). If the received Device ID address matches the unique Device ID address assigned to the chipset, then it is determined that the master controller 312 the current control command is addressed to the given chipset (affirmative determination in block 906).

The controller 604 will determine if an R/W control bit at the end of the received Device ID address is set to "0" to indicate a register write operation or set to "1" to indicate a register read operation (block 908). As discussed above with reference to FIGS. 7A and 7B, with the I²C protocol, the initial Device ID address received from the master controller 312 will always have the R/W control bit (appended thereto) set to "0", irrespective of whether the register access will be a read or write operation (affirmative determination in block 908).

After the controller 604 sends an ACK bit to the master controller 312 to indicate receipt of the Device ID address, the controller 604 will receive a register address transmitted from the master controller 312 on the control bus 344 which references a target control register to which data will be read from or written to, and the controller 604 outputs the received register address to the address decoder 606 for decoding (block 910). The controller 604 will then send another ACK bit to the master controller 312 to acknowledge receipt of the register address.

At this point in the command sequence, if the master controller 312 wants to read data from the target register referenced by the previously transmitted register address, the master controller 312 will send another start bit on the control bus 344, indicating to the controller 604 that a read operation will be performed (affirmative determination in block 912) and then transmit a Device ID address on the control bus 344 for the target chipset which is appended with a R/W control bit set to "1" (see, e.g., block 716, FIG. 7B). The controller 604 will execute the same process as before, (blocks 904, 906, and 908), and in response to the appended R/W control bit of logic 1 (affirmative determine in block 908), the controller will generate a logic 1 signal on the R/W control line 622 to indicate the read operation to the target register (block 914).

In response to the R/W control signal of logic "1" on the R/W control line 622, and based on a decoded address output from the address decoder 606, a block of data (e.g., byte) will be read from the target register and sent to the controller 604 on the internal register data bus 620 (block 916), wherein the data is latched to the control bus interface 602 for transmission on the control bus 344 to the master controller 312. Once the master controller 312 receives the requested block of register data, the master controller will generate a NACK signal followed by a stop bit on the control bus 344 indicating (to the controller 604) the end of the register read operation (block 918).

On the other hand, referring back to block 912 in the process flow, if the master controller 312 wants to write data to the target register referenced by the previously transmitted register address, the communication is not restarted, i.e., another start bit is not transmitted on the control bus 344 from the master controller 312 (negative result in block), the register access process proceeds with the master controller 312 transmitting a block of data to be written to the target register address. The controller 604 receives the block of register data on the control bus (block 920). The controller 604 will then generate a logic "0" on the R/W control line 622 to indicate a write operation to the target register, and then send the block of register data on the internal data bus 620 (block 922). In response to the R/W control signal of logic "0" on the R/W control line 622, and based on a decoded address output from the address decoder 606, the block of register data received from the master controller 312 will be written to the target register.

The controller 604 will send an ACK bit to the master controller 312 and the master controller 312 will send a stop bit on the control bus 644 if the master controller 312 is finished with the register write operations. If the controller 604 determines that a stop bit has been received on the control bus 344 (affirmative determination in block 924), the write operation will be deemed complete and the R/W control line 622 will be set to logic "1" (block 928). On the other hand, the master controller 312 may want to write blocks of register data to two or more successive register addresses starting from the target register address received by the controller 604 (in block 910). In such instance, the master controller 312 will not generate a stop bit, but rather send one or more additional blocks of register data to be written to the one or more successive registers. As noted above, the address decoder 606 will increment a register address counter to determine the next successive register address to which the next received block of register data will be written (block 930). The process flow of blocks 920, 922, 924, and 930 will be repeated for each additional block of register data to be written to a sequence of register addresses.

Figure 10:
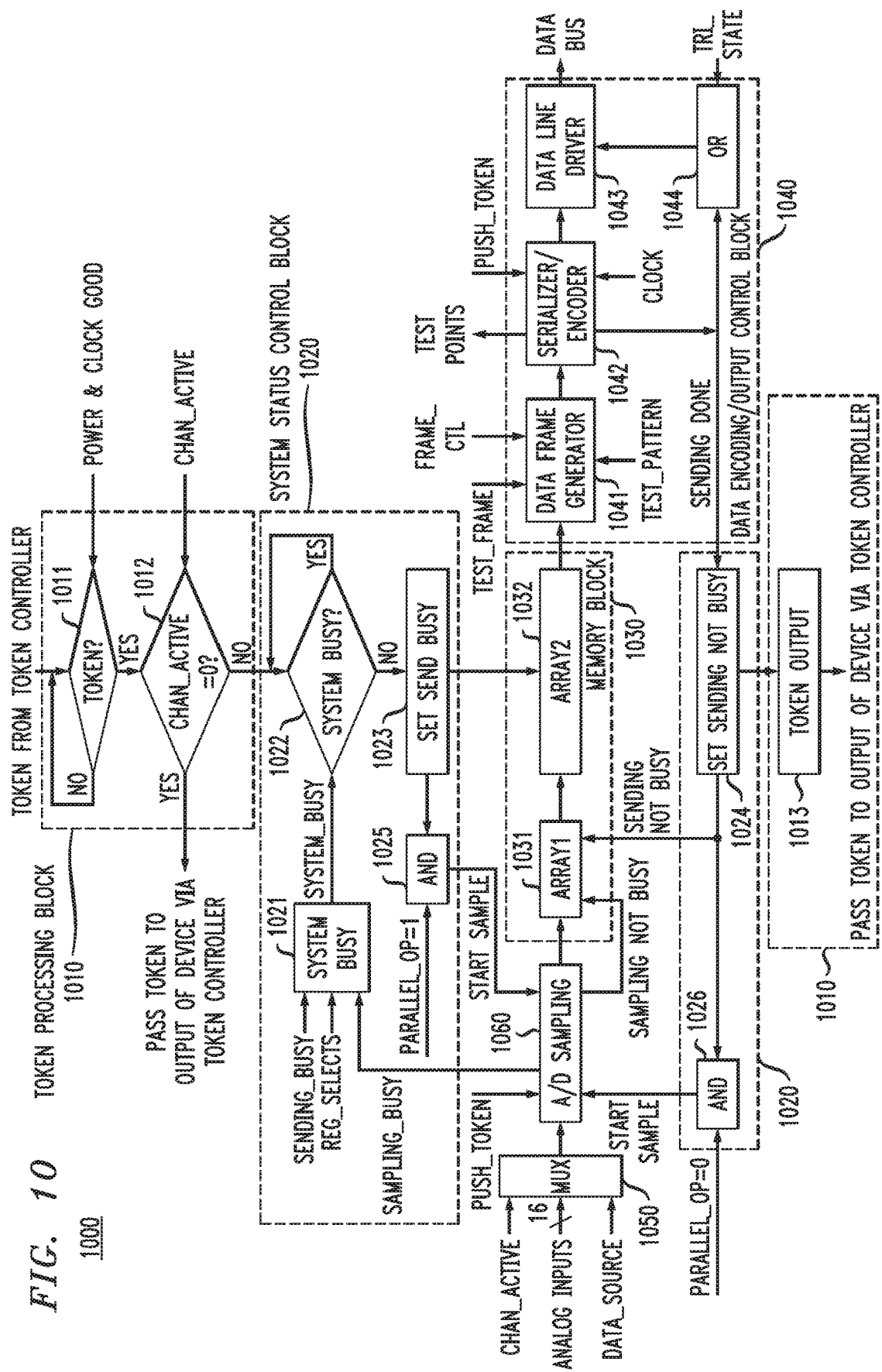
FIG. 10 is a block diagram that schematically illustrates a data acquisition system and associated process flows of a data acquisition process, according to an embodiment of the invention.

FIG. 10 schematically illustrates a data acquisition system 1000 and associated process flow according to an embodiment of the invention. More specifically, FIG. 10 schematically illustrates a process control architecture and associated operational modes of the data acquisition block 510 (FIG. 5) according to an embodiment of the invention. In general, the data acquisition system 1000 comprises a token processing block 1010, a system status control block 1020, a memory block 1030, and a data encoding and output control block 1040. FIG. 10 further illustrates a multiplexer block 1050 and an A/D sampling block 1060. The multiplexer block 1050 and the A/D sampling block 1060 depict an example embodiment of the multiplexer/ADC block 508 (FIG. 5), wherein FIG. 10 illustrates an associated control flow and interaction of the multiplexer/ADC block 508 and the data acquisition block 510 if FIG. 5, according to an embodiment of the invention.

The token processing block 1010 is coupled to the token control block 514 (FIG. 5), and comprises a token detection block 1011, an active channel determination block 1012, and a token output block 1013. The system status control block 1020 comprises a system busy control block 1021, a system busy determination block 1022, send busy control signal blocks 1023 and 1024, and A/D sampling control blocks 1025 and 1026. The memory block 1030 comprises a first memory array 1031 and a second memory array 1032. The data encoding and output control block 1040 comprises a data frame generator block 1041, a data serializer/encoder block 1042, a data line driver block 1043, and a data line driver control block 1044.

As shown in FIG. 10, various control blocks of the data acquisition system 1000 read and utilize configuration data stored in the registers to perform respective functions. For example, the active channel determination block 1012 and the multiplexer block 1050 utilize the CHAN_ACTIVE register data in the common channel registers 608 (FIG. 6) to determine which channels (electrodes) of the given chipset are currently selected for acquiring data for transmission to the master controller. The multiplexer block 1050 utilizes a DATA_SOURCE register setting stored in a control register to determine whether to send the analog data to the A/D sampling block 1060 based on the CHAN_ACTIVE registers, or to dump all I²C registers in sequence before passing the token (data not sampled, one register per frame).

The A/D sampling control blocks 1025 and 1026 utilize the PARALLEL_OP register setting stored in a configuration register of the local registers 610 (FIG. 6) to determine whether or not ADC sampling and data transmission can be performed in parallel (e.g., PARALLEL_OP="1" set ADC parallel operation with data transmission, and PARALLEL_OP="0" set ADC not parallel operation (wait for data transmission)).

The A/D sampling block 1060 and the serializer/encoder block 1042 utilize the PUSH_TOKEN register setting (1 bit) in a control register to determine if a logic "1" is asserted on the Token OUT pin of the chipset. When the PUSH_OKEN register setting is set to logic "1", such setting represents that a logic 1 level is asserted on the Token OUT line. This setting causes the A/D sampling block 1060 to suspend sampling operations, and causes the serializer/encoder block 1042 to output a "sending done" control signal to the control blocks 1024 and 1044.

The data frame generator block 1041 utilizes the "TEST_FRAME", "TEST_PATTERN" and "FRAME_CTL" register settings in a control register to perform functions. For example, the TEST_FRAME setting (e.g., 1-bit) instructs the data frame generator block 1041 to operate in a normal mode (logic 0) or to operate in a test mode by sending out a test pattern. The TEST_PATTERN register setting (e.g., 2 bits) specifies what the test pattern should be (e.g., all logic 0 bits, all logic 1 bits, alternating bit sequence of 1 and 0, etc.). The FRAME_CTL register setting (e.g., 2 bits) specifies different data frame structures (e.g., header, no header, etc.).

The data line driver control block 1044 utilizes the TRI_STATE register setting (e.g., 1 bit) of a control register to determine if the data line driver block 1043 should be set to the tri-state condition (high impedance output) (e.g., logic 1 setting sets the driver output to tri-state condition). As is known in the art, placing the driver outputs into a high-impedance state serves to effectively decouple the driver output from the shared data lines.

As further shown in FIG. 10, the multiplexer block 1050 comprises a plurality of analog data inputs, which represent the analog signals that are captured on the channel electrodes of the given chipset. The example embodiment of FIG. 10 shows 16 analog data inputs to the multiplexer block 1050, which correspond to 16 channel electrodes of the given chipset. The multiplexer block 1050 selectively outputs one of the 16 analog data inputs of the channel electrodes to the A/D sampling block 1060 at a given time, and the A/D sampling block 1060 digitally samples the analog data captured on the selected channel electrode at a given sampling rate. The processing result (digital samples) generated by the A/D sampling block 1060 (in a current sampling cycle) are temporarily stored in the first memory array 1031 of the memory block 1030. The second memory array 1032 of the memory block 1030 is configured to temporarily store digital samples generated by the A/D sampling block 1060 in a previous sampling cycle to await encoding and output by the data encoding and output control block 1040.

In some embodiments, the first and second memory arrays 1031 and 1032 of the memory block 1030 comprise register arrays. For example, the first memory array 1031 may be implemented as an array of registers comprising 16 registers, wherein each register corresponds to a given one of the 16 channels and is utilized to store the digitally sampled data for the given channel. Similarly, the second memory array 1032 may be implemented as an array of registers each corresponding to one of the 16 channels of the given chipset. As explained in further detail below, during a current processing cycle, the first memory array 1031 is utilized to store the digital samples generated during the current processing cycle, while the second memory array 1032 is utilized to buffer the digital samples generated during a previous processing cycle, and then transfer the current digital samples from the first memory array 1031 to the second memory array 1032 after the digital samples from the previous processing cycle (stored in the second memory array 1032) have been encoded and transmitted from the data encoding and output control block 1040 to the master controller over the high speed data lines.

In the data encoding and output control block 1040, the data frame generator block 1041 is configured to encapsulate each block of digital samples for the respective channels stored in the second memory array 1032 into a data frame. In some embodiments, each data frame comprises a frame synchronization header and a packet of digital samples (payload data block), wherein the frame synchronization header comprises a sequence of bits that specifies the beginning of the payload data block for the given data frame.

The data serializer/encoder block 1042 is configured to serialize and combine the data frames for all the channels generated by the frame data generator block 1041 into a single frame which encapsulates all the digital samples collected in a previous cycle for the active channels, and then encodes the single frame using an encoding protocol which is suitable for serial transmission of data over the high-speed data transmission lines. The date line driver block 1043 comprises output driver circuitry to drive the high-speed data lines. The data line driver control block 1044 is configured to generate a control signal to place the date line driver block 1043 into a high impedance state, in response to either a "sending done" signal generate by the serializer/encoder block 1042, or the assertion of a TRI_State control register signal.

In some embodiments, the serializer/encoder block 1042 encodes the frame using a suitable line coding protocol such as the Manchester coding protocol (e.g., IEEE 802.3 standard), as discussed above. Furthermore, in some embodiments, the data line driver block 1043 comprises line driver circuitry which implements a LVDS protocol (physical layer specification) to enable differential, serial transmission of the encoded data stream over the high-speed data lines (e.g., twisted-pair lines).

FIG. 10 schematically illustrates various control flows of the data acquisition system 1000 for a given chipset, which may occur when an "output enable" token is received by the given chipset, depending on whether the given chipset is in a "system ready" or "system busy" state. In either the ready or busy system state, the data acquisition system 1000 for a given chipset is configured to respond to the arrival of a token as follows.

The token processing block 1010 is configured to receive a token (e.g., "output enable" token) from the token control block 514 (FIG. 5), and to generate and output a token to the token control block 514 under certain conditions as discussed below. The token detection block 1011 determines when a token has been received from the token controller. When a token is received, the active channel determination block 1012 determines (based on the CHAN_ACTIVE register setting) whether or not channels for the given chipset have been selected for data sampling and data transmission. If no channels for the given chipset have been selected for processing (i.e., CHAN_ACTIVE=0, affirmative determination in block 1012), the token processing block 1010 will pass the token back to the token control block 514, so that the token control block 514 can pass the output enable token to either the next chipset in the sequence or back to the master controller (if the given chipset is the last chipset in the chain of chipsets).

On the other hand, if the CHAN_ACTIVE setting indicates that there are one or more active channels of the given chipset selected for data sampling and data transmission (i.e., CHANP_ACTIVE≠0, negative determination in block 1012), the token processing block 1010 holds the token, and the process flow passes to the system status control block 1020 to determine if the given chipset is in a "system busy" state or a "system not busy" state. In some embodiments, the system busy control block 1021 receives as input a plurality of input signals to determine if the given chipset is in a "system busy" state or a "system not busy" state. The input signals include, for example, a Send_Busy signal, a Reg_Selects signal, and a Sampling_Busy signal.

In some embodiments, the Reg Selects signal is generated by a logical "OR" of all register select control signals (e.g., CH_rs, Com_rs, L_rs) output from the address decoder 606 (FIG. 6) at a given time. The system (chipset) can be deemed busy if any one of the register select control signals is asserted indicating that the master controller is accessing register data of the chipset at that time. In such instance, the master controller may be changing one or more register settings that control the functions of one or more control blocks of the data acquisition system 1000 shown in FIG. 10, wherein it may be preferable for the system to delay data acquisition, data sampling, and/or data transmission operations until the register operations are completed.

The Sending_Busy signal is a control signal that is generated by operation of the send busy control signal blocks 1023 and 1024 of the system status control block 1020. While the send busy control signal blocks 1023 and 1024 are illustrated as separate blocks for ease of illustration of the process flow shown in FIG. 10, it is to be understood that such blocks 1023 and 1024 collectively form one control module which generates a Sending_Busy signal based on the status of control signals received from blocks 1022 and 1042. In some embodiments, the Sending_Busy signal is a control signal that is: (i) asserted and held at a logic 1 level during a period of time in which the data encoding and output control block 1040 is encoding a block of digital samples output from the second memory array 1032, and transmitting the encoded data to the master controller on the high-speed data bus; and (ii) de-asserted and held and a logic 0 level when the data encoding and output control block 1040 is done encoding/transmitting data in a given cycle and enters into a waiting period to encode and transmit a next block of digital samples.

The Sampling_Busy signal is a signal that is generated by the A/D sampling block 1060 to indicate an operational status of the A/D sampling block 1060. In some embodiments, the Sampling_Busy signal is a control signal that is: (i) asserted and held at a logic 1 level during a period of time in which the A/D sampling block 1060 sampling the analog data on the active channels selectively input to the A/D sampling block 1060 by operation of the multiplexer block 1050 during a given processing cycle; and (ii) de-asserted and held and a logic 0 level when the A/D sampling block 1060 is done sampling the analog data on the active channels during the given processing cycle and enters into a waiting period for a next sampling cycle.

The system busy control block 1021 generates a System_Busy signal which indicates whether the given chipset is in a "system busy" state or a "system not busy" state. The system busy determination block 1022 determines whether or not the system is busy based on the logic level of the System_Busy signal output from the system busy control block 1021. Under the circumstances in which the system busy determination block 1022 has determined that the system is not busy, and the token processing block 1010 has determined that a token has been received to commence a current data acquisition cycle and that there are active channels to be processed, the data acquisition system 1000 initiates and controls the execution of various processes to perform the current data acquisition cycle as follows.

A first process is commenced by the data encoding and output control block 1040 to encode and transmit a block of digital samples stored in the second memory array 1032 from a previous data acquisition cycle. As shown in FIG. 10, when the system busy determination block 1022 determines that the system is not busy (negative determination in block 1022), the send busy control signal block 1023 generates (asserts) a Sending_Busy signal, which is output to the memory block 1030 to enable the set of digital samples in the second memory array 1032 to be passed to the data encoding and output control block 1040 for encoding and transmission as discussed above.

Once the data encoding and output process for the given data acquisition cycle is completed, the data encoding and output control block 1040 generates "sending done" signal to the send busy control signal block 1024. In response, the control signal block 1024 de-asserts the Sending_Busy signal to indicate that the data encoding and output process for the given data acquisition cycle is complete (i.e., sending is not busy). In response to the Sending_Busy signal being de-asserted, the token output block 1013 will pass the token out to the token control block 514 (FIG. 6), which then outputs the token to the next chipset in the sequence to commence a data acquisition cycle on the next chipset. The token will be passed to the next chipset when the data encoding and transmission process is completed, irrespective of whether or not the A/D sampling process for the current data acquisition cycle has begun or has been completed.

A second process which is performed in the current data acquisition cycle involves operations of the multiplexer block 1050 and the A/D sampling block 1060 to capture and sample analog signals on the selected active channels and load the respective digital samples into the first memory array 1031 of the memory block 1030. Depending on the value of the PARALLEL_OP register, the A/D sampling process can either be (i) initiated concurrently and/or performed in parallel with the data encoding and output process, or (ii) initiated after the data encoding and output process for the current data acquisition cycle is complete.

In particular, as shown in FIG. 10, the A/D sampling control block 1025 performs a logical AND of the Sending_Busy signal and the PARALLEL_OP register value. When the Sending_Busy signal is asserted (logic 1) and the PARALLEL_OP register value is set to logic 1, the A/D sampling control block 1025 generates a "start sample" control signal to the A/D sampling block 1060 to enable the A/D sampling process to commence and execute concurrently with the data encoding and output process in the current data acquisition cycle. Similarly, the A/D sampling control block 1026 performs a logical AND of the Sending_Busy signal and the PARALLEL_OP register value. When the PARALLEL_OP register value is set to logic 0, the A/D sampling control block 1026 will only generate a "start sample" control signal to the A/D sampling block 1060 to enable the A/D sampling process to commence when the Sending_Busy signal has been de-asserted by the control signal block 1024. As such, when the PARALLEL_OP register value is set to logic 0, the A/D sampling process for the current data acquisition cycle is commenced after the data encoding and output process of the current data acquisition cycle has been completed.

While the A/D sampling control blocks 1025 and 1026 are shown as separate blocks for ease of illustration of the process flow shown in FIG. 10, it is to be understood that such blocks 1025 and 1026 may collectively form one control module, e.g., a single AND gate, which asserts (logic 1) or de-asserts (logic 0) a "start sample" control signal at the output of the AND gate based on the logic level of the Sending_Busy signal and the value of the PARALLEL_OP register bit (e.g., two inputs to the single AND gate).

In some embodiments, an A/D sampling and memory loading process is performed as follows. The multiplexer block 1050 selects a first enabled channel, and the A/D sampling block 1060 samples the analog signal on the selected channel and loads the sampling result (digital samples) into a first memory location (e.g., first register) in the first memory array 1031. Then, the multiplexer block 1050 selects the next enabled channel, and the A/D sampling block 1060 samples the analog signal on the next selected channel and loads the sampling results into a second memory location (e.g., second register) in the first memory array 1031. The A/D sampling and memory loading process is performed for each enabled channel, wherein only digital samples pertaining to the enabled channels (as specified by the CHAN_ACTIVE register setting) are acquired and loaded into corresponding memory locations (e.g., registers) in the first memory array 1031.

When the data encoding/outputting and data sampling processes for the current data acquisition cycle are complete, the contents of the first memory array 1031 are transferred to the second memory array 1032, and then the chipset returns to a system ready state to await receipt of the next token which triggers a next data acquisition cycle. For example, as shown in FIG. 10, when the A/D sampling block 1060 completes the sampling and memory loading operations into the first memory array 1031, the A/D sampling block 1060 de-asserts the Sampling_Busy signal (e.g., switch to logic 0). In this circumstance, the A/D sampling block 1060 essentially outputs a "sampling not busy" signal to the first memory array 1031. In addition, as noted above, the control signal block 1024 de-asserts the Sending_Busy signal (e.g., switch to logic 0) to indicate that the data encoding and output process for the current data acquisition cycle is complete (i.e., sending not busy). As shown in FIG. 10, the output of the control signal block 1024 is input to the memory block 1030 to signal that "sending not busy." The memory block 1030 responds to the "sampling not busy" and "sending not busy" signals by transferring the contents of the first memory array 1031 to the second memory array 1032. In this regard, the digital samples for the current data acquisition cycle are stored in the second memory array 1032, wherein such digital samples are then encoded and output by the data encoding/output control block 1040 in the next data acquisition cycle.

FIG. 11 is a timing diagram which illustrates waveforms of token signals and control signals that are generated over a plurality of successive data acquisition cycles of the data acquisition system 1000 of FIG. 10 for a given chipset, according to an embodiment of the invention. In particular, FIG. 11 illustrates a first waveform 1100 of an incoming token signal that is generated by the token control block 514 (FIG. 5) and input to the token processing block 1010. A second waveform 1110 in FIG. 11 illustrates a System Busy signal that is generated by the system busy control block 1021. A third waveform 1120 illustrates a Sampling_Busy signal that is generated by the A/D sampling block 1060 and input to the system busy control block 1021 and the memory block 1030. A fourth waveform 1130 illustrates a Sending_Busy signal that is generated by the control blocks 1023 and 1024, and input to the control blocks 1025/1026, the memory block 1030, and the token output generator block 1013. A fifth waveform 1140 illustrates an outgoing token signal that is generated by the token output generator block 1013 and output to the token control block 514 (FIG. 5).

FIG. 11 illustrates each waveform 1100, 1110, 1120, 1130, and 1140 as generated over four successive data acquisition cycles of the data acquisition system 1000 of FIG. 10, with each data acquisition cycle being triggered/initiated by a low transitioning pulse of the incoming token signal 1100. The timing diagram of FIG. 11 assumes that the PARALLEL_OP register parameter is set to logic 1, which allows the data encoding/output and data acquisition/sampling operations to operate in parallel. When the token processing block 1010 detects a low transitioning pulse on the incoming signal waveform 1110, it is determined that token has been received to initiate a data acquisition cycle.

As shown in FIG. 11, in response to the detection of the incoming token, assuming the system is not busy, the Sampling_Busy signal 1120 and the Sending_Busy signal 1130 each transition to a logic high level (control signal asserted) to indicate that the A/D sampling and data encoding/outputting operations have been initiated. In addition, the System_Busy signal transitions from a logic high level to a logic low level, which indicates that the system went from a "not busy" state to a "busy" state in response to the initiation of the A/D sampling and data encoding/outputting operations. At some point in a given data acquisition cycle, the Sending_Busy signal 1130 transitions to logic low (de-asserted), indicating that the data encoding/outputting operation has completed. At that time, a low transitioning token pulse is generated on the outgoing token waveform 1140 to essentially pass the token back to the token controller to be sent to the next chipset in the chain. After the Sending_Busy signal 1130 is de-asserted, and the outgoing token 1140 is sent out, the A/D sampling process continues until some point in the data acquisition cycle wherein the Sampling_Busy signal 1120 is de-asserted indicating that the A/D sampling and memory loading operations are complete. With all data acquisition and outputting processes complete, the System_Busy signal 1110 is asserted to logic high, indicating that the system is in a ready state for commencing a next data acquisition cycle upon receipt of the next incoming token pulse on the incoming token signal waveform 1110.

Figure 12A:
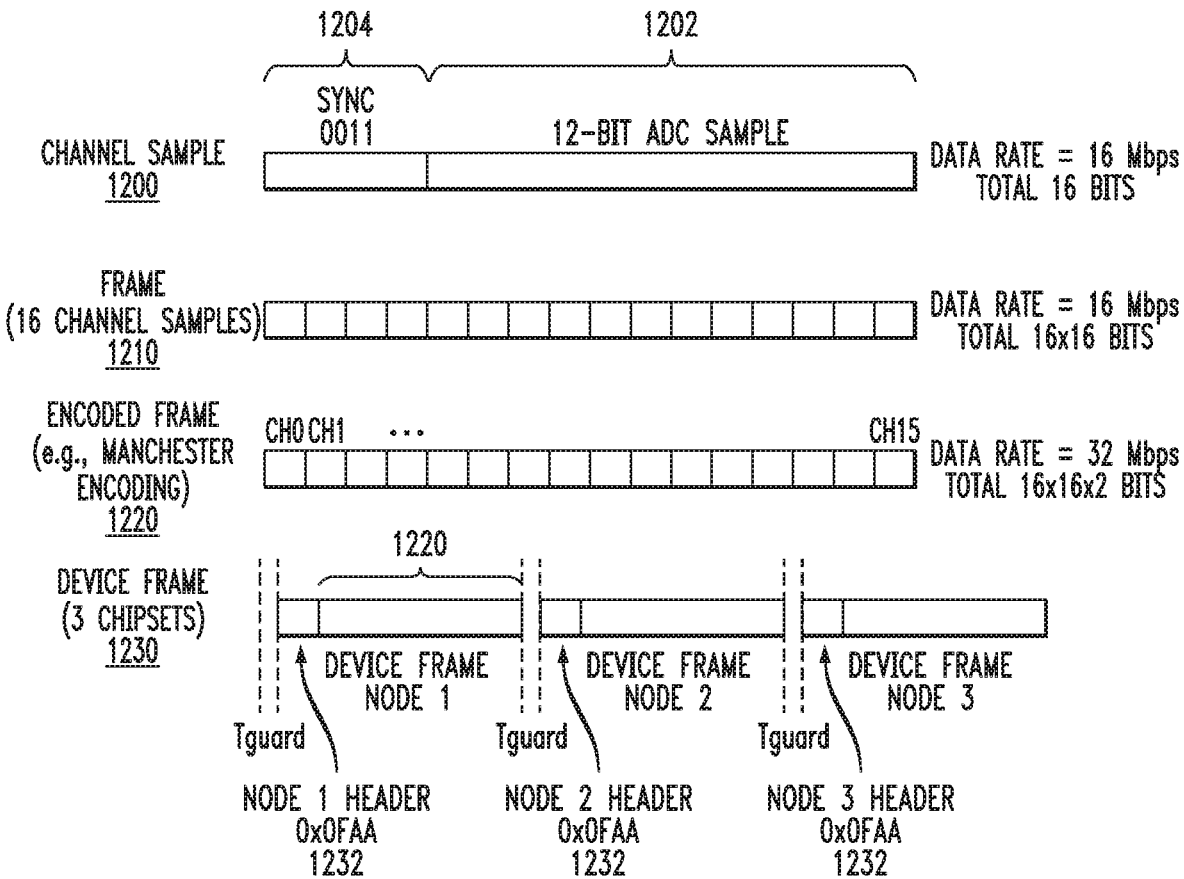
FIGS. 12A and 12B schematically illustrate data encoding and output functions of a data acquisition system, according to an embodiment of the invention.
Figure 12B:
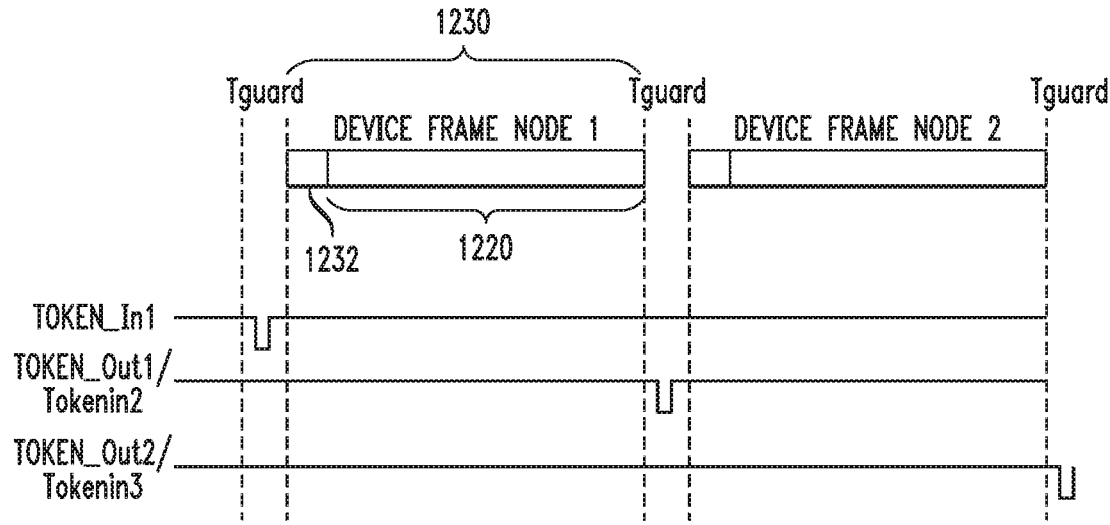

FIGS. 12A and 12B schematically illustrate data encoding and output functions of a data acquisition system according to an embodiment of the invention. More specifically, in some embodiments, FIGS. 12A and 12B schematically illustrate functions performed by the data encoding/output control block 1040 of FIG. 10. FIG. 12A schematically illustrates a channel sample 1200 which is stored in an associated memory location (e.g., register) in the second memory array 1032. The channel sample 1200 comprises an ADC sample block 1202, and a header 1204. In some embodiments, the ADC sample block 1202 is a 12-bit block of digital samples for a given channel, and the header 1204 is a 4-bit block comprising a predefined bit sequence (e.g., 0 0 1 1). In a 16-channel system such as shown in FIG. 10, there is one channel sample 1200 stored in the second memory array 1032 for each active channel that was sampled. If all 16 channels are sampled during a given data acquisition cycle, then 16 channel samples 1200 would be stored in the second memory array 1032 for encoding and output by the data encoding/output block 1040.

FIG. 12A further illustrates a frame structure 1210 which is generated by the data frame generator 1041. The frame structure 1210 is generated by concatenating the entire set of channel samples 1200 that were captured and stored in the second memory array 1032 during a previous data acquisition cycle. In FIG. 12A, the frame structure 1210 is shown to be a concatenation of 16 channel samples, under the assumption that all 16 channels were enabled active for sampling. However, the frame structure 1210 generated for the given chipset may have digital samples from less than all available channels in circumstances in which not all channels were enabled during the previous data acquisition cycle. FIG. 12A further illustrates an encoded frame structure 1220 which is similar to the frame structure 1210 in that there are 16 separate blocks of data, except that the number of bits in the encoded frame 1220 is doubled by virtue of the line coding, e.g., Manchester coding.

As further illustrated in FIG. 12A, a device frame 1230 for a given chipset (node) is generated by adding a synchronizing header 1232 to the beginning of the encoded frame 1220 for the given chipset (or node). In some embodiments, the synchronization header 1232 comprises a bit sequence of 0x0FAA, although other synchronization bit sequences can be implemented for the device frame header 1232. The device frame 1230 for each chipset (node) is transmitted over the high-speed data bus to the master controller in sequence, as per the token passing sequence discussed above for a given data acquisition cycle.

As shown in FIGS. 12A and 12B, a predetermined minimum period of time, referred to as "Tguard" is implemented between transmission of successive device frames 1230 to ensure proper synchronization between the chipsets receiving/generating tokens, and the sequential transmission of the device frames 1230. FIG. 12B illustrates a timing relationship between the input and output tokens (which control the data acquisition and transmission sequences of the various chipsets) and the device frames 1230 that are sequentially transmitted for the chipsets. In some embodiments, Tguard is specified to be more than 3 data clocks to ensure that there is no overlap between the input and output tokens and transmission of the device frames. In some embodiments, the period Tguard is defined by the register parameter Token_DLY, which specifies a number of data clock for the given chipset to send an output token to the next successive.

As noted above, the data acquisition blocks of the chipsets are configured to decouple the data sampling process from the data encoding/transmission process such that each chipset can continue with a data sampling process to acquire digital samples for each enabled channel in a current data acquisition cycle even when the data encoding/transmission process of the current data acquisition cycle has been completed. The data encoding/transmission process is performed to encode and transmit digital samples that were acquired during a previous data acquisition cycle, so the data encoding/transmission process for all chipsets can be performed and completed for a current data acquisition cycle, even when some of the chipsets are still operating to complete the data sampling process for the current data acquisition cycle. Each chipset outputs a token to the next chipset in the sequence (or back to the master controller from the last chipset in the chain) when the chipset completes its data encoding/transmission process for the given data acquisition cycle is completed.

In this regard, the overall data collection rate of the system will be limited by either of: (i) the token passage from the master controller to the first chipset in the sequence, which under normal operating conditions, will determine the overall sample rate of the system; (2) the A/D sampling process if the multiplexer is operating slow (high slew rate) or many channels for the chipsets are enabled, etc.; or (3) the data encoding/transmission process if there are many chipsets used to collect data, or the sending process is slow, etc. Ideally, the data sampling and data encoding/transmission processes should be configured to run fast enough such that the overall sample rate of the system is determined by the frequency of the token passage from the master controller to the first chipset in the chain.

Figure 13:
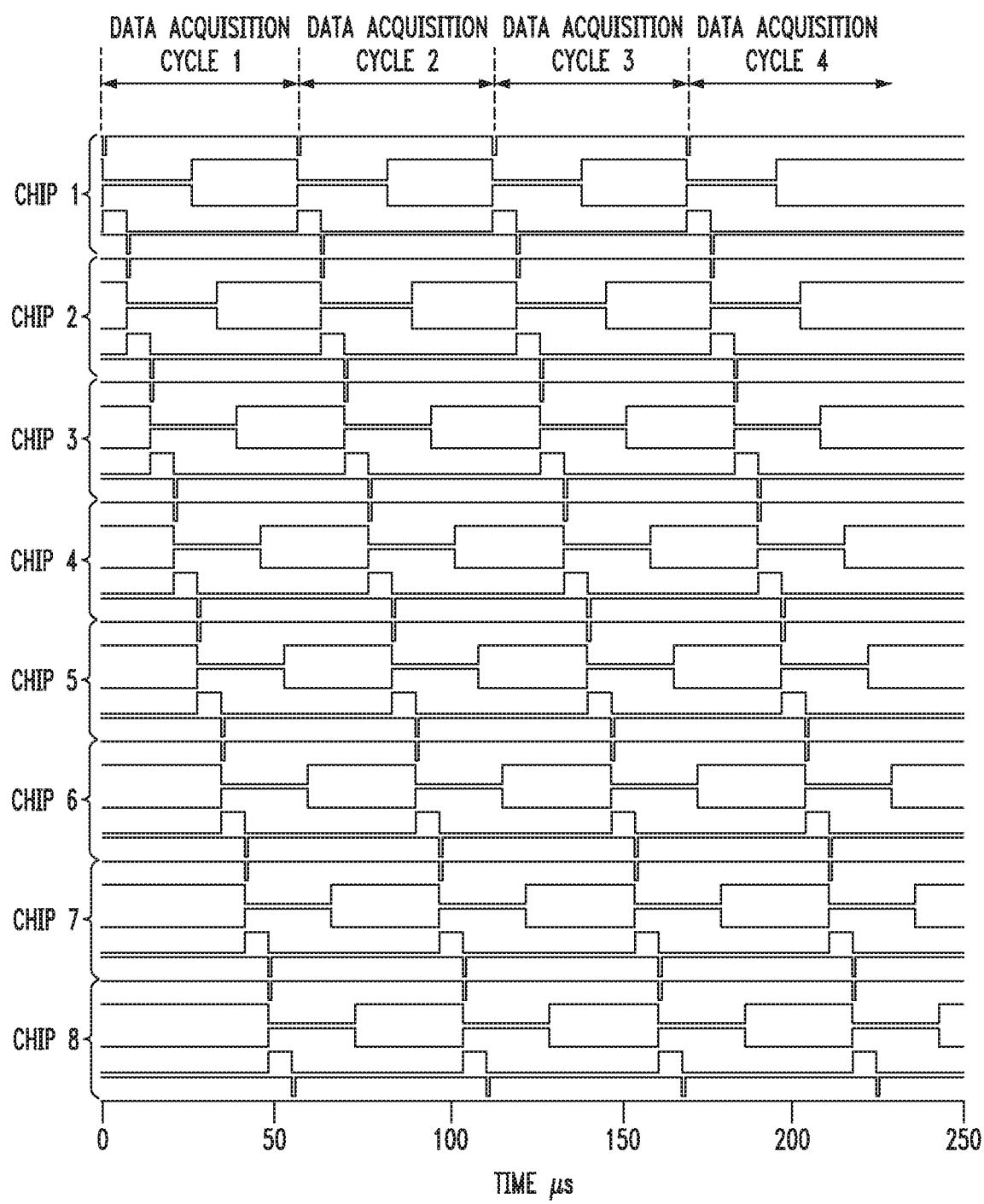
FIG. 13 is a timing diagram which illustrates waveforms of token signals and control signals that are generated over a plurality of successive data acquisition cycles of data acquisition systems for eight (8) chipsets, based on a first set of register-configurable channel settings, according to an embodiment of the invention.

FIG. 13 is a timing diagram which illustrates waveforms of token signals and control signals generated over a plurality of successive data acquisition cycles of data acquisition systems for eight (8) chipsets, according to an embodiment of the invention. In particular, the timing diagram shown in FIG. 13 comprises computer simulated waveforms that were generated for a system model defined as follows: (i) 8 chipsets with 16 channels per chipset; (ii) data clocks with clock frequencies of about 40 MHz (randomly setup in the simulation with about 1% tolerance); (iii) an ADC clock divider=4; (iv) LVDS clock divide=1; and (v) a multiplexer clock divider=ADC clock divider*16.

The timing diagram of FIG. 13 shows four successive data acquisition cycles initiated by the master controller 312 outputting a token control signal on the first token control line 342, which is input to the Token IN port of the first chipset (CHIP 1). As shown in FIG. 13, a maximum data collection rate (i.e., the frequency of outputting a control token on the first token control line 342 to initiate a data acquisition cycle) is limited by the data sending rate of all the chipsets (e.g., CHIP 1~CHIP 8). Indeed, as shown in FIG. 13, the passage of the control token on the Token OUT line of CHIP 8 (the last chipset in the chipset chain) after CHIP 8 completes a data output operation, can immediately trigger the initiation and execution of a next data acquisition cycle, assuming that the first chipset CHIP 1 is ready to commence the next data acquisition cycle upon receipt of the control token on the Token IN port of CHIP 1 after CHIP 8 completes the data output operation from the previous data collection cycle.

As shown in the timing diagram of FIG. 13, at the rates given above, the system is configured to simultaneously manage 128 data channels, with a maximum throughput determined by the data rates on the data lines, in this case being, 2.3 Msps overall, or 18 ksps per data channel. At 16 bit per sample, that amounts to 37 Mbps throughput rate on the data bus. Due to the dual bus architecture and the parallel nature of the sampling among the chipsets, combined with the serial communication on the data lines, the system can push very high sample rates through the data lines while simultaneously managing a very large number of channels. In the scenario shown, the samples are substantially over-sampled, such that they may be digitally filtered and compressed to decrease overall down-stream throughput requirements. In addition, by strategically converting, noise shaping, and down-sampling the samples, additional bit depth may be added to the system. This may allow the system to recover very low amplitude neural traffic, which may be band-limited, but very near in amplitude to the noise floor of the system.

Figure 14:
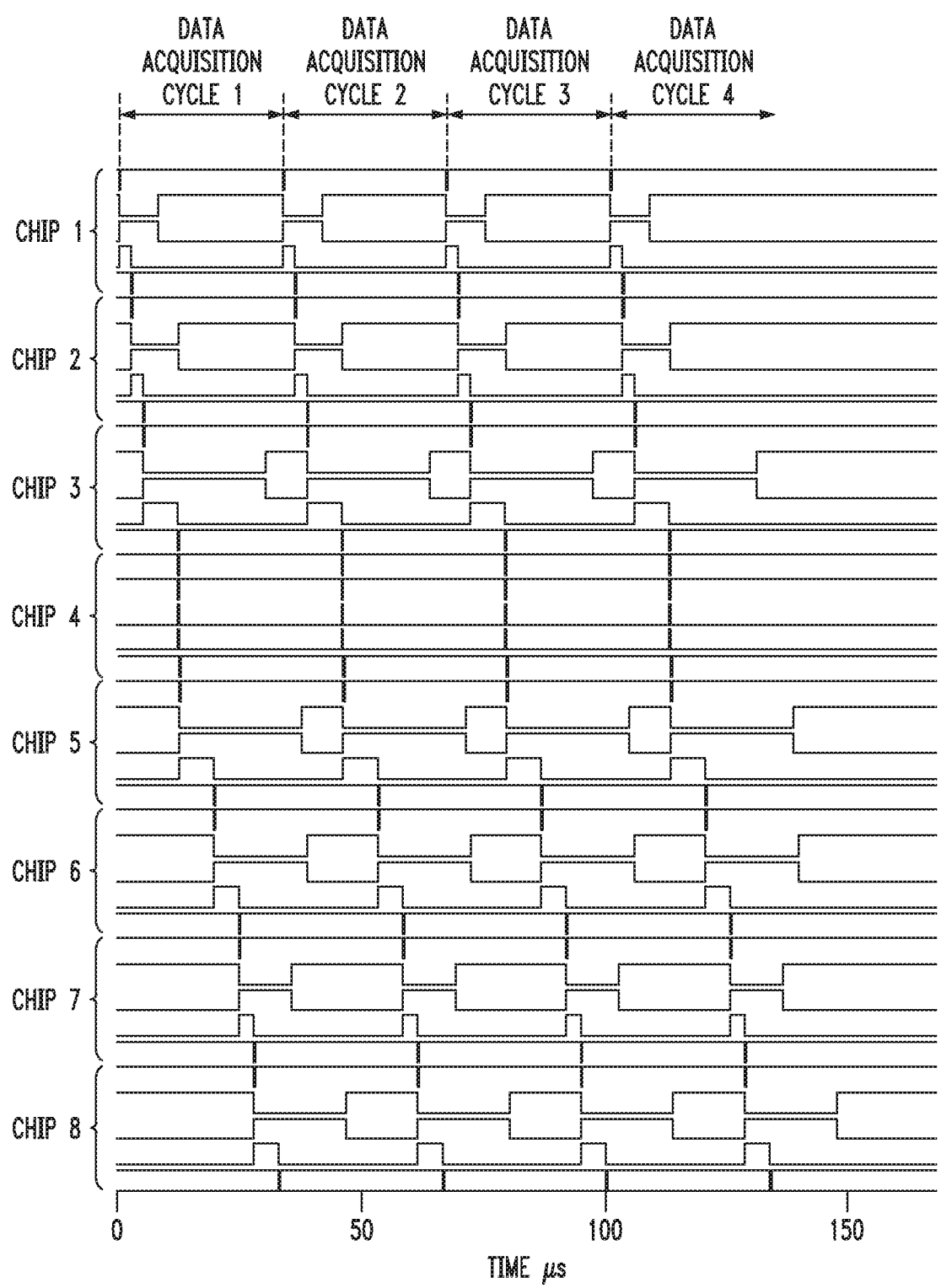
FIG. 14 is a timing diagram which illustrates waveforms of token signals and control signals that are generated over a plurality of successive data acquisition cycles of the data acquisition systems of eight (8) chipsets of FIG. 13, but based on a second set of register-configurable channel settings, according to an embodiment of the invention.

FIG. 14 is a timing diagram which illustrates waveforms of token signals and control signals that are generated over a plurality of successive data acquisition cycles of the data acquisition systems of eight (8) chipsets of FIG. 13, but based on a second set of register-configurable channel settings, according to an embodiment of the invention. In particular, the timing diagram of FIG. 14 is based on the same clock settings as noted above for the simulated model for the timing diagram of FIG. 13, but with the selection (enabling/disabling) of the signal channels varied as follows, where each line in the array corresponds to one of the chipsets, and entries in each line indicate which of the 16 sense electrodes for that chipset are enabled (1) or disabled (0):

chip_CH = [1 0 0 0 1 0 0 0 0 0 1 0 1 0 1;
1 1 0 0 0 1 0 0 1 1 1 0 0 0 0 0;
1 1 1 1 1 1 1 1 1 1 1 1 1 1 1 1;
0 0 0 0 0 0 0 0 0 0 0 0 0 0 0 0;
1 1 1 1 1 1 1 1 1 1 1 1 1 1 1 1;
1 1 1 1 1 0 0 1 0 1 1 1 1 0 1;
0 0 0 0 1 1 1 1 1 0 1 0 1 0 0 0;
1 1 1 0 1 0 1 0 0 1 1 1 1 1 1 1];

The example timing diagram of FIG. 14 illustrates that a higher per channel throughput (data collection rate) can be obtained for the same clock settings, when various signal channels across some or all of the chipsets are disabled (data not collected on the sense electrodes connected to disabled signal channels). In the example simulation of FIG. 14, it is shown that all the channels on CHIP 4 are turned off (no data to be sent). Therefore, for CHIP 4, in the simulation, a 16-bit synchronization header is the only data that is send, and then the token passes to the next chipset CHIP 5.

During a sensing application, the chipsets may be configured in a targeted mode, such that only interesting channels are enabled for capture. In such a scenario, the enabled channels may be oversampled by the system in order to recover more information from the channels, and increase the fidelity of the recovered signals.

Taking this to an extreme scenario, in one non-limiting example, a chipset may have a maximum internal sampling rate (mega samples per second ((Msps)) of 1 Msps, 2 Msps, 4 Msps, 8 Msps, or the like, and a bit depth of 10 bit, 12 bit, 14 bit, 16 bit, 18 it, 24 it, or the like. By way of example, if the system is configured such that only 1 channel in the system is enabled (or alternatively, 1 channel per chipset), that channel can be sampled at substantially the maximum sampling rate of the chipset. The resulting oversampled signal may then be decimated down to an appropriate sampling rate for the signal under study (i.e. down to 5 ksps, 3 ksps, 2 ksps, 1 ksps, 500 sps, etc.). Under such down sampling, with appropriate use of a noise shaping filter, the bit depth may be increased appropriately adding anywhere from 4-12 bits worth of depth to the captured signal. Such oversampling may be advantageous to recover exquisitely small signals which are riding along with large cardiac electrophysiologic signals and the like.

When the multiplexer and ADC circuitry operations do not cause any undue delay for a desired data collection rate, the clock rates of the multiplexer and ADC operations can be slowed down without impacting anything in terms of the overall system data rates, so that the timing of the ADC sampling and data output operations are more closely matched. To prevent having to wait for chips that are not finished yet, the master controller 312 can delay output of the control token by a desired delay (e.g., 3 µs) for each data acquisition cycle before outputting the token on the first token control line 342 back to the chipset array.

Some non-limiting examples and uses of the exemplary systems described herein are discussed below.

Example 1

Coronary Atrial and/or Ventricular Mapping

In some applications, it may be advantageous to monitor physiologic activity of one or more regions of a heart of a subject for diagnostic and/or therapeutic reasons. One or more systems as described herein may be used in such applications. In such applications, for example, monitoring the left or right atrium of a subject, a system as described herein may include a large number of sensors (i.e. more than 31, more than 127, more than 255, more than 511, more than 1023, or the like), wherein each sensor is deployably attached to the distal end of a catheter, so as to interface with tissues of the heart of the subject upon deployment therein. Such applications may benefit from extremely high spatial density of the electrodes so as to precisely target diseased regions of tissue, find local neural traffic, target regions for treatment, and the like. In such applications, a cardiac electrophysiological signal may be obtained from each sensor and directed through one or more processing modules, with potentially other signals combined therewith (such as movement artifacts, local neural traffic, far field signals, etc.).

The system may include one or more stimulation electrodes that are used to apply a stimulation to a location on or in the subject, wherein the sensors are configured to measure the stimulation signal and/or a local physiologic response thereto. In such applications, a stimulation electrode in the chamber of the heart may be pulsed periodically and measured by the sensors, wherein the amplitude and/or delay of the incoming signals relate to the spatial arrangement of electrodes in the chamber and/or the physiologic response to the stimulus.

The system may include one or more therapeutic elements (i.e. pacing elements, ablation elements, cutting implements, suction elements, ultrasound elements, etc.) so as to affect a region of tissue in the subject during a procedure, during use, etc. In such applications, the sensors may be configured to monitor the action of the therapeutic element directly, monitor the effect of the action of the therapeutic element on the surrounding tissues, physiologic response of the subject, or the like.

For such applications, electrophysiological signals may contain both low and intermediate frequency content, as caused by action and movement of the local cardiac tissues, as well as heterogeneously distributed neural traffic, which may be distributed throughout the monitored tissues, and be collected both temporally as well as spatially over time. The system may be configured in different modes, as described herein, to collect signals at many of the sites, to hone in on key sensors that are displaying relevant traffic during use, or the like.

In some non-limiting cardiac applications, the system may be configured to determine signal transit times between sites on the heart walls, between chambers, across regions of diseased tissue, or the like.

Example 2

Arterial Mapping

In some applications, it may be advantageous to interface with smooth muscle and nerves located in and in the vicinity of one or more vessels (i.e. arteries, veins, ureters, etc.), in a subject for diagnostic, mapping, and/or therapeutic reasons. One or more systems as described herein may be used in such applications. In such applications, for example, for monitoring one or more arteries serving an organ (i.e. a kidney, a pancreas, a spleen, a stomach, a liver, a gastrointestinal track element, an esophagus, a thyroid, a testicle, a uterus, etc.), a system as described herein may include a small to moderate number of sensors (i.e. more than 7, more than 015, more than 31, less than 63, less than 127, less than 255, or the like) which are deployably attached to the distal end of a catheter, so as to interface with tissues of the vessel of the subject upon deployment therein (i.e. both circumferentially around the vessel wall but optionally axially along the vessel, through the walls, etc. as described in various patent applications that are incorporated by reference herein, etc.). In such applications, the target anatomy and associated neural traffic is generally heterogeneously distributed, such that some sensors may see little to no traffic at a target placement site, while other sensors may see a significant amount of traffic at another placement site during use. It is also possible that sensors are in proximity to valid traffic, but the signal amplitudes of such traffic is particularly low (i.e. less than 20 uV, less than 10 uV, less than 5 uV, less than 2 uV, etc.).

In such applications the system may be configured in a seek mode, wherein the sensors are scanned in parallel to determine which have useful information and which do not, and switched to a targeting mode that hones in on the channels that are obtaining useful information, so as to improve the signal fidelity on those channels, while disabling the channels that are (at that moment), not obtaining useful signal. In this manner, the system may increase the fidelity on target sites, so as to obtain exquisitely small signals, which are relevant to the usage scenario at hand.

As with previous examples, the system may be used in combination with other diagnostic and/or therapeutic elements, so as to monitor actions provided thereby, monitor the physiologic response, thereto, etc. Additional details regarding such arrangements are further described in PCT Application Serial No. PCT/US2013/023157, filed on Jan. 25, 2013 and entitled Controlled Sympathectomy and Micro-Ablation Systems and Methods," PCT Application Serial No. PCT/US2013/042847, filed May 28, 2013 and entitled "Endoscopic Sympathectomy Systems and Methods," PCT Application Serial No. PCT/US2013/073844, filed Dec. 9, 2013 and entitled "Systems and Methods for Regulating Organ and/or Tumor Growth Rates, Function and/to Development," PCT Application Serial No. PCT/US2014/031962, filed Mar. 27, 2014 and entitled "Systems and Methods for Neurological Traffic and/or Receptor Functional Evaluation and/or Modification," PCT Application Serial No. PCT/US2014/060471, filed Oct. 14, 2014 and entitled "Systems and Methods for Treating Cancer and/or Augmenting Organ Function," PCT Application Serial No. PCT/US2015/063473, filed Dec. 3, 2015 and entitled "Systems and Methods for Treating Cancer and/or Augmenting Organ Function," PCT Application Serial No. PCT/US2015/063858, filed Dec. 4, 2015 and entitled "Systems and Methods for Regulating Organ and/or Tumor Growth Rates, Function and/or Development," which are incorporated herein by reference.

Example 3

Parenchymal Mmonitoring

In some applications, it may be advantageous to interface with vessels, structures, and the like within one or more organs of a subject. In such applications, electrophysiological signals generated by local tissues, organ functions, smooth muscles, and nerves located in and in the vicinity of one or more miniature vessels (i.e. arteries, veins, ureters, etc. within the parenchyma of an organ), may be monitored by a system as described herein, in a subject for diagnostic, mapping, and/or therapeutic reasons.

In such applications, the distal tip of the system may be formed so as to fit delicately within the small vessels of the target organ, so as to deliver one or more of the sensors to the target monitoring sites. In such applications, for example, for monitoring one or more arteries or microvessels within an organ (i.e. a kidney, a pancreas, a spleen, a stomach, a liver, a gastrointestinal track element, an esophagus, a thyroid, a testicle, a uterus, etc.), a system as described herein may include a small to moderate number of sensors (i.e. more than 2, more than 7, more than 15, less than 17, less than 65, less than 129, or the like) which are deployably attached to the distal end of a catheter, so as to interface with tissues along the walls and in the vicinity of one or more micro vessel of the subject upon deployment therein (i.e. both circumferentially around the vessel wall but optionally axially along the vessel, through the walls, etc. as described in previous patent applications that are incorporate by reference herein, etc.).

In such applications, the signals may be sparsely situated spatially throughout the target tissues, such that only a few of the sensors may obtain relevant physiologic signals at any given time during use. Also, the sensors themselves may be constructed particularly small so as to allow for navigation of the tortuous pathway to the target tissues, as well as to give a very precise localized map of electrophysiological activity in the nearby tissues. In general, the signals may be exceptionally small in such applications (i.e. less than 10 uV, less than 5 uV, less than 1 uV, or the like), and movement noise and other artifacts may be equivalently small compared with other application areas.

In such applications, one or more channels in the system may be configured so as to tune to a particularly narrow bandwidth (i.e. 500-2 kHz, 300-3 kHz, 200-5 kHz, etc.), and the processing modules and/or controller may be configured so as to filter the incoming signals, noise shape, etc. so as to reduce the noise floor to less than 1 uV, less than 0.5 uV, less than 0.25 uV, or the like. Furthermore, the system may include one or more signal extraction algorithms so as to extract one or more of the obtained signals from the noise floor during use.

As with previous examples, the system may be used in combination with other diagnostic and/or therapeutic elements, so as to monitor actions provided thereby, monitor the physiologic response, thereto, etc. Further details of such arrangements are described in PCT Application Serial No. PCT/US2013/067726, filed Oct. 31, 2013 and entitled "Systems and Methods for Treatment of Tissues Within and/or Through Lumen Wall," which is incorporated by reference herein, as well as in other PCT applications listed above which are incorporated by reference herein.

Example 4

Combined Use

In some applications, a multi-modal sensory configuration may be facilitated by a device in accordance with the present disclosure. In such applications, a plurality of sensors may be combined to provide additional functionality, such as fractional flow reserve functionality, arterial pressure sensing functionality, ultrasound sensing transducing functionality, or the like. Additional details regarding such arrangements are further described in the above-referenced PCT Application Serial No. PCT/US2016/052909, filed on Sep. 21, 2016 and entitled "Smart Torquer and Methods of Using Same," which is incorporated by reference herein, as well as in other PCT applications listed above which are incorporated by reference herein.

Example 5

Robotic Application

In some consumer and industrial applications, such as robotic applications, automotive applications, drone applications, or the like, wherein a combination of severe space limitations along with a need for a large number or sensors or transducers (i.e. tactile sensors, temperature sensors, touch sensors, accelerometers, electric field sensors, magnetic field sensors, etc.), may include functionality that may be facilitated by a system in accordance with the present disclosure. In some non-limiting applications, the system may be configured such that a plurality of such sensors or actuators are arranged at a peripheral site in the system, the wire bundle is provided to couple the peripheral site to a more central site, an intermediate controller, etc. such as the appendage, conduit, or the like through which the wire bundle passes is considerably space constrained, or requires reasonable levels of flexibility such that the size and flexibility of the bundle is important to the operation and reliability of the overall sensory system. In such applications, the data needed to be collected from the peripheral site may be considerable and dynamic, the overall data throughput rates may change during the course of time, and the importance of one or more sensors/transducers at the peripheral site may change considerably over time during use. In such applications, the system may be ideally suited for managing such peripheral sensing sites, while limiting the complexity of the interface for a host controller, or the like.

Example 6

Wearable Computing Applications and Human Machine Interfaces

In several different wearable computing applications and human machine interface applications, a similar need for the medical applications discussed above may arise. Some non-limiting examples of such applications include virtual reality and augmented reality systems, haptic interfaces, tactile feedback devices, tactile feedback clothing and interfaces, photodetector arrays, kinematic and/or kinetic sensor arrays, blast profile monitoring devices, and the like. Such systems may include a plurality of sensory input or actuators such that a system such as described herein may be suitable to monitor the sensory channels in real-time while interacting with actuators and the like. In such applications there is a strong need to limit the size of the associated hardware and to limit the complexity of the interface between portions of the system. At the same time, such systems generally must interact with a subject or the surrounding environment in a highly responsive manner, both with limited temporal lag, as well as with suitable fidelity so as to algorithmically react to the data being collected by the sensor channels.

Example 7

Prosthetic Interfaces

In several medical prosthetic applications, a system such as described herein may be suitable for interacting with a large number of sensors (tactile, kinematic, kinetic, electrophysiological, etc.), affixed to the subject, or integrated into the prosthetic so as to collect and react to a spatially robust array of sensors during use. In such applications there is a need to limit the amount of hardware and complexity of the interconnects between hardware components in the system such that a system in accordance with the present disclosure may be suitable for providing such interfaces between a host controller and a sensor rich site (such as an interface between a subject stump and a prosthesis, a surface on the prosthesis, a region on a subject where electrophysiological activity is to be harvested, etc.).

Example 8

CNS Application Example

In some applications, it may be advantageous to monitor physiologic activity, in particular neural traffic associated with one or more regions of the central nervous system of a subject for diagnostic and/or therapeutic reasons. One or more systems as described herein may be used in such applications for, e.g., monitoring the activity of nerve cells in deep parts of the brain such as the basal ganglia and the substantia nigra (i.e. so as to guide a therapy, map activity, or locating pacing sites for neurologic conditions such as Parkinson's disease, seizures, etc.). Nerve cells in the substantia nigra produce the neurotransmitter dopamine and are responsible for relaying messages that plan and control body movement of a subject.

A system as described herein for this application may include a moderate to large number of sensors (i.e. more than 31, more than 127, more than 255, more than 511, more than 1023, or the like) which are deployably attached to the distal end of a catheter, so as to interface with tissues of the brain of the subject upon deployment therein. The sensors and substrates upon which they are attached, may be substantially pliable so as to allow for a flexible distal tip to a diagnostic or therapeutic catheter as described herein, such that a user can navigate them through the tortuous vessels to a potential treatment site (i.e. up a vein, artery, or through tissue, etc. so as to reach the target site). Such applications may benefit from extremely high spatial density of the electrodes so as to precisely target diseased regions of tissue, find and characterize local neural traffic, target regions for treatment, and the like. In such applications, local neural action potentials, as well as local field potentials, and electrophysiological signal may be obtained from each sensor and directed through one or more processing modules the combination of which may be valuable to the tracking of the particular CNS disorder under study.

Example 9

Bladder and Lower Urinary Tract (LUT) Applications

In some applications, a combination of smooth muscle and neural traffic activity may be monitored during a procedure, placement of a neurostimulation lead(s), administration or injection of an agent, a neuro-ablative agent, a neurotoxin, or the like. In particular, gastrointestinal and LUT disorders may be studied using a system in accordance with the present disclosure. In such applications, the electrophysiologic signals may be collected in combination with movement related information as well as secondary sensory information such as local electromechanical effects (i.e. bladder pressure, local wall stretch, wall contact forces, etc.), during a procedure or the like. In such applications, the smooth muscle may generally be very compliant, such that the contact forces must be limited so as to limit the effect of the local sensors on the electrophysiologic function of the target tissues during measurement. Furthermore, the electrophysiological signals may contain a combination of low frequency and very low frequency signals from nearby smooth muscle activity, which may also contain very high amplitude signal content, in combination with very spatially heterogeneously distributed neural traffic, including intermediate very low amplitude content (i.e. local field potentials), as well as high frequency generally low amplitude content (i.e. neural action potentials and single/multi-unit neural activity), simultaneously. In such applications, the system described herein may be tuned such that channels track, with high gain, the slow moving, large amplitude smooth muscle signals, while capturing the intermediate and high frequency neural traffic with high fidelity. Additional details regarding such arrangements are further described in PCT Application Serial No. PCT/US2013/045605, filed on Jun. 13, 2013 and entitled "Devices, Systems, and Methods for Diagnosis and Treatment of Overactive Bladder," which is incorporated herein by reference.

Example 10

Pulmonary Vein Mapping

In applications related to atrial fibrillation, it may be advantageous to precisely ablate regions of the pulmonary veins and the veins and/or at sites where the pulmonary veins enter the left atrium of a subject. Such applications may benefit from any one of, finding traffic sites with high spatial precision, determining the locations of an abnormal or reentrant signal source, mapping neural traffic along the walls of the pulmonary vein, simultaneously mapping neural and cardiac traffic around the left atrium near the pulmonary veins, or the like. Such applications may be somewhat similar to the cardiac monitoring applications described in example 1, but may include different sensor arrangements so as to better conform to the target anatomy in and around the pulmonary veins. As such, pulmonary vein monitoring and mapping applications may include hybrid signal mapping requirements between cardiac mapping applications and vessel based mapping applications. Such systems may be ideal for finding suitable ablation sites, monitoring ablation completion, monitoring ablation affected zones, monitoring changes in traffic patterns during and after an ablation is completed, and the like.

Example 11

Coronary Artery Mapping

Particular examples of coronary artery mapping and therapies are described in PCT Application Serial No. PCT/US2016/057875, filed on Oct. 20, 2016 and entitled "Controlled and Precise Treatment of Cardiac Tissues," which is incorporated herein by reference. Such systems as described herein may be ideally suited for such mapping applications. In such applications, a low to moderate number of sensors may be used to find hot spots, find regions of vessels with high basal traffic, find areas with respond to physiologic stimuli, monitor response to stimulation, therapy, and the like. In such systems, the distal tip is generally constructed such that the processing modules would be arranged within the chambers of the heart or proximal vessels, while the sensory distal tip is arranged so as to fit into, navigate through, and interface with the walls of the coronary arteries or veins.

Example 12

Implant Applications

In several pacing and neural stimulation applications, it may be advantageous to monitor physiologic and/or electrophysiological signals from the target anatomy, so as to guide therapy, stimulation, adjust stimulation profiles, etc. In such applications, the array of sensors and/or electrodes may be placed in a distal unit (i.e. a distal tip), for interfacing with the target anatomy, target nerves, around or within a target vessel, etc. In such systems, a neural control unit may be located in a nearby tissue site or the like. In such systems, the need for very small, flexible, and simplistic interfaces, while affording a larger number of monitoring sites can be very valuable. A system as described herein may be advantageous for providing a wide, yet spatially precise electrophysiological monitor from a wide array of sensors, while affording a very simple and highly adaptable control interface for the implanted array.

Although illustrative embodiments of the present invention have been described herein with reference to the accompanying figures, it is to be understood that the invention is not limited to those precise embodiments, and that various other changes and modifications may be made therein by one skilled in the art without departing from the scope of the appended claims.

What is claimed is:

1. A medical device, comprising:
  a control system;
  a plurality of processing modules; and
  a wire bundle connecting the control system to the plurality of processing modules, wherein the wire bundle comprises control lines and data lines;
  wherein each processing module is coupled to a respective set of sensors arranged to interface with a biological tissue site, wherein the sensors are configured to capture analog physiological signals generated from the biological tissue site;
  wherein the control system is configured to generate a control signal on the control lines to initiate a data collection cycle by the plurality of processing modules;
  wherein in response to the control signal, each processing module of the plurality of processing modules is configured to perform a respective data collection process which comprises (i) capturing and processing an analog physiological signal on each enabled sensor in the respective set of sensors coupled to the processing module to generate a data sample for each analog physiological signal captured on each enabled sensor, and (ii) outputting data samples to the control system on the data lines;
  wherein the control lines comprise a bi-directional control bus comprising two control lines;

wherein the control system is configured as master device on the bi-directional control bus;

wherein each processing module is configured as a slave device on the bi-directional control bus;

wherein each processing module comprises control registers with configuration data to control functions of the processing modules; and wherein the control system communicates with the processing modules on the bi-directional control bus to read configuration data from, and write configuration data to, the control registers of the processing modules.

2. The medical device of claim 1, wherein the control registers of each processing module comprise (i) a control register with configuration data that instructs the processing module to selectively enable or disable individual sensors in the respective set of sensors for capturing and processing analog physiological signals and (ii) a control register with configuration data that instructs the processing module to adaptively increase a data throughput rate for signal channels coupled to enabled sensors.

3. The medical device of claim 1, wherein communication over the control lines and the data lines is asynchronous such that the control system can change the functionalities of the processing modules by issuing control commands on the control lines without interrupting the communication of data samples on the data lines by the processing modules.

4. The medical device of claim 1, wherein each processing module comprises:

amplifier circuitry configured to amplify the analog physiological signals captured on the respective set of sensors of the processing module, wherein the amplifier circuitry comprises multiple parallel amplifier channels, wherein each amplifier channel is configured to amplify the analog physiological signal captured on a respective one of the sensors of the set of sensors, and generate an amplified physiological signal;

a multiplexer circuit connected to outputs of the amplifier channels;

analog-to-digital conversion (ADC) circuitry connected to an output of the multiplexer circuit; and data output control circuitry connected to at least one data line of the data lines;

wherein the multiplexer circuit is configured to sequentially connect the amplified physiological signals at the outputs of the amplifier channels to an input of the ADC circuitry;

wherein the ADC circuitry is configured to (i) sequentially receive the amplified physiological signals for each sensor which are selectively output from the multiplexer circuit, and (ii) digitally sample the amplified physiological signals output from the amplifier circuitry and generate a separate block of digital samples for each amplified physiological signal output from the amplifier circuitry; and wherein the data output control circuitry is configured to encode the blocks of digital samples generated by the ADC circuitry and output the encoded blocks of digital samples on the at least one data line.

5. A medical device, comprising:
a control system;
a plurality of processing modules; and
a wire bundle connecting the control system to the plurality of processing modules, wherein the wire bundle comprises control lines and data lines;
wherein each processing module is coupled to a respective set of sensors arranged to interface with a biological tissue site, wherein the sensors are configured to capture analog physiological signals generated from the biological tissue site;

wherein the control system is configured to generate a control signal on the control lines to initiate a data collection cycle by the plurality of processing modules;

wherein in response to the control signal, each processing module of the plurality of processing modules is configured to perform a respective data collection process which comprises (i) capturing and processing an analog physiological signal on each enabled sensor in the respective set of sensors coupled to the processing module to generate a data sample for each analog physiological signal captured on each enabled sensor, and (ii) outputting data samples to the control system on the data lines;

wherein each processing module comprises:
amplifier circuitry configured to amplify the analog physiological signals captured on the respective set of sensors of the processing module, wherein the amplifier circuitry comprises multiple parallel amplifier channels, wherein each amplifier channel is configured to amplify the analog physiological signal captured on a respective one of the sensors of the set of sensors, and generate an amplified physiological signal;

a multiplexer circuit connected to outputs of the amplifier channels;

analog-to-digital conversion (ADC) circuitry connected to an output of the multiplexer circuit;

data output control circuitry connected to at least one data line of the data lines; and a memory block comprising a first memory array, and a second memory array;

wherein the multiplexer circuit is configured to sequentially connect the amplified physiological signals at the outputs of the amplifier channels to an input of the ADC circuitry;

wherein the ADC circuitry is configured to (i) sequentially receive the amplified physiological signals for each sensor which are selectively output from the multiplexer circuit, and (ii) digitally sample the amplified physiological signals output from the amplifier circuitry and generate a separate block of digital samples for each amplified physiological signal output from the amplifier circuitry;

wherein the data output control circuitry is configured to encode the blocks of digital samples generated by the ADC circuitry and output the encoded blocks of digital samples on the at least one data line;

wherein the first memory array is configured to store blocks of digital samples generated by the ADC circuitry during a current data collection cycle initiated by the control system; and wherein the second memory array is configured to store blocks of digital samples generated by the ADC circuitry during a previous data collection cycle previously initiated by the control system.

6. The medical device of claim 5, wherein during a current data collection cycle initiated by the control system, the data output control circuitry is configured to encode and output the blocks of digital samples stored in the second memory array, while the ADC circuitry generates and stores the blocks of digital samples for the current data collection cycle in the first memory array.

7. The medical device of claim 5, wherein the first memory array comprises a first register array and the second memory array comprise a second register array, wherein the first and second register arrays each comprise a separate register for each amplifier channel to store respective blocks of digital samples associated with the respective amplifier channels.

8. A medical device, comprising:
a control system;
a plurality of processing modules; and
a wire bundle connecting the control system to the plurality of processing modules, wherein the wire bundle comprises control lines and data lines;
wherein each processing module is coupled to a respective set of sensors arranged to interface with a biological tissue site, wherein the sensors are configured to capture analog physiological signals generated from the biological tissue site;
wherein the control system is configured to generate a control signal on the control lines to initiate a data collection cycle by the plurality of processing modules;
wherein in response to the control signal, each processing module of the plurality of processing modules is configured to perform a respective data collection process which comprises (i) capturing and processing an analog physiological signal on each enabled sensor in the respective set of sensors coupled to the processing module to generate a data sample for each analog physiological signal captured on each enabled sensor, and (ii) outputting data samples to the control system on the data lines;
wherein each processing module comprises:
amplifier circuitry configured to amplify the analog physiological signals captured on the respective set of sensors of the processing module, wherein the amplifier circuitry comprises multiple parallel amplifier channels, wherein each amplifier channel is configured to amplify the analog physiological signal captured on a respective one of the sensors of the set of sensors, and generate an amplified physiological signal;
a multiplexer circuit connected to outputs of the amplifier channels;
analog-to-digital conversion (ADC) circuitry connected to an output of the multiplexer circuit;
data output control circuitry connected to at least one data line of the data lines; and
wherein the multiplexer circuit is configured to sequentially connect the amplified physiological signals at the outputs of the amplifier channels to an input of the ADC circuitry;
wherein the ADC circuitry is configured to (i) sequentially receive the amplified physiological signals for each sensor which are selectively output from the multiplexer circuit, and (ii) digitally sample the amplified physiological signals output from the amplifier circuitry and generate a separate block of digital samples for each amplified physiological signal output from the amplifier circuitry;
wherein the data output control circuitry is configured to encode the blocks of digital samples generated by the ADC circuitry and output the encoded blocks of digital samples on the at least one data line;
wherein the data output control circuitry comprises:
a data frame generator configured to generate a data frame for each block of digital samples;
a serializer and encoder circuit configured to combine the data frames into a device frame and line encode the device frame for transmission over the at least one data line; and
data line driver circuitry configured to output the device frame on the at least one data line.

9. The medical device of claim 1, wherein:
the plurality of processing modules includes N processing modules arranged in a sequence starting from a first processing module to an $N^{th}$ processing module;
the control lines comprise a first token control line and a second token control line;
each processing module comprises a Token IN port and a Token OUT port;
the first token control line is connected to a Token OUT port of the control system and to the Token IN port of the first processing module;
the second token control line is connected to the Token OUT port of the $N^{th}$ processing module and to a Token IN port of the control system; and
the Token OUT port of each processing module in the sequence from the first processing module to the $N^{th}-1$ processing module is connected to the Token IN port of a next successive processing module by a respective chip-to-chip token control line, thereby forming the sequence of processing modules from the first processing module to the $N^{th}$ processing module.

10. The medical device of claim 9, wherein:
a sequence and timing of operations performed by the processing modules are controlled using a token-based protocol in which a control token is output on the first token control line from the control system to the first processing module;
the control token is passed downstream to each successive processing module in the sequence via the chip-to-chip token control line;
each processing module performs one or more operations when holding the control token, and when the one or more operations are completed, the processing module passes the control token to the next successive processing module to initiate the same one or more operations in the next successive processing module; and
in response to the $N^{th}$ processing module completing the same one or more operations, the $N^{th}$ processing module passes the control token back to the control system on the second token control line, which indicates to the control system that a current operation cycle is complete.

11. The medical device of claim 10, wherein the token-based protocol is implemented by the control system to dynamically assign a unique Device ID address to each processing module.

12. The medical device of claim 10, wherein:
the token-based protocol is implemented to initiate and control the data collection cycle implemented by the processing modules;
wherein the control signal that is generated by the control system comprises a token control signal on the first token control line; and
each processing module is configured to perform the respective data collection process when the processing module is holding the token control signal.

13. The medical device of claim 1, wherein one or more of the sensors comprises one of a sense electrode, an accelerometer, a force sensor, a tactile sensor, a strain sensor, a temperature sensor, a magnetic sensor, a fluid analyte sensor, and a flow sensor.

14. A medical device, comprising:
a control system;
a plurality N of processing modules arranged in a sequence starting from a first processing module to an $N^{th}$ processing module; and
a wire bundle connecting the control system to the plurality of processing modules, wherein the wire bundle comprises (i) control lines comprising a shared bi-directional control bus, a first token control line, and a second token control line, and (ii) data lines comprising a shared digital data bus;
wherein each processing module is coupled to a respective set of sensors arranged to interface with a biological tissue site, wherein the sensors are configured to capture analog physiological signals generated from the biological tissue site;
wherein each processing module comprises a Token IN port and a Token OUT port;
wherein the first token control line is connected to a Token OUT port of the control system and to the Token IN port of the first processing module;
wherein the second token control line is connected to the Token OUT port of the $N^{th}$ processing module and to a Token IN port of the control system;
wherein the Token OUT port of each processing module in the sequence from the first processing module to the $N^{th}-1$ processing module is connected to the Token IN port of a next successive processing module by chip-to-chip token control lines; and
wherein the control system is configured to generate a token signal on the first token control line which is sequentially passed to each processing module to perform a current data collection cycle by the plurality of processing modules, and then passed back to the control system from the $N^{th}$ processing module on the second token control line to indicate to the control system that the current data collection cycle is complete.

15. The medical device of claim 14, wherein in response to receipt of the token signal at the Token IN port of a given processing module from one of the control system and an upstream processing module, the given processing module is configured to perform a respective current data collection process which comprises (i) amplifying an analog physiological signal captured on each sensor of the set of sensors to generate a set of amplified physiological signals, (ii) digitally sampling each of the amplified physiological signals to generate a separate block of digital samples for each amplified physiological signal, and (iii) digitally encoding and outputting blocks of digital samples, which were generated during a previous data collection cycle, on the shared digital data bus to the control system.

16. The medical device of claim 15, wherein:
the control system is configured to generate a control command on the shared bi-directional control bus, which is addressed to one or more of the processing modules, to dynamically adjust at least one operating parameter of a least one of the amplifying, a digital sampling, the encoding, and outputting operations of the one or more processing modules;
each processing module outputs a corresponding token control signal on the Token OUT port of the processing module upon completion of the encoding and outputting operations, irrespective of whether the digital sampling is complete; and
each processing module further comprises:
a memory block comprising a first memory array, and a second memory array;
wherein the first memory array is configured to store blocks of digital samples generated by the processing module during the current data collection cycle; and
wherein the second memory array is configured to store blocks of digital samples generated by the processing module during the previous data collection cycle.

17. A catheter, comprising:
a control system;
a plurality of processing modules;
a plurality of sensors, wherein subsets of the plurality of sensors are connected to respective processing modules, wherein each sensor is configured to capture physiological signals generated in biological tissue; and
a wire bundle comprising wires connecting the control system to the plurality of processing modules, the wires comprising control lines and data lines;
wherein the catheter is structurally configured as an elongate structure, arranged with a distal end adapted for placement into a subject, and a proximal end structurally configured as a handle which is configured to interface with an operator;
wherein the plurality of sensors and processing modules are arranged at the distal end of the catheter, with the sensors configured and arranged to interface with at least one biologic tissue;
wherein the control system is disposed at the proximal end of the catheter;
wherein the plurality of processing modules includes N processing modules arranged in a sequence starting from a first processing module to an $N^{th}$ processing module;
wherein the control lines comprise a first token control line and a second token control line;
wherein each processing module comprises a Token IN port and a Token OUT port;
wherein the first token control line is connected to a Token OUT port of the control system and to the Token IN port of the first processing module;
wherein the second token control line is connected to the Token OUT port of the $N^{th}$ processing module and to a Token IN port of the control system; and
wherein the Token OUT port of each processing module in the sequence from the first processing module to the $N^{th}-1$ processing module is connected to the Token IN port of a next successive processing module by a respective chip-to-chip token control line, thereby forming the sequence of processing modules from the first processing module to the $N^{th}$ processing module.

18. The catheter of claim 17, wherein a ratio of a number of the sensors to a number of the wires of the wire bundle is greater than one of a ratio of 1.5:1, a ratio of 2:1, a ratio of 4:1, a ratio of 16:1, a ratio of 64:1, and a ratio of 128:1.

19. The catheter of claim 17, wherein a ratio of a number of the sensors to a number of the processing modules is greater than or equal to one of a ratio of 2:1, a ratio of 4:1, a ratio of 8:1, a ratio of 16:1, and a ratio of 32:1.

20. The catheter of claim 17, further comprising:
at least one of (i) one or more stimulation electrodes and (ii) one or more therapeutic effectors;
wherein the physiological signals captured by the sensors are related to actions of the at least one of (i) one or more of stimulation electrodes and (ii) one or more of therapeutic effectors on the at least one biologic tissue during operation.

21. The catheter of claim 17, wherein:
the control system is configured to initialize and adapt functionalities of the processing modules via the control lines;
the processing modules are configured to generate samples from the sensors and communicate the samples to the control system via the data lines;
communication over the control lines is implemented using a bi-directional 2-wire bus; and
communication over the data lines is implemented using a high-speed 2-wire differential bus.

22. The catheter of claim 17, wherein:
the control system is configured to initialize and adapt functionalities of the processing modules via the control lines;
the processing modules are configured to generate samples from the sensors and communicate the samples to the control system via the data lines; and
communication over the control lines and the data lines is asynchronous such that the control system can change the functionalities of the processing modules by issuing control commands on the control lines without interrupting the communication of samples on the data lines by the processing modules.

23. The catheter of claim 22, wherein a collective sample rate of the processing modules is substantially independent of a number of sensors enabled by the processing modules during use of the catheter.

24. The catheter of claim 17, wherein:
the handle comprises a power source and a wireless transceiver, both coupled to the control system;
the wireless transceiver is configured to communicate between the control system and a remote host during use of the catheter; and
the handle is operationally removable from and attachable to the catheter.

25. A medical device, comprising:
a control system;
a plurality of processing modules; and
a wire bundle connecting the control system to the plurality of processing modules, wherein the wire bundle comprises control lines, and a shared data bus comprising data lines, which is shared by the plurality of processing modules;
wherein each processing module is coupled to a respective set of sensors arranged to interface with a biological tissue site, wherein the sensors are configured to capture analog physiological signals generated from the biological tissue site;
wherein the control system is configured to generate a control signal on at least one control line of the control lines to initiate a data collection cycle by the plurality of processing modules; and
wherein in response to the control signal, each processing module of the plurality of processing modules is configured to perform a respective data collection process which comprises (i) capturing and processing an analog physiological signal on each enabled sensor in the respective set of sensors coupled to the processing module to generate a data sample for each analog physiological signal captured on each enabled sensor, and (ii) transmitting the data samples to the control system on the shared data bus;
wherein the processing modules are configured to have access to the shared data bus in a specified sequence, based on a data bus sharing protocol implemented under control of the control system, to transmit the respective data samples to the control system.

\* \* \* \* \*